(12) United States Patent
Williams et al.

(10) Patent No.: US 7,417,026 B2
(45) Date of Patent: Aug. 26, 2008

(54) MOBILIZATION OF HEMATOPOIETIC CELLS

(75) Inventors: David A. Williams, Cincinnati, OH (US); Yi Zheng, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 249 days.

(21) Appl. No.: 10/918,328

(22) Filed: Aug. 12, 2004

(65) Prior Publication Data

US 2005/0142103 A1 Jun. 30, 2005

Related U.S. Application Data

(60) Provisional application No. 60/494,718, filed on Aug. 13, 2003.

(51) Int. Cl.
*A61K 38/00* (2006.01)
(52) U.S. Cl. ........................................................ 514/12
(58) Field of Classification Search ........................ None
See application file for complete search history.

(56) References Cited

U.S. PATENT DOCUMENTS

| | | | |
|---|---|---|---|
| 4,997,834 A | 3/1991 | Muro et al. | |
| 5,492,898 A * | 2/1996 | Bertics et al. | 514/47 |
| 6,117,850 A | 9/2000 | Bleicher et al. | |
| 6,451,825 B1 | 9/2002 | Uehara et al. | |
| 6,620,591 B1 | 9/2003 | Dunlay et al. | |
| 6,642,263 B2 | 11/2003 | Sun et al. | |

FOREIGN PATENT DOCUMENTS

| | | |
|---|---|---|
| CA | 2 467 557 | 5/2003 |
| WO | WO 97/30992 | 8/1997 |
| WO | WO 99/40783 | 8/1999 |
| WO | WO 01/78761 | 10/2001 |
| WO | WO 01/83745 | 11/2001 |
| WO | WO 01/93900 | 12/2001 |
| WO | WO 01/97608 | 12/2001 |
| WO | WO 03/011277 | 2/2003 |
| WO | WO 03/042239 | 5/2003 |
| WO | WO 2004/091654 | 10/2004 |
| WO | WO 2005/017161 | 2/2005 |
| WO | WO 2005/056024 | 6/2005 |

OTHER PUBLICATIONS

Moebest et al., Blood, Nov. 2000, vol. 96, No. 11, part 1, pp. 6897a.*
International Search Report issued on the corresponding PCT Application No. PCT/US04/026459, dated Feb. 23, 2005.
Fritz, G. et al., "Rho GTPases in human breast tumours: expression and mutation analyses and correlation with clinical parameters," British Journal of Cancer, vol. 87, 635-644 (2002), XP002319076.
Gao Yuan et al., "Rational design and characterization of a Rac GTPase-specific small molecule inhibitor," Proceedings of the National Academy of Sciences of the United States of America, vol. 101, No. 20, May 18, 2004, pp. 7618-7623. XP002312007.
Gu Yi et al., "Hematopoietic cell regulation by Rac1 and Rac2 guanosine triphosphatases," Science, vol. 302, No. 5644, pp. 445-449 (2003). XP002312006, Washington DC, ISSN: 0036-8075.
Gu, Y. et al., "Rac2, a hematopoiesis-specific Rho GTPase, specifically regulates mast cell protease gene expression in bone marrow-derived mast cells," Molecular and Cellular Biology, vol. 22, No. 21, Nov. 2002, 7645-7657, XP002319073.
Gu, Y. et al., "RhoH, a hematopoietic-specific Rho GTPase, regulates proliferation, survival, migration and engraftment of hematopoietic progenitor cells," Hematopoiesis, vol. 105, No. 4, Feb. 2005, 1467-1475, XP002319078.
Hakoshima, T. et al., "Structural Basis of the Rho GTPase signaling," J. Biochem., vol. 134, 327-331 (2003), XP002319077.
Li, X. et al., Molecular and Cellular Biology, vol. 22, No. 4, Feb. 2002, 1158-1171, XP002319074.
Llevadot, J. et al., "HMG-CoA reductase inhibitor mobilizes bone marrow-derived endothelial progenitor cells," J. Clin. Investig., vol. 108, No. 3, Aug. 2001, 399-405, XP002974000.
Michaelson et al., "Differential localization of Rho GTPases in live cells: Regulation by hypervariable regions and RhoGDI binding," Journal of Cell Biology. Jan. 8, 2001, 11-126, vol. 152, No. 1.
Moon et al., "Rho GTPase-activating proteins in cell regulation," Trends in Cell Biology, Jan. 2003, 13-22, vol. 13, No. 1.
Narumiya, S. et al., Cell Signal, 5, 9-19 (1993).
Sahai et al., "Rho-GTPases and Cancer," Nature Reviews. Cancer., Feb. 2002, 133-142, vol. 2, No. 2.
Sekine, A. et al., J. Biol. Chem., 264, 8602-8605 (1989).
Somiyo, Nature, 389: 908-910 (1997).
Tao et al., "The TRQQRP motif located near the C-terminus of Rac2 is essential for Rac2 biologic functions and intracellular localization," Blood, Sep. 1, 2002, 1686-1687, vol. 100, No. 5.
Uehata et al., Nature, 389: 990-994 (1997).
Vojtek, A. B. et al., Cell, 82: 527-529 (1995).

(Continued)

*Primary Examiner*—Maryam Monshipouri
(74) *Attorney, Agent, or Firm*—Knobbe Martens Olson & Bear LLP

(57) ABSTRACT

Improved methods and pharmaceutical compositions are provided herein for mobilizing hematopoietic progenitor cells from bone marrow into peripheral blood, comprising the administration of an effective amount of an inhibitor of GTPases, such as Rac1 and Rac2 alone or in combination. Specifically, methods are disclosed for mobilizing hematopoietic stem cells into a subject's peripheral blood. In particular, embodiments of the method involve inhibition of both Rac1 and Rac2 GTPases to increase the numbers of hematopoietic stem cells into a subject's peripheral blood of a subject. The subject's blood can be processed and used to repopulate the destroyed lymphohematopoietic system of a recipient and may in the future be utilized to repair a variety of non-hematopoietic tissues. Therefore, hematopoietic stem cells mobilized into a subject's peripheral blood by the method of the invention is useful as a source of donor cells in bone marrow transplantation for the treatment of a variety of disorders, including cancer, anemia, autoimmunity and immunodeficiency. They can also be used for increasing white blood cell survival and for chemotherapy.

13 Claims, 5 Drawing Sheets

OTHER PUBLICATIONS

Wang Lei et al., "A novel strategy for specifically down-regulating individual Rho GTPase activity in tumor cells," Journal of Biological Chemistry, vol. 278, No. 45, Nov. 7, 2003, pp. 44617-44625, XP002312008, ISSN: 0021-9258.
Wennerberg et al., "Rho-family GTPases: it's not only Rac and Rho (and I like it)," Journal of Cell Science, Mar. 15, 2004, 1301-1312, vol. 117, No. 8.
Abo, A. et al., *Nature*, 1991, 668-70, 353.
Allen, W.E. et al., *J Cell Biol*, 1998, 1147-1157, 160.
Benard, V. et al., *J Biol Chem*, 1999, 13198-204, 274.
Croker, B.A. et al., *J Immunol*, Apr. 1, 2002, 3376-3386, 168.
Del Pozo, M.A. et al., *Nat Cell Biol*, Mar. 2002, 232-9, 4.
Diekmann, D. et al., *Embo J*, 1995, 5297-5305, 14.
Etienne-Manneville, S. et al., *Nature*, Dec. 12, 2002, 629-635, 420.
Gu, H. et al., *Science*, 1994, 103-106, 265.
Hall, A., *Science*, 1998, 509-514, 279.
Innocenti, M. et al., *J Cell Biol*, Jan. 6, 2003, 17-23, 160.
Kennedy, S.G. et al., *Genes Dev*, 1997, 701-713, 11.
Knaus, U.G. et al., *Science*, 1991, 1512-5, 254.
Li, B. et al., *Science*, 2000, 2219-2222, 288.
Minden, A. et al., *Science*, Dec. 9, 1994, 1719-23, 266.
Moll, J. et al., *Oncogene*, 1991, 863-866, 6.
Nobes, C.D. et al., *Cell*, 1995, 53-62, 81.
Olson, M.F. et al., *Science*, 1995, 1270-1272, 269.
Palacios, R. et al., *Proc Natl Acad Sci U S A*, May 28, 1996, 5247-5252, 93.
Papayannopoulou, T. et al., *Acta Haematol*, 1997, 97-104, 97.
Papayannopoulou, T. et al., *Blood*, Feb. 20, 2003, 141.
Ridley, A.J. et al., *Cell*, 1992, 401-410, 70.
Roberts, A.W. et al., *Immunity*, 1999, 183-196, 12.
Sherr, C.J. et al., *Genes Dev*, May 15, 1995, 1149-1163, 9.
Shirsat, N.V. et al., *Oncogene*, 1990, 769-772, 5.
Srinivasan, S. et al., *J. Cell Biol*, Feb. 3, 2003, 375-85, 160.
Van Aelst, L. et al., *Genes Dev*, 1997, 2295-2322, 11.
Williams, D.A. et al., *Blood*, 2000, 1646-1654, 96.
Yang, F.C. et al., *Immunity*, 2000, 557-568, 12.
Yang, F.C. et al., *Proc Natl Acad Sci U S A*, 2001, 5614-5618, 98.
European Office Action issued on the corresponding European Patent Application No. 04781185.6, dated May 14, 2007.
Göttig, S. et al., "Role of the monomeric GTPase Rho in hematopoietic progenitor cell migration and transplantation," Eur. J. Immunol., 36:180-189 (2006).
Henschler, R. et al., "SDF-1α-induced intracellular calcium transient involves Rho GTPase signalling and is required for migration of hematopoietic progenitor cells," Bioch. And Biophys. Res.Com, 311:1067-1071 (2003).
Ngo et al., in The Protein Folding Problem and Tertiary Structure Prediction, 1994, Merz et al. (ed.), Birkhauser, Boston, MA, pp. 433 and 492-495.
Zhang et al., *Biochemistry*, 37:5249-5257 (1998).
U.S. National Library of Medicine's controlled vocabulary database used for indexing articles for Medline/PubMed, Definition of "rho GTP-Binding Proteins", Jun. 13, 2007.
Judkins et al., "Single nucleotide polymorphisms in clinical genetic testing: the characterization of the clinical significance of genetic variants and their application in clinical research for BRCA1," Mutation Research, 573:168-179 (2005).
File History of the related U.S. Appl. No. 10/918,648, for the period of Jun. 22, 2007-Sep. 18, 2007.
File History of the related U.S. Appl. No. 11/003,935, for the period of Jun. 22, 2007-Sep. 18, 2007.

* cited by examiner

SEQUENCE LISTING

<160> NUMBER OF SEQ ID NOS: 28

<210> SEQ ID NO 1
<211> LENGTH: 4542
<212> TYPE: DNA
<213> ORGANISM: Rattus sp.

<400> SEQUENCE: 1

```
atgatgatgg caagaaagca agatgtccga atccccacct acaacatcag tgtggtggga      60
ttgtccggca ctgagaagga gaaaggccag tgcggcattg ggaagtcttg tctatgtaac     120
cgctttgtgc gcccaagtgc tgatgagttt cacctggacc acacttctgt cctcagcacc     180
agtgactttg gtgggcgggt ggtcaataat gaccatttc tgtactgggg agaagttagc     240
cgctccctgg aggactgtgt ggaatgtaag atgcacattg tggagcagac tgagtttatt     300
gacgatcaga cttttcaacc tcatcgaagc acggcactgc agccctacat caagagagcc     360
gcagccacca agcttgcttc agctgaaaaa ctcatgtatt tttgcactga ccagctaggg     420
ctggagcaag actttgagca gaaacagatg ccagatggga agctgctggt tgacggtttc     480
cttctgggca tcgatgttag caggggcatg aacaggaact tcgatgacca gctcaagttt     540
gtctccaatc tctacaatca gcttgcaaaa acaaaaaagc ccatagtaat agtcctgacc     600
aagtgtgatg agggtgttga gcggtacatt agagatgcac atacttttgc cttaagcaaa     660
aagaacctcc aggttgtaga gacctctgca aggtccaatg tgaatgtgga cttggctttc     720
acgaccttag tgcaactcat tgataagagt cgagggaaga cgaaaatcat cccttacttt     780
gaagctctca agcagcagag tcagcagata gctacagcaa aggacaagta tgagtggttg     840
gtgagccgca ttgtgaaaag tcacaatgag aactggctga gtgtcagccg aaagatgcag     900
gcctcccctg agtaccagga ctatgtctat ctggaaggga cacagaaagc caagaagctc     960
ttcctgcagc acattcaccg cctcaagcat gagcatattg agcgccggag aaagctgtac    1020
ctggcagccc tgccattggc ttttgaagcc ctcataccta atctagatga agtagaccac    1080
ctgagctgca ttaaagcaaa aaagctgtta gagactaagc cagagttctt aaagtggttt    1140
gttgtacttg aagagacacc atgggatgaa accagccaca ttgacaacat ggaaaatgag    1200
cggattccct ttgacttgat ggatactgtc cctgctgagc agttgtatga gacccacttg    1260
```

```
gagaagctga ggaatgagag gaagagagct gagatgcgaa gggctttcaa agaaaacctg   1320
gagacctctc ctttcataac tcctgggaaa ccttgggaag aagctcgtag ttttattatg   1380
aatgaagact tctaccagtg gctggaagaa tctgtgtaca tggacatcta tggcaagcac   1440
caaaagcaga ttatagaccg ggcaaaggaa gagttccaag agttgctttt ggagtattca   1500
gaattgtttt atgagctgga gctggatgct aaacccagta aggaaaagat gggtgttatc   1560
caggatgttc tgggtgaaga gcaacgattt aaagcattgc agaaactcca agcagagcgt   1620
gatgccctca ttctgaagca cattcatttt gtgtaccacc caacaaagga dacatgccca   1680
agctgtccag cttgcgtaga tgctaagatt gaacatttga tcagttctcg ctttatccga   1740
ccatctgata ggaatcagaa gaactctttg tctgacccca atattgatag gatcaatttg   1800
gttattttag gcaaagatgg ccttgcccga gagttagcca atgaaattcg agctctttgt   1860
acaaatgatg acaagtatgt aatagatggt aaaatgtatg agctttctct gaggccaata   1920
gaggggaatg ttgccgttcc tgtgaactct ttccagacac caaccttcca accccatggc   1980
tgtctctgcc tttacaattc aaaggagtcg ctgtcctatg tggtggagag tatagagaag   2040
agcagagaat ctacactggg caggcgggat aatcacttag tccacctccc cttgactta   2100 attttagtta acaagagagg ggacacaagt ggagagactc tgcacagctt aatacagcaa   2160
ggccagcaga ttgctagcaa acttcagtgt gtctttcttg atcctgcgtc tgctggcatt   2220
ggttatggac gcaacattaa cgagaagcag atcagtcaag ttctgaaggg actcctggac   2280
tctaagcgca acttaaacct ggttagttct actgctagta tcaaagattt ggctgatgtg   2340
gaccttcgaa ttgtcatgtg tctcatgtgt ggtgatcctt ttagtgcaga tgacattctc   2400
tctcctgtcc tgcagtccca aacttgtaaa tcttcccact gtgggagcag caactctgtt   2460
ttacttgaac ttccaattgg agtacacaag aagcgcattg agctgtctgt tctttcatac   2520
cattcctcat ttagcatccg aaaagagccg g ttggttcatg ggtacattgt tttttattca   2580
gccaaacgta aggcctcctt ggcaatgtta cgtgcctttc tttgtgaagt gcaggatatt   2640
atccccatcc agcttgtcgc actcactgat ggcgctatag atgtcctgga caatgactta   2700
agtcgagagc agctaacaga gggagaggaa attgcacaag aaattgatgg gagattcaca   2760
agcatccctt gtagccaccc ccagcataaa ctcgagctct tccatccctt ttttaaagat   2820
gtggtggaga aaaagaacat aatcgaggcc acacacatgt acgataatgt ggctgaggcc   2880
tgcagcacca ctgaggaggt attcaactcc cccagggctg ggtcacccct ctgcaattca   2940
aacttacagg actcagaaga agatgtggag cctccatcgt accaccttt tcgggaagat   3000 gcgacattgc cctccctgtc caaagatcat tccaagttct caatggagct ggagggaaac   3060
gacgggctgt cttcataat gagcaacttt gagagtaaac tgaacaacaa agtacctcca   3120
ccagtcaaac caaagcctcc tgtgcatttt gagatcacaa agatctttc ttacttagac   3180 caaggtcatc gggagggaca gaggaagtct atgtcttcta gcccctggat gcctcaggat   3240
ggatttgatc cttctgacta cgcagagccc atggatgctg tggtcaagcc aaggaatgag   3300
gaagaaaaca tatactcagt gccccacgac agcacccagg gcaagatcat taccattcgg   3360
aacatcaaca aagcccagtc caatggcagt ggcaatggtt ctgacagtga gatggacaca   3420
agctctctag agcgaggccg caaagtatct gcagtgagta agcctgtgct gtacaggacg   3480
agatgcaccc gcctggggcg gtttgctagt taccgcacca gcttcagtgt tgggagtgat   3540
gatgagctgg gacccatccg aaagaaagag gaggaccagg catcccaagg ttataaaggg   3600
```

-continued

```
gacaatgctg tcattcctta tgaaacagat gaggacccca ggaggaggaa tatccttcga    3660
agtctaagga ggaacaccaa gaaaccaaag cccaaacccc gaccatccat cacaaaggca    3720
acctgggaga gtaactattt tggggtgcct ttaacaacag tggtgactcc agagaagccg    3780
atacccattt tcattgaaag atgcattgag tacattgaag ccacaggact aagcacagaa    3840
ggcatctacc gggtcagcgg aaacaagtca gaaatggaaa gtttgcaaag acagtttgat    3900
caagatcaca atctggacct ggcagagaaa gacttcactg tgaacactgt ggcaggggcc    3960
atgaagagtt ttttctcgga gctaccagac cccctggtac catacagcat gcagattgac    4020
ttggtggaag ctcacaagat caacgacagg gagcagaagc tgcatgctct gaaggaagtg    4080
ctgaagaagt tccctaagga gaaccatgaa gtcttcaaat atgtcatctc ccacctgaac    4140
agagtcagcc acaacaacaa ggtgaatctt atgaccagtg agaacctgtc catctgcttc    4200
tggcccacgt tgatgcggcc tgacttcagc agcatggacg cactcacagc cactcgatcc    4260
taccagacca tcatcgagct cttcatccag cagtgcccct tcttcttcta caaccggccg    4320
atcagtgagc accggggggc tgcgctggct ccccttcagc catggcaccc actgtcccct    4380
tcctcacctc tacacctgct accagtcagc catcacctcc ccagtcacct cctccaaccc    4440
ctcagtcccc aatgcagcca ttgctctcct ctcagctcca agccgaacac acgctgtgag    4500
ccaccacagc ccaggaagca ggaaaatcag ttgtcttctt ga                     4542
```

<210> SEQ ID NO 2
<211> LENGTH: 1513
<212> TYPE: PRT
<213> ORGANISM: Rattus sp.
<220> FEATURE:
<221> NAME/KEY: DOMAIN
<222> LOCATION: (1261)..(1431)
<223> OTHER INFORMATION: p190RhoGAP domain

<400> SEQUENCE: 2

```
Met Met Met Ala Arg Lys Gln Asp Val Arg Ile Pro Thr Tyr Asn Ile
1               5                  10                  15

Ser Val Val Gly Leu Ser Gly Thr Glu Lys Glu Lys Gly Gln Cys Gly
            20                  25                  30

Ile Gly Lys Ser Cys Leu Cys Asn Arg Phe Val Arg Pro Ser Ala Asp
        35                  40                  45

Glu Phe His Leu Asp His Thr Ser Val Leu Ser Thr Ser Asp Phe Gly
    50                  55                  60

Gly Arg Val Val Asn Asn Asp His Phe Leu Tyr Trp Gly Glu Val Ser
65                  70                  75                  80

Arg Ser Leu Glu Asp Cys Val Glu Cys Lys Met His Ile Val Glu Gln
                85                  90                  95

Thr Glu Phe Ile Asp Asp Gln Thr Phe Gln Pro His Arg Ser Thr Ala
            100                 105                 110

Leu Gln Pro Tyr Ile Lys Arg Ala Ala Ala Thr Lys Leu Ala Ser Ala
        115                 120                 125

Glu Lys Leu Met Tyr Phe Cys Thr Asp Gln Leu Gly Leu Glu Gln Asp
    130                 135                 140

Phe Glu Gln Lys Gln Met Pro Asp Gly Lys Leu Leu Val Asp Gly Phe
145                 150                 155                 160

Leu Leu Gly Ile Asp Val Ser Arg Gly Met Asn Arg Asn Phe Asp Asp
                165                 170                 175

Gln Leu Lys Phe Val Ser Asn Leu Tyr Asn Gln Leu Ala Lys Thr Lys
            180                 185                 190
```

-continued

```
Lys Pro Ile Val Ile Val Leu Thr Lys Cys Asp Glu Gly Val Glu Arg
        195                 200                 205

Tyr Ile Arg Asp Ala His Thr Phe Ala Leu Ser Lys Lys Asn Leu Gln
        210                 215                 220

Val Val Glu Thr Ser Ala Arg Ser Asn Val Asn Val Asp Leu Ala Phe
225                 230                 235                 240

Thr Thr Leu Val Gln Leu Ile Asp Lys Ser Arg Gly Lys Thr Lys Ile
                245                 250                 255

Ile Pro Tyr Phe Glu Ala Leu Lys Gln Gln Ser Gln Gln Ile Ala Thr
            260                 265                 270

Ala Lys Asp Lys Tyr Glu Trp Leu Val Ser Arg Ile Val Lys Ser His
        275                 280                 285

Asn Glu Asn Trp Leu Ser Val Ser Arg Lys Met Gln Ala Ser Pro Glu
        290                 295                 300

Tyr Gln Asp Tyr Val Tyr Leu Glu Gly Thr Gln Lys Ala Lys Lys Leu
305                 310                 315                 320

Phe Leu Gln His Ile His Arg Leu Lys His Glu His Ile Glu Arg Arg
                325                 330                 335

Arg Lys Leu Tyr Leu Ala Ala Leu Pro Leu Ala Phe Glu Ala Leu Ile
            340                 345                 350

Pro Asn Leu Asp Glu Val Asp His Leu Ser Cys Ile Lys Ala Lys Lys
        355                 360                 365

Leu Leu Glu Thr Lys Pro Glu Phe Leu Lys Trp Phe Val Val Leu Glu
        370                 375                 380

Glu Thr Pro Trp Asp Glu Thr Ser His Ile Asp Asn Met Glu Asn Glu
385                 390                 395                 400

Arg Ile Pro Phe Asp Leu Met Asp Thr Val Pro Ala Glu Gln Leu Tyr
                405                 410                 415

Glu Thr His Leu Glu Lys Leu Arg Asn Glu Arg Lys Arg Ala Glu Met
            420                 425                 430

Arg Arg Ala Phe Lys Glu Asn Leu Glu Thr Ser Pro Phe Ile Thr Pro
        435                 440                 445

Gly Lys Pro Trp Glu Glu Ala Arg Ser Phe Ile Met Asn Glu Asp Phe
        450                 455                 460

Tyr Gln Trp Leu Glu Glu Ser Val Tyr Met Asp Ile Tyr Gly Lys His
465                 470                 475                 480

Gln Lys Gln Ile Ile Asp Arg Ala Lys Glu Glu Phe Gln Glu Leu Leu
                485                 490                 495

Leu Glu Tyr Ser Glu Leu Phe Tyr Glu Leu Glu Leu Asp Ala Lys Pro
            500                 505                 510

Ser Lys Glu Lys Met Gly Val Ile Gln Asp Val Leu Gly Glu Glu Gln
        515                 520                 525

Arg Phe Lys Ala Leu Gln Lys Leu Gln Ala Glu Arg Asp Ala Leu Ile
        530                 535                 540

Leu Lys His Ile His Phe Val Tyr His Pro Thr Lys Glu Thr Cys Pro
545                 550                 555                 560

Ser Cys Pro Ala Cys Val Asp Ala Lys Ile Glu His Leu Ile Ser Ser
                565                 570                 575

Arg Phe Ile Arg Pro Ser Asp Arg Asn Gln Lys Asn Ser Leu Ser Asp
            580                 585                 590

Pro Asn Ile Asp Arg Ile Asn Leu Val Ile Leu Gly Lys Asp Gly Leu
        595                 600                 605
```

-continued

```
Ala Arg Glu Leu Ala Asn Glu Ile Arg Ala Leu Cys Thr Asn Asp Asp
    610             615                 620

Lys Tyr Val Ile Asp Gly Lys Met Tyr Glu Leu Ser Leu Arg Pro Ile
625             630              635                 640

Glu Gly Asn Val Ala Val Pro Val Asn Ser Phe Gln Thr Pro Thr Phe
                645                 650             655

Gln Pro His Gly Cys Leu Cys Leu Tyr Asn Ser Lys Glu Ser Leu Ser
            660              665                 670

Tyr Val Val Glu Ser Ile Glu Lys Ser Arg Glu Ser Thr Leu Gly Arg
        675             680              685

Arg Asp Asn His Leu Val His Leu Pro Leu Thr Leu Ile Leu Val Asn
    690             695                 700

Lys Arg Gly Asp Thr Ser Gly Glu Thr Leu His Ser Leu Ile Gln Gln
705             710              715                 720

Gly Gln Gln Ile Ala Ser Lys Leu Gln Cys Val Phe Leu Asp Pro Ala
                725             730                  735

Ser Ala Gly Ile Gly Tyr Gly Arg Asn Ile Asn Glu Lys Gln Ile Ser
            740             745                 750

Gln Val Leu Lys Gly Leu Leu Asp Ser Lys Arg Asn Leu Asn Leu Val
        755             760                 765

Ser Ser Thr Ala Ser Ile Lys Asp Leu Ala Asp Val Asp Leu Arg Ile
770             775                 780

Val Met Cys Leu Met Cys Gly Asp Pro Phe Ser Ala Asp Asp Ile Leu
785             790              795                 800

Ser Pro Val Leu Gln Ser Gln Thr Cys Lys Ser Ser His Cys Gly Ser
                805             810                 815

Ser Asn Ser Val Leu Leu Glu Leu Pro Ile Gly Val His Lys Lys Arg
            820             825                 830

Ile Glu Leu Ser Val Leu Ser Tyr His Ser Ser Phe Ser Ile Arg Lys
        835             840                 845

Ser Arg Leu Val His Gly Tyr Ile Val Phe Tyr Ser Ala Lys Arg Lys
    850             855                 860

Ala Ser Leu Ala Met Leu Arg Ala Phe Leu Cys Glu Val Gln Asp Ile
865             870              875                 880

Ile Pro Ile Gln Leu Val Ala Leu Thr Asp Gly Ala Ile Asp Val Leu
                885             890                 895

Asp Asn Asp Leu Ser Arg Glu Gln Leu Thr Glu Gly Glu Glu Ile Ala
            900             905                 910

Gln Glu Ile Asp Gly Arg Phe Thr Ser Ile Pro Cys Ser His Pro Gln
        915             920                 925

His Lys Leu Glu Leu Phe His Pro Phe Phe Lys Asp Val Val Glu Lys
    930             935                 940

Lys Asn Ile Ile Glu Ala Thr His Met Tyr Asp Asn Val Ala Glu Ala
945             950              955                 960

Cys Ser Thr Thr Glu Glu Val Phe Asn Ser Pro Arg Ala Gly Ser Pro
                965             970             975

Leu Cys Asn Ser Asn Leu Gln Asp Ser Glu Asp Val Glu Pro Pro
            980             985                 990

Ser Tyr His Leu Phe Arg Glu Asp Ala Thr Leu Pro Ser Leu Ser Lys
        995             1000                1005

Asp His Ser Lys Phe Ser Met Glu Leu Glu Gly Asn Asp Gly Leu
    1010            1015                1020

Ser Phe Ile Met Ser Asn Phe Glu Ser Lys Leu Asn Asn Lys Val
```

-continued

```
              1025                1030                1035
Pro Pro Pro Val Lys Pro Lys Pro Pro Val His Phe Glu Ile Thr
        1040                1045                1050
Lys Asp Leu Ser Tyr Leu Asp Gln Gly His Arg Glu Gly Gln Arg
        1055                1060                1065
Lys Ser Met Ser Ser Ser Pro Trp Met Pro Gln Asp Gly Phe Asp
        1070                1075                1080
Pro Ser Asp Tyr Ala Glu Pro Met Asp Ala Val Val Lys Pro Arg
        1085                1090                1095
Asn Glu Glu Glu Asn Ile Tyr Ser Val Pro His Asp Ser Thr Gln
        1100                1105                1110
Gly Lys Ile Ile Thr Ile Arg Asn Ile Asn Lys Ala Gln Ser Asn
        1115                1120                1125
Gly Ser Gly Asn Gly Ser Asp Ser Glu Met Asp Thr Ser Ser Leu
        1130                1135                1140
Glu Arg Gly Arg Lys Val Ser Ala Val Ser Lys Pro Val Leu Tyr
        1145                1150                1155
Arg Thr Arg Cys Thr Arg Leu Gly Arg Phe Ala Ser Tyr Arg Thr
        1160                1165                1170
Ser Phe Ser Val Gly Ser Asp Asp Glu Leu Gly Pro Ile Arg Lys
        1175                1180                1185
Lys Glu Glu Asp Gln Ala Ser Gln Gly Tyr Lys Gly Asp Asn Ala
        1190                1195                1200
Val Ile Pro Tyr Glu Thr Asp Glu Asp Pro Arg Arg Arg Asn Ile
        1205                1210                1215
Leu Arg Ser Leu Arg Arg Asn Thr Lys Lys Pro Lys Pro Lys Pro
        1220                1225                1230
Arg Pro Ser Ile Thr Lys Ala Thr Trp Glu Ser Asn Tyr Phe Gly
        1235                1240                1245
Val Pro Leu Thr Thr Val Val Thr Pro Glu Lys Pro Ile Pro Ile
        1250                1255                1260
Phe Ile Glu Arg Cys Ile Glu Tyr Ile Glu Ala Thr Gly Leu Ser
        1265                1270                1275
Thr Glu Gly Ile Tyr Arg Val Ser Gly Asn Lys Ser Glu Met Glu
        1280                1285                1290
Ser Leu Gln Arg Gln Phe Asp Gln Asp His Asn Leu Asp Leu Ala
        1295                1300                1305
Glu Lys Asp Phe Thr Val Asn Thr Val Ala Gly Ala Met Lys Ser
        1310                1315                1320
Phe Phe Ser Glu Leu Pro Asp Pro Leu Val Pro Tyr Ser Met Gln
        1325                1330                1335
Ile Asp Leu Val Glu Ala His Lys Ile Asn Asp Arg Glu Gln Lys
        1340                1345                1350
Leu His Ala Leu Lys Glu Val Leu Lys Lys Phe Pro Lys Glu Asn
        1355                1360                1365
His Glu Val Phe Lys Tyr Val Ile Ser His Leu Asn Arg Val Ser
        1370                1375                1380
His Asn Asn Lys Val Asn Leu Met Thr Ser Glu Asn Leu Ser Ile
        1385                1390                1395
Cys Phe Trp Pro Thr Leu Met Arg Pro Asp Phe Ser Ser Met Asp
        1400                1405                1410
Ala Leu Thr Ala Thr Arg Ser Tyr Gln Thr Ile Ile Glu Leu Phe
        1415                1420                1425
```

```
Ile Gln Gln Cys Pro Phe Phe Phe Tyr Asn Arg Pro Ile Ser Glu
    1430                1435                1440

Pro Pro Gly Ala Ala Leu Ala Pro Leu Gln Pro Trp His Pro Leu
    1445                1450                1455

Ser Pro Ser Ser Pro Leu His Leu Leu Pro Val Ser His His Leu
    1460                1465                1470

Pro Ser His Leu Leu Gln Pro Leu Ser Pro Gln Cys Ser His Cys
    1475                1480                1485

Ser Pro Leu Ser Ser Lys Pro Asn Thr Arg Cys Glu Pro Pro Gln
    1490                1495                1500

Pro Arg Lys Gln Glu Asn Gln Leu Ser Ser
    1505                1510

<210> SEQ ID NO 3
<211> LENGTH: 1320
<212> TYPE: DNA
<213> ORGANISM: Homo sapiens

<400> SEQUENCE: 3
atggatccgc tctcagagct gcaggatgat ctgaccttgg atgacaccag cgaggctctg      60
aaccagctga agctggcctc catcgatgag aagaactggc cctcggatga atgcctgac     120 ttccccaagt cagatgactc caaaagcagc tccccggaac ttgtcacaca cctgaagtgg     180
gatgacccat actatgacat cgcccggcac cagatcgtgg aggtggcagg agatgacaag     240
tatgggcgga agatcattgt gtttagtgcc tgtcgaatgc cccccagcca ccagctcgac     300
cacagcaagc tcctggggta cctgaagcac accctggacc agtacgtgga gagtgactac     360
acacttctgt atctgcacca cggcctgacc agcgacaaca agccctccct cagctggctc     420
cgtgatgcct accgggagtt tgaccgcaag tacaagaaga catcaaggc cttgtacatc     480 gtgcatccaa ccatgttcat caaaactctg ctcatcctct tcaagcccct catcagcttc     540
aagttcgggc agaagatctt ctatgtgaat tacctgagcg agctgagcga gcacgtgaag     600
ctggagcagc tggggatccc tcgccaagtg ctcaaatatg cgacttcct gaaatccaca     660 cagaagagcc ccgcgacagc ccccaagccc atgcccccac ggcccccccct gcccaaccag     720 cagtttggag tctcgctgca gcacctccag gagaagaatc cagagcagga gcccattccc     780
attgtactca gggagactgt tgcctactta caggcccacg ctctcaccac cgagggcatc     840
ttccggaggt cggccaacac ccaagtggtc cgggaagtgc agcagaagta caacatgggg     900
ctgcctgtgg atttcgacca gtacaatgag ctgcacctgc agcagtcat cctcaagacc     960 ttcctccggg agcttcctga gccctgctc acctttgacc tctaccccca tgtggtgggc     1020
ttcctcaaca ttgatgaaag ccagagggtg ccagcgacac tgcaggtcct ccagacgctg     1080
cccgaggaga actaccaggt gcttcgtttc ctgactgctt cctggtgca gatttctgca     1140 cacagtgacc agaacaagat gaccaacact aacctggctg ttgttttcgg ccctaacctg     1200
ctgtgggcca aggatgcggc catcaccctc aaggccatta atcccatcaa caccttcacc     1260
aagttccttc tggatcacca aggggagctg ttcccaagcc cggaccccag cgggctctga     1320

<210> SEQ ID NO 4
<211> LENGTH: 439
<212> TYPE: PRT
<213> ORGANISM: Homo sapiens
<220> FEATURE:
<221> NAME/KEY: DOMAIN
<222> LOCATION: (257)..(426)
```

<223> OTHER INFORMATION: Cdc42GAP domain

<400> SEQUENCE: 4

```
Met Asp Pro Leu Ser Glu Leu Gln Asp Asp Leu Thr Leu Asp Thr
1               5                   10                  15

Ser Glu Ala Leu Asn Gln Leu Lys Leu Ala Ser Ile Asp Glu Lys Asn
            20                  25                  30

Trp Pro Ser Asp Glu Met Pro Asp Phe Pro Lys Ser Asp Ser Lys
        35                  40                  45

Ser Ser Ser Pro Glu Leu Val Thr His Leu Lys Trp Asp Asp Pro Tyr
    50                  55                  60

Tyr Asp Ile Ala Arg His Gln Ile Val Glu Val Ala Gly Asp Asp Lys
65                  70                  75                  80

Tyr Gly Arg Lys Ile Ile Val Phe Ser Ala Cys Arg Met Pro Pro Ser
                85                  90                  95

His Gln Leu Asp His Ser Lys Leu Leu Gly Tyr Leu Lys His Thr Leu
            100                 105                 110

Asp Gln Tyr Val Glu Ser Asp Tyr Thr Leu Leu Tyr Leu His His Gly
        115                 120                 125

Leu Thr Ser Asp Asn Lys Pro Ser Leu Ser Trp Leu Arg Asp Ala Tyr
    130                 135                 140

Arg Glu Phe Asp Arg Lys Tyr Lys Lys Asn Ile Lys Ala Leu Tyr Ile
145                 150                 155                 160

Val His Pro Thr Met Phe Ile Lys Thr Leu Leu Ile Leu Phe Lys Pro
                165                 170                 175

Leu Ile Ser Phe Lys Phe Gly Gln Lys Ile Phe Tyr Val Asn Tyr Leu
            180                 185                 190

Ser Glu Leu Ser Glu His Val Lys Leu Glu Gln Leu Gly Ile Pro Arg
        195                 200                 205

Gln Val Leu Lys Tyr Asp Asp Phe Leu Lys Ser Thr Gln Lys Ser Pro
    210                 215                 220

Ala Thr Ala Pro Lys Pro Met Pro Pro Arg Pro Pro Leu Pro Asn Gln
225                 230                 235                 240

Gln Phe Gly Val Ser Leu Gln His Leu Gln Glu Lys Asn Pro Glu Gln
                245                 250                 255

Glu Pro Ile Pro Ile Val Leu Arg Glu Thr Val Ala Tyr Leu Gln Ala
            260                 265                 270

His Ala Leu Thr Thr Glu Gly Ile Phe Arg Arg Ser Ala Asn Thr Gln
        275                 280                 285

Val Val Arg Glu Val Gln Gln Lys Tyr Asn Met Gly Leu Pro Val Asp
    290                 295                 300

Phe Asp Gln Tyr Asn Glu Leu His Leu Pro Ala Val Ile Leu Lys Thr
305                 310                 315                 320

Phe Leu Arg Glu Leu Pro Glu Pro Leu Leu Thr Phe Asp Leu Tyr Pro
                325                 330                 335

His Val Val Gly Phe Leu Asn Ile Asp Glu Ser Gln Arg Val Pro Ala
            340                 345                 350

Thr Leu Gln Val Leu Gln Thr Leu Pro Glu Glu Asn Tyr Gln Val Leu
        355                 360                 365

Arg Phe Leu Thr Ala Phe Leu Val Gln Ile Ser Ala His Ser Asp Gln
    370                 375                 380

Asn Lys Met Thr Asn Thr Asn Leu Ala Val Val Phe Gly Pro Asn Leu
385                 390                 395                 400
```

```
Leu Trp Ala Lys Asp Ala Ala Ile Thr Leu Lys Ala Ile Asn Pro Ile
            405                 410                 415

Asn Thr Phe Thr Lys Phe Leu Leu Asp His Gln Gly Glu Leu Phe Pro
            420                 425                 430

Ser Pro Asp Pro Ser Gly Leu
            435

<210> SEQ ID NO 5
<211> LENGTH: 3684
<212> TYPE: DNA
<213> ORGANISM: Homo sapiens

<400> SEQUENCE: 5
atggtggacc cggtgggctt cgcggaggcg tggaaggcgc agttcccgga ctcagagccc      60
ccgcgcatgg agctgcgctc agtgggcgac atcgagcagg agctgagcg ctgcaaggcc     120 tccattcggc gcctggagca ggaggtgaac caggagcgct tccgcatgat ctacctgcag     180
acgttgctgg ccaaggaaaa gaagagctat gaccggcagc gatggggctt ccggcgcgcg     240
gcgcaggccc ccgacggcgc ctccgagccc gagcgtccg cgtcgcgccc gcagccagcg     300
cccgccgacg gagccgaccc gccgcccgcc gaggagcccg aggcccggcc cgacggcgag     360
ggttctccgg gtaaggccag gcccgggacc gcccgcaggc ccggggcagc cgcgtcgggg     420
gaacgggacg accgggacc cccgccagc gtggcggcgc tcaggtccaa cttcgagcgg     480
atccggaagg ccatggcca gcccggggcg gacgccgaga agcccttcta cgtgaacgtc     540
gagtttcacc acgagcgcgg cctggtgaag gtcaacgaca aagaggtgtc ggaccgcatc     600
agctcccttg gcagccaggc catgcagatg agcgcaaaa agtcccagca cggcgcgggc     660
tcgagcgtgg gggatgcatc caggcccccct taccggggac gctcctcgga gagcagctgc     720
ggcgtcgacg gcgactacga ggacgccgag ttgaaccccc gcttcctgaa ggacaacctg     780
atcgacgcca atggcggtag caggcccccct tggccgcccc tggagtacca gcctaccag     840 agcatctacg tcgggggcat catggaaggg gagggcaagg gcccgctcct cgcagccag     900 agcacctctg agcaggagaa cgccttacc tggccccgca ggtcctactc ccccggagt     960 tttgaggatt gcggaggcgg ctatacccccg gactgcagct ccaatgagaa cctcacctcc    1020
agcgaggagg acttctcctc tggccagtcc agcgcgtgt ccccaagccc caccacctac    1080
cgcatgttcc gggacaaaag ccgctctccc tcgcagaact cgcaacagtc cttcgacagc    1140
agcagtcccc ccacgccgca gtgccataag cggcaccggc actgcccggt tgtcgtgtcc    1200
gaggccacca tcgtgggcgt ccgcaagacc gggcagatct ggcccaacga tgacgagggc    1260
gccttccatg gagacgcaga tggctcgttc ggaacaccac ctggatacgg ctgcgctgca    1320
gaccgggcag aggagcagcg ccggcaccaa gatgggctgc cctacattga tgactcgccc    1380
tcctcatcgc ccacctcag cagcaagggc aggggcagcc gggatgcgct ggtctcggga    1440
gccctgaagt ccactaaagc gagtgagctg gacttggaaa agggcttgga gatgagaaaa    1500
tgggtcctgt cgggaatcct ggctagcgag gagacttacc tgagccacct ggaggcactg    1560
ctgctgccca tgaagccttt gaaagccgct gccaccacct ctcagccggt gctgacgagt    1620
cagcagatcg agaccatctt cttcaaagtg cctgagctct acgagatcca aggagtcc    1680 tatgatgggc tcttcccccg cgtgcagcag tggagccacc agcagcgggt gggcgacctc    1740
ttccagaagc tggccagcca gctgggtgtg taccggggcct cgtggacaa ctacggagtt    1800 gccatggaaa tggctgagaa gtgctgtcag gccaatgctc agtttgcaga aatctccgag    1860
```

-continued

```
aacctgagag ccagaagcaa caaagatgcc aaggatccaa cgaccaagaa ctctctggaa      1920
actctgctct acaagcctgt ggaccgtgtg acgaggagca cgctggtcct ccatgacttg      1980
ctgaagcaca ctcctgccag ccaccctgac caccccttgc tgcaggacgc cctccgcatc      2040
tcacagaact tcctgtccag catcaatgag gagatcacac cccgacggca gtccatgacg      2100
gtgaagaagg gagagcaccg gcagctgctg aaggacagct tcatggtgga gctggtggag      2160
ggggcccgca agctgcggca cgtcttcctg ttcaccgacc tgcttctctg caccaagctc      2220
aagaagcaga gcggaggcaa aacgcagcag tatgactgca atggtacatt ccgctcacg       2280 gatctcagct tccagatggt ggatgaactg gaggcagtgc ccaacatccc cctggtgccc      2340
gatgaggagc tggacgcttt gaagatcaag atctcccaga tcaagagtga catccagaga     2400
gagaagaggg cgaacaaggg cagcaaggct acggagaggc tgaagaagaa gctgtcggag     2460
caggagtcac tgctgctgct tatgtctccc agcatggcct tcagggtgca cagccgcaac     2520
ggcaagagtt acacgttcct gatctcctct gactatgagc gtgcagagtg gagggagaac     2580
atccgggagc agcagaagaa gtgtttcaga agcttctccc tgacatccgt ggagctgcag     2640
atgctgacca ctcgtgtgt gaaactccag actgtccaca gcattccgct gaccatcaat      2700
aaggaagatg atgagtctcc ggggctctat gggtttctga atgtcatcgt ccactcagcc    2760
actggattta gcagagttc aaatctgtac tgcaccctgg aggtggattc ctttgggtat     2820
tttgtgaata aagcaaagac gcgcgtctac agggacacag ctgagccaaa ctggaacgag    2880 ctggaccccgc aggccctgca ggacagagac tggcagcgca ccgtcatcgc catgaatggg    2940
atcgaagtaa agctctcggt caagttcaac agcagggagt tcagcttgaa gaggatgccg    3000
tcccgaaaac agacagggggt cttcggagtc aagattgctg tggtcaccaa gagagagagg   3060
tccaaggtgc cctacatcgt gcgccagtgc gtggaggaga tcgagcgccg aggcatggag    3120
gaggtgggca tctaccgcgt gtccggtgtg ccacggacca tccaggcact gaaggcagcc    3180
ttcgacgtca ataacaagga tgtgtcggtg atgatgagcg agatggacgt gaacgccatc    3240
gcaggcacgc tgaagctgta cttccgtgag ctgccccgagc ccctcttcac tgacgagttc   3300
taccccaact tcgcagaggg catcgctctt tcagacccgg ttgcaaagga gagctgcatg    3360
ctcaacctgc tgctgtccct gccggaggcc aacctgctca ccttccttt ccttctggac    3420 cacctgaaaa gggtggcaga gaaggaggca gtcaataaga tgtccctgca caacctcgcc   3480
acggtctttg gccccacgct gctccggccc tccgagaagg agagcaagct ccctgccaac   3540
cccagccagc ctatcaccat gactgacagc tggtccttgg aggtcatgtc ccaggtccag   3600
gtgctgctgt acttcctgca gctggaggcc atccctgccc cggacagcaa gagacagagc   3660
atcctgttct ccaccgaagt ctaa                                            3684
```

<210> SEQ ID NO 6
<211> LENGTH: 1227
<212> TYPE: PRT
<213> ORGANISM: Homo sapiens
<220> FEATURE:
<221> NAME/KEY: DOMAIN
<222> LOCATION: (1014)..(1205)
<223> OTHER INFORMATION: BcrGAP domain

<400> SEQUENCE: 6

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

```
Gln Glu Leu Glu Arg Cys Lys Ala Ser Ile Arg Arg Leu Glu Gln Glu
             35                  40                  45

Val Asn Gln Glu Arg Phe Arg Met Ile Tyr Leu Gln Thr Leu Leu Ala
 50                  55                  60

Lys Glu Lys Lys Ser Tyr Asp Arg Gln Arg Trp Gly Phe Arg Arg Ala
 65                  70                  75                  80

Ala Gln Ala Pro Asp Gly Ala Ser Glu Pro Arg Ala Ser Ala Ser Arg
                 85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ser Gly Glu Arg Asp Asp
            130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
                180                 185                 190

Asp Lys Glu Val Ser Asp Arg Ile Ser Ser Leu Gly Ser Gln Ala Met
            195                 200                 205

Gln Met Glu Arg Lys Lys Ser Gln His Gly Ala Gly Ser Ser Val Gly
            210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
            260                 265                 270

Pro Leu Glu Tyr Gln Pro Tyr Gln Ser Ile Tyr Val Gly Gly Ile Met
            275                 280                 285

Glu Gly Glu Gly Lys Gly Pro Leu Leu Arg Ser Gln Ser Thr Ser Glu
            290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
            355                 360                 365

Ser Pro Ser Gln Asn Ser Gln Gln Ser Phe Asp Ser Ser Ser Pro Pro
            370                 375                 380

Thr Pro Gln Cys His Lys Arg His Arg His Cys Pro Val Val Ser
385                 390                 395                 400

Glu Ala Thr Ile Val Gly Val Arg Lys Thr Gly Gln Ile Trp Pro Asn
                405                 410                 415

Asp Asp Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Gln Arg Arg
            435                 440                 445
```

-continued

```
His Gln Asp Gly Leu Pro Tyr Ile Asp Asp Ser Pro Ser Ser Pro
    450                 455                 460
His Leu Ser Ser Lys Gly Arg Gly Ser Arg Asp Ala Leu Val Ser Gly
465                 470                 475                 480
Ala Leu Lys Ser Thr Lys Ala Ser Glu Leu Asp Leu Glu Lys Gly Leu
                485                 490                 495
Glu Met Arg Lys Trp Val Leu Ser Gly Ile Leu Ala Ser Glu Glu Thr
            500                 505                 510
Tyr Leu Ser His Leu Glu Ala Leu Leu Pro Met Lys Pro Leu Lys
        515                 520                 525
Ala Ala Ala Thr Thr Ser Gln Pro Val Leu Thr Ser Gln Gln Ile Glu
    530                 535                 540
Thr Ile Phe Phe Lys Val Pro Glu Leu Tyr Glu Ile His Lys Glu Ser
545                 550                 555                 560
Tyr Asp Gly Leu Phe Pro Arg Val Gln Gln Trp Ser His Gln Gln Arg
                565                 570                 575
Val Gly Asp Leu Phe Gln Lys Leu Ala Ser Gln Leu Gly Val Tyr Arg
            580                 585                 590
Ala Phe Val Asp Asn Tyr Gly Val Ala Met Glu Met Ala Glu Lys Cys
        595                 600                 605
Cys Gln Ala Asn Ala Gln Phe Ala Glu Ile Ser Glu Asn Leu Arg Ala
    610                 615                 620
Arg Ser Asn Lys Asp Ala Lys Asp Pro Thr Thr Lys Asn Ser Leu Glu
625                 630                 635                 640
Thr Leu Leu Tyr Lys Pro Val Asp Arg Val Thr Arg Ser Thr Leu Val
                645                 650                 655
Leu His Asp Leu Leu Lys His Thr Pro Ala Ser His Pro Asp His Pro
            660                 665                 670
Leu Leu Gln Asp Ala Leu Arg Ile Ser Gln Asn Phe Leu Ser Ser Ile
        675                 680                 685
Asn Glu Glu Ile Thr Pro Arg Arg Gln Ser Met Thr Val Lys Lys Gly
    690                 695                 700
Glu His Arg Gln Leu Leu Lys Asp Ser Phe Met Val Glu Leu Val Glu
705                 710                 715                 720
Gly Ala Arg Lys Leu Arg His Val Phe Leu Phe Thr Asp Leu Leu Leu
                725                 730                 735
Cys Thr Lys Leu Lys Lys Gln Ser Gly Gly Lys Thr Gln Gln Tyr Asp
            740                 745                 750
Cys Lys Trp Tyr Ile Pro Leu Thr Asp Leu Ser Phe Gln Met Val Asp
        755                 760                 765
Glu Leu Glu Ala Val Pro Asn Ile Pro Leu Val Pro Asp Glu Glu Leu
    770                 775                 780
Asp Ala Leu Lys Ile Lys Ile Ser Gln Ile Lys Ser Asp Ile Gln Arg
785                 790                 795                 800
Glu Lys Arg Ala Asn Lys Gly Ser Lys Ala Thr Glu Arg Leu Lys Lys
                805                 810                 815
Lys Leu Ser Glu Gln Glu Ser Leu Leu Leu Leu Met Ser Pro Ser Met
            820                 825                 830
Ala Phe Arg Val His Ser Arg Asn Gly Lys Ser Tyr Thr Phe Leu Ile
        835                 840                 845
Ser Ser Asp Tyr Glu Arg Ala Glu Trp Arg Glu Asn Ile Arg Glu Gln
    850                 855                 860
Gln Lys Lys Cys Phe Arg Ser Phe Ser Leu Thr Ser Val Glu Leu Gln
```

```
                           865                 870                 875                 880

Met Leu Thr Asn Ser Cys Val Lys Leu Gln Thr Val His Ser Ile Pro
                    885                 890                 895

Leu Thr Ile Asn Lys Glu Asp Asp Glu Ser Pro Gly Leu Tyr Gly Phe
                900                 905                 910

Leu Asn Val Ile Val His Ser Ala Thr Gly Phe Lys Gln Ser Ser Asn
            915                 920                 925

Leu Tyr Cys Thr Leu Glu Val Asp Ser Phe Gly Tyr Phe Val Asn Lys
        930                 935                 940

Ala Lys Thr Arg Val Tyr Arg Asp Thr Ala Glu Pro Asn Trp Asn Glu
945                 950                 955                 960

Leu Asp Pro Gln Ala Leu Gln Asp Arg Asp Trp Gln Arg Thr Val Ile
                965                 970                 975

Ala Met Asn Gly Ile Glu Val Lys Leu Ser Val Lys Phe Asn Ser Arg
            980                 985                 990

Glu Phe Ser Leu Lys Arg Met Pro  Ser Arg Lys Gln Thr  Gly Val Phe
        995                 1000                1005

Gly Val  Lys Ile Ala Val Val  Thr Lys Arg Glu Arg  Ser Lys Val
    1010                1015                1020

Pro Tyr  Ile Val Arg Gln Cys  Val Glu Glu Ile Glu  Arg Arg Gly
    1025                1030                1035

Met Glu  Glu Val Gly Ile Tyr  Arg Val Ser Gly Val  Ala Thr Asp
    1040                1045                1050

Ile Gln  Ala Leu Lys Ala Ala  Phe Asp Val Asn Asn  Lys Asp Val
    1055                1060                1065

Ser Val  Met Met Ser Glu Met  Asp Val Asn Ala Ile  Ala Gly Thr
    1070                1075                1080

Leu Lys  Leu Tyr Phe Arg Glu  Leu Pro Glu Pro Leu  Phe Thr Asp
    1085                1090                1095

Glu Phe  Tyr Pro Asn Phe Ala  Glu Gly Ile Ala Leu  Ser Asp Pro
    1100                1105                1110

Val Ala  Lys Glu Ser Cys Met  Leu Asn Leu Leu Leu  Ser Leu Pro
    1115                1120                1125

Glu Ala  Asn Leu Leu Thr Phe  Leu Phe Leu Leu Asp  His Leu Lys
    1130                1135                1140

Arg Val  Ala Glu Lys Glu Ala  Val Asn Lys Met Ser  Leu His Asn
    1145                1150                1155

Leu Ala  Thr Val Phe Gly Pro  Thr Leu Leu Arg Pro  Ser Glu Lys
    1160                1165                1170

Glu Ser  Lys Leu Pro Ala Asn  Pro Ser Gln Pro Ile  Thr Met Thr
    1175                1180                1185

Asp Ser  Trp Ser Leu Glu Val  Met Ser Gln Val Gln  Val Leu Leu
    1190                1195                1200

Tyr Phe  Leu Gln Leu Glu Ala  Ile Pro Ala Pro Asp  Ser Lys Arg
    1205                1210                1215

Gln Ser  Ile Leu Phe Ser Thr  Glu Val
    1220                1225

<210> SEQ ID NO 7
<211> LENGTH: 280
<212> TYPE: PRT
<213> ORGANISM: Artificial
<220> FEATURE:
<223> OTHER INFORMATION: chimeric fusion peptide/p190RhoGAP plus
      c-terminus tail section of the targeted GTPase
```

```
<400> SEQUENCE: 7

Val Pro Leu Thr Thr Val Val Thr Pro Glu Lys Pro Ile Pro Ile Phe
1               5                   10                  15

Ile Glu Arg Cys Ile Glu Tyr Ile Glu Ala Thr Gly Leu Ser Thr Glu
                20                  25                  30

Gly Ile Tyr Arg Val Ser Gly Asn Lys Ser Glu Met Glu Ser Leu Gln
            35                  40                  45

Arg Gln Phe Asp Gln Asp His Asn Leu Asp Leu Ala Glu Lys Asp Phe
        50                  55                  60

Thr Val Asn Thr Val Ala Gly Ala Met Lys Ser Phe Phe Ser Glu Leu
65                  70                  75                  80

Pro Asp Pro Leu Val Pro Tyr Ser Met Gln Ile Asp Leu Val Glu Ala
                85                  90                  95

His Lys Ile Asn Asp Arg Glu Gln Lys Leu His Ala Leu Lys Glu Val
            100                 105                 110

Leu Lys Lys Phe Pro Lys Glu Asn His Glu Val Phe Lys Tyr Val Ile
        115                 120                 125

Ser His Leu Asn Arg Val Ser His Asn Asn Lys Val Asn Leu Met Thr
    130                 135                 140

Ser Glu Asn Leu Ser Ile Cys Phe Trp Pro Thr Leu Met Arg Pro Asp
145                 150                 155                 160

Phe Ser Ser Met Asp Ala Leu Thr Ala Thr Arg Ser Tyr Gln Thr Ile
                165                 170                 175

Ile Glu Leu Phe Ile Gln Gln Cys Pro Phe Phe Phe Tyr Asn Arg Pro
            180                 185                 190

Ile Ser Glu Pro Pro Gly Ala Ala Leu Ala Pro Leu Gln Pro Trp His
        195                 200                 205

Pro Leu Ser Pro Ser Pro Leu His Leu Leu Pro Val Ser His His
    210                 215                 220

Leu Pro Ser His Leu Leu Gln Pro Leu Ser Pro Gln Cys Ser His Cys
225                 230                 235                 240

Ser Pro Leu Ser Ser Lys Pro Asn Thr Arg Cys Glu Pro Pro Gln Pro
                245                 250                 255

Arg Lys Gln Glu Asn Gln Leu Ser Ser Leu Gln Ala Arg Arg Gly Lys
            260                 265                 270

Lys Lys Ser Gly Cys Leu Val Leu
        275                 280

<210> SEQ ID NO 8
<211> LENGTH: 283
<212> TYPE: PRT
<213> ORGANISM: Artificial
<220> FEATURE:
<223> OTHER INFORMATION: chimeric fusion peptide/p190RhoGAP plus
      c-terminus tail section of the targeted GTPase

<400> SEQUENCE: 8

Val Pro Leu Thr Thr Val Val Thr Pro Glu Lys Pro Ile Pro Ile Phe
1               5                   10                  15

Ile Glu Arg Cys Ile Glu Tyr Ile Glu Ala Thr Gly Leu Ser Thr Glu
                20                  25                  30

Gly Ile Tyr Arg Val Ser Gly Asn Lys Ser Glu Met Glu Ser Leu Gln
            35                  40                  45

Arg Gln Phe Asp Gln Asp His Asn Leu Asp Leu Ala Glu Lys Asp Phe
        50                  55                  60
```

```
Thr Val Asn Thr Val Ala Gly Ala Met Lys Ser Phe Phe Ser Glu Leu
 65                  70                  75                  80

Pro Asp Pro Leu Val Pro Tyr Ser Met Gln Ile Asp Leu Val Glu Ala
                 85                  90                  95

His Lys Ile Asn Asp Arg Glu Gln Lys Leu His Ala Leu Lys Glu Val
            100                 105                 110

Leu Lys Lys Phe Pro Lys Glu Asn His Glu Val Phe Lys Tyr Val Ile
        115                 120                 125

Ser His Leu Asn Arg Val Ser His Asn Asn Lys Val Asn Leu Met Thr
    130                 135                 140

Ser Glu Asn Leu Ser Ile Cys Phe Trp Pro Thr Leu Met Arg Pro Asp
145                 150                 155                 160

Phe Ser Ser Met Asp Ala Leu Thr Ala Thr Arg Ser Tyr Gln Thr Ile
                165                 170                 175

Ile Glu Leu Phe Ile Gln Gln Cys Pro Phe Phe Phe Tyr Asn Arg Pro
            180                 185                 190

Ile Ser Glu Pro Pro Gly Ala Ala Leu Ala Pro Leu Gln Pro Trp His
        195                 200                 205

Pro Leu Ser Pro Ser Ser Pro Leu His Leu Leu Pro Val Ser His His
    210                 215                 220

Leu Pro Ser His Leu Leu Gln Pro Leu Ser Pro Gln Cys Ser His Cys
225                 230                 235                 240

Ser Pro Leu Ser Ser Lys Pro Asn Thr Arg Cys Glu Pro Pro Gln Pro
                245                 250                 255

Arg Lys Gln Glu Asn Gln Leu Ser Ser Leu Gln Lys Arg Tyr Gly Ser
            260                 265                 270

Gln Asn Gly Cys Ile Asn Cys Cys Lys Val Leu
        275                 280

<210> SEQ ID NO 9
<211> LENGTH: 298
<212> TYPE: PRT
<213> ORGANISM: Artificial
<220> FEATURE:
<223> OTHER INFORMATION: chimeric fusion peptide/p190RhoGAP plus
      c-terminus tail section of the targeted GTPase

<400> SEQUENCE: 9

Val Pro Leu Thr Thr Val Thr Pro Glu Lys Pro Ile Pro Ile Phe
 1               5                  10                  15

Ile Glu Arg Cys Ile Glu Tyr Ile Glu Ala Thr Gly Leu Ser Thr Glu
            20                  25                  30

Gly Ile Tyr Arg Val Ser Gly Asn Lys Ser Glu Met Glu Ser Leu Gln
        35                  40                  45

Arg Gln Phe Asp Gln Asp His Asn Leu Asp Leu Ala Glu Lys Asp Phe
    50                  55                  60

Thr Val Asn Thr Val Ala Gly Ala Met Lys Ser Phe Phe Ser Glu Leu
 65                  70                  75                  80

Pro Asp Pro Leu Val Pro Tyr Ser Met Gln Ile Asp Leu Val Glu Ala
                 85                  90                  95

His Lys Ile Asn Asp Arg Glu Gln Lys Leu His Ala Leu Lys Glu Val
            100                 105                 110

Leu Lys Lys Phe Pro Lys Glu Asn His Glu Val Phe Lys Tyr Val Ile
        115                 120                 125

Ser His Leu Asn Arg Val Ser His Asn Asn Lys Val Asn Leu Met Thr
```

```
                130                 135                 140
Ser Glu Asn Leu Ser Ile Cys Phe Trp Pro Thr Leu Met Arg Pro Asp
145                 150                 155                 160

Phe Ser Ser Met Asp Ala Leu Thr Ala Thr Arg Ser Tyr Gln Thr Ile
                165                 170                 175

Ile Glu Leu Phe Ile Gln Gln Cys Pro Phe Phe Phe Tyr Asn Arg Pro
                180                 185                 190

Ile Ser Glu Pro Pro Gly Ala Ala Leu Ala Pro Leu Gln Pro Trp His
                195                 200                 205

Pro Leu Ser Pro Ser Ser Pro Leu His Leu Leu Pro Val Ser His His
            210                 215                 220

Leu Pro Ser His Leu Leu Gln Pro Leu Ser Pro Gln Cys Ser His Cys
225                 230                 235                 240

Ser Pro Leu Ser Ser Lys Pro Asn Thr Arg Cys Glu Pro Pro Gln Pro
                245                 250                 255

Arg Lys Gln Glu Asn Gln Leu Ser Ser Leu Gln Lys Arg Tyr Gly Ser
                260                 265                 270

Gln Asn Gly Cys Ile Asn Cys Cys Lys Val Leu Leu Gln Val Arg Lys
                275                 280                 285

Asn Lys Arg Arg Arg Gly Cys Pro Ile Leu
                290                 295

<210> SEQ ID NO 10
<211> LENGTH: 215
<212> TYPE: PRT
<213> ORGANISM: Artificial
<220> FEATURE:
<223> OTHER INFORMATION: chimeric fusion peptide/Cdc42GAP plus
      c-terminus tail section of the targeted GTPase

<400> SEQUENCE: 10

Leu Pro Asn Gln Gln Phe Gly Val Ser Leu Gln His Leu Gln Glu Lys
1               5                   10                  15

Asn Pro Glu Gln Glu Pro Ile Pro Ile Val Leu Arg Glu Thr Val Ala
                20                  25                  30

Tyr Leu Gln Ala His Ala Leu Thr Thr Glu Gly Ile Phe Arg Arg Ser
                35                  40                  45

Ala Asn Thr Gln Val Val Arg Glu Val Gln Gln Lys Tyr Asn Met Gly
                50                  55                  60

Leu Pro Val Asp Phe Asp Gln Tyr Asn Glu Leu His Leu Pro Ala Val
65                  70                  75                  80

Ile Leu Lys Thr Phe Leu Arg Glu Leu Pro Glu Pro Leu Leu Thr Phe
                85                  90                  95

Asp Leu Tyr Pro His Val Val Gly Phe Leu Asn Ile Asp Glu Ser Gln
                100                 105                 110

Arg Val Pro Ala Thr Leu Gln Val Leu Gln Thr Leu Pro Glu Glu Asn
                115                 120                 125

Tyr Gln Val Leu Arg Phe Leu Thr Ala Phe Leu Val Gln Ile Ser Ala
                130                 135                 140

His Ser Asp Gln Asn Lys Met Thr Asn Thr Asn Leu Ala Val Val Phe
145                 150                 155                 160

Gly Pro Asn Leu Leu Trp Ala Lys Asp Ala Ala Ile Thr Leu Lys Ala
                165                 170                 175

Ile Asn Pro Ile Asn Thr Phe Thr Lys Phe Leu Leu Asp His Gln Gly
                180                 185                 190
```

```
Glu Leu Phe Pro Ser Pro Asp Pro Ser Gly Leu Pro Glu Pro Lys Lys
        195                 200                 205

Ser Arg Arg Cys Val Leu Leu
    210                 215

<210> SEQ ID NO 11
<211> LENGTH: 244
<212> TYPE: PRT
<213> ORGANISM: Artificial
<220> FEATURE:
<223> OTHER INFORMATION: chimeric fusion peptide/BcrGAP plus c-terminus
      tail section of the targeted GTPase

<400> SEQUENCE: 11

Leu Lys Arg Met Pro Ser Arg Lys Gln Thr Gly Val Phe Gly Val Lys
1               5                   10                  15

Ile Ala Val Val Thr Lys Arg Glu Arg Ser Lys Val Pro Tyr Ile Val
                20                  25                  30

Arg Gln Cys Val Glu Glu Ile Glu Arg Gly Met Glu Glu Val Gly
            35                  40                  45

Ile Tyr Arg Val Ser Gly Val Ala Thr Asp Ile Gln Ala Leu Lys Ala
    50                  55                  60

Ala Phe Asp Val Asn Asn Lys Asp Val Ser Val Met Met Ser Glu Met
65                  70                  75                  80

Asp Val Asn Ala Ile Ala Gly Thr Leu Lys Leu Tyr Phe Arg Glu Leu
                85                  90                  95

Pro Glu Pro Leu Phe Thr Asp Glu Phe Tyr Pro Asn Phe Ala Glu Gly
            100                 105                 110

Ile Ala Leu Ser Asp Pro Val Ala Lys Glu Ser Cys Met Leu Asn Leu
    115                 120                 125

Leu Leu Ser Leu Pro Glu Ala Asn Leu Leu Thr Phe Leu Phe Leu Leu
130                 135                 140

Asp His Leu Lys Arg Val Ala Glu Lys Glu Ala Val Asn Lys Met Ser
145                 150                 155                 160

Leu His Asn Leu Ala Thr Val Phe Gly Pro Thr Leu Leu Arg Pro Ser
                165                 170                 175

Glu Lys Glu Ser Lys Leu Pro Ala Asn Pro Ser Gln Pro Ile Thr Met
            180                 185                 190

Thr Asp Ser Trp Ser Leu Glu Val Met Ser Gln Val Gln Val Leu Leu
    195                 200                 205

Tyr Phe Leu Gln Leu Glu Ala Ile Pro Ala Pro Asp Ser Lys Arg Gln
        210                 215                 220

Ser Ile Leu Phe Ser Thr Glu Val Pro Val Lys Lys Arg Lys Arg Lys
225                 230                 235                 240

Cys Leu Leu Leu

<210> SEQ ID NO 12
<211> LENGTH: 244
<212> TYPE: PRT
<213> ORGANISM: Artificial
<220> FEATURE:
<223> OTHER INFORMATION: chimeric fusion peptide/BcrGAP plus c-terminus
      tail section of the targeted GTPase

<400> SEQUENCE: 12

Leu Lys Arg Met Pro Ser Arg Lys Gln Thr Gly Val Phe Gly Val Lys
1               5                   10                  15

Ile Ala Val Val Thr Lys Arg Glu Arg Ser Lys Val Pro Tyr Ile Val
```

```
            20                  25                  30
Arg Gln Cys Val Glu Glu Ile Glu Arg Arg Gly Met Glu Glu Val Gly
         35                  40                  45

Ile Tyr Arg Val Ser Gly Val Ala Thr Asp Ile Gln Ala Leu Lys Ala
 50                  55                  60

Ala Phe Asp Val Asn Asn Lys Asp Val Ser Val Met Met Ser Glu Met
 65                  70                  75                  80

Asp Val Asn Ala Ile Ala Gly Thr Leu Lys Leu Tyr Phe Arg Glu Leu
                 85                  90                  95

Pro Glu Pro Leu Phe Thr Asp Glu Phe Tyr Pro Asn Phe Ala Glu Gly
             100                 105                 110

Ile Ala Leu Ser Asp Pro Val Ala Lys Glu Ser Cys Met Leu Asn Leu
         115                 120                 125

Leu Leu Ser Leu Pro Glu Ala Asn Leu Leu Thr Phe Leu Phe Leu Leu
     130                 135                 140

Asp His Leu Lys Arg Val Ala Glu Lys Glu Ala Val Asn Lys Met Ser
145                 150                 155                 160

Leu His Asn Leu Ala Thr Val Phe Gly Pro Thr Leu Leu Arg Pro Ser
                 165                 170                 175

Glu Lys Glu Ser Lys Leu Pro Ala Asn Pro Ser Gln Pro Ile Thr Met
             180                 185                 190

Thr Asp Ser Trp Ser Leu Glu Val Met Ser Gln Val Gln Val Leu Leu
         195                 200                 205

Tyr Phe Leu Gln Leu Glu Ala Ile Pro Ala Pro Asp Ser Lys Arg Gln
     210                 215                 220

Ser Ile Leu Phe Ser Thr Glu Val Pro Thr Arg Gln Gln Lys Arg Ala
225                 230                 235                 240

Cys Ser Leu Leu

<210> SEQ ID NO 13
<211> LENGTH: 244
<212> TYPE: PRT
<213> ORGANISM: Artificial
<220> FEATURE:
<223> OTHER INFORMATION: chimeric fusion peptide/BcrGAP plus c-terminus
      tail section of the targeted GTPase

<400> SEQUENCE: 13

Leu Lys Arg Met Pro Ser Arg Lys Gln Thr Gly Val Phe Gly Val Lys
 1               5                  10                  15

Ile Ala Val Val Thr Lys Arg Glu Arg Ser Lys Val Pro Tyr Ile Val
                 20                  25                  30

Arg Gln Cys Val Glu Glu Ile Glu Arg Arg Gly Met Glu Glu Val Gly
         35                  40                  45

Ile Tyr Arg Val Ser Gly Val Ala Thr Asp Ile Gln Ala Leu Lys Ala
 50                  55                  60

Ala Phe Asp Val Asn Asn Lys Asp Val Ser Val Met Met Ser Glu Met
 65                  70                  75                  80

Asp Val Asn Ala Ile Ala Gly Thr Leu Lys Leu Tyr Phe Arg Glu Leu
                 85                  90                  95

Pro Glu Pro Leu Phe Thr Asp Glu Phe Tyr Pro Asn Phe Ala Glu Gly
             100                 105                 110

Ile Ala Leu Ser Asp Pro Val Ala Lys Glu Ser Cys Met Leu Asn Leu
         115                 120                 125

Leu Leu Ser Leu Pro Glu Ala Asn Leu Leu Thr Phe Leu Phe Leu Leu
```

```
                130                 135                 140
Asp His Leu Lys Arg Val Ala Glu Lys Glu Ala Val Asn Lys Met Ser
145                 150                 155                 160

Leu His Asn Leu Ala Thr Val Phe Gly Pro Thr Leu Leu Arg Pro Ser
                165                 170                 175

Glu Lys Glu Ser Lys Leu Pro Ala Asn Pro Ser Gln Pro Ile Thr Met
            180                 185                 190

Thr Asp Ser Trp Ser Leu Glu Val Met Ser Gln Val Gln Val Leu Leu
        195                 200                 205

Tyr Phe Leu Gln Leu Glu Ala Ile Pro Ala Pro Asp Ser Lys Arg Gln
    210                 215                 220

Ser Ile Leu Phe Ser Thr Glu Val Pro Val Lys Lys Pro Gly Lys Lys
225                 230                 235                 240

Cys Thr Val Phe

<210> SEQ ID NO 14
<211> LENGTH: 15
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 14

Leu Gln Ala Arg Arg Gly Lys Lys Lys Ser Gly Cys Leu Val Leu
1               5                   10                  15

<210> SEQ ID NO 15
<211> LENGTH: 18
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 15

Leu Gln Lys Arg Tyr Gly Ser Gln Asn Gly Cys Ile Asn Cys Cys Lys
1               5                   10                  15

Val Leu

<210> SEQ ID NO 16
<211> LENGTH: 15
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 16

Leu Gln Val Arg Lys Asn Lys Arg Arg Arg Gly Cys Pro Ile Leu
1               5                   10                  15

<210> SEQ ID NO 17
<211> LENGTH: 12
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 17

Pro Glu Pro Lys Lys Ser Arg Arg Cys Val Leu Leu
1               5                   10
```

```
<210> SEQ ID NO 18
<211> LENGTH: 12
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 18

Pro Val Lys Lys Arg Lys Arg Lys Cys Leu Leu Leu
1               5                   10

<210> SEQ ID NO 19
<211> LENGTH: 12
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 19

Pro Thr Arg Gln Gln Lys Arg Ala Cys Ser Leu Leu
1               5                   10

<210> SEQ ID NO 20
<211> LENGTH: 12
<212> TYPE: PRT
<213> ORGANISM: Artificial
<220> FEATURE:
<223> OTHER INFORMATION: synthetic construct/c-terminus tail section of
      the targeted GTPase

<400> SEQUENCE: 20

Pro Val Lys Lys Pro Gly Lys Lys Cys Thr Val Phe
1               5                   10

<210> SEQ ID NO 21
<211> LENGTH: 12
<212> TYPE: PRT
<213> ORGANISM: Artificial
<220> FEATURE:
<223> OTHER INFORMATION: synthetic construct of a membrane-translocating
    peptide

<400> SEQUENCE: 21

Pro Thr Arg Gln Gln Lys Arg Pro Cys Ser Leu Leu
1               5                   10

<210> SEQ ID NO 22
<211> LENGTH: 14
<212> TYPE: PRT
<213> ORGANISM: Artificial
<220> FEATURE:
<223> OTHER INFORMATION: synthetic construct of a membrane-translocating
      peptide

<400> SEQUENCE: 22

Pro Gln Pro Thr Arg Gln Gln Lys Arg Pro Cys Ser Leu Leu
1               5                   10

<210> SEQ ID NO 23
<211> LENGTH: 16
<212> TYPE: PRT
<213> ORGANISM: Artificial
<220> FEATURE:
<223> OTHER INFORMATION: synthetic construct of a membrane-translocating
      peptide
```

<400> SEQUENCE: 23

Gly Arg Arg Arg Arg Arg Arg Gly Thr Arg Gln Gln Lys Arg Pro
1               5                   10                  15

<210> SEQ ID NO 24
<211> LENGTH: 16
<212> TYPE: PRT
<213> ORGANISM: Artificial
<220> FEATURE:
<223> OTHER INFORMATION: synthetic construct of a membrane-translocating
      peptide

<400> SEQUENCE: 24

Gly Arg Arg Arg Arg Arg Arg Arg Gly Arg Pro Arg Gln Thr Gln Lys
1               5                   10                  15

<210> SEQ ID NO 25
<211> LENGTH: 20
<212> TYPE: PRT
<213> ORGANISM: Artificial
<220> FEATURE:
<223> OTHER INFORMATION: synthetic construct of a membrane-translocating
      peptide

<400> SEQUENCE: 25

Gly Arg Arg Arg Arg Arg Arg Gly Thr Arg Gln Gln Lys Arg Pro
1               5                   10                  15

Cys Ser Leu Leu
            20

<210> SEQ ID NO 26
<211> LENGTH: 78
<212> TYPE: DNA
<213> ORGANISM: Artificial
<220> FEATURE:
<223> OTHER INFORMATION: DNA primer sequence used in PCR

<400> SEQUENCE: 26
gcgaattctc acaagacaag gcaaccagat tttttcttcc cacgtctagc ttgcagagaa    60
gacaactgat tttcctgc                                                 78

<210> SEQ ID NO 27
<211> LENGTH: 85
<212> TYPE: DNA
<213> ORGANISM: Artificial
<220> FEATURE:
<223> OTHER INFORMATION: DNA primer sequence used in PCR

<400> SEQUENCE: 27
gcgaattctc atagcacctt gcagcagttg atgcagccgt tctgggagcc gtagcttctg    60
cagagaagac aactgatttt cctgc                                         85

<210> SEQ ID NO 28
<211> LENGTH: 78
<212> TYPE: DNA
<213> ORGANISM: Artificial
<220> FEATURE:
<223> OTHER INFORMATION: DNA primer sequence used in PCR

<400> SEQUENCE: 28
gcgaattctc agagaatggg acagcccctc cgacgcttgt tcttgcggac ctggagagaa    60
gacaactgat tttcctgc                                                 78

MOBILIZATION OF HEMATOPOIETIC CELLS

RELATED APPLICATIONS

This application claims priority to U.S. Provisional application 60/494,718, filed Aug. 13, 2003, herein incorporated by reference in its entirety.

This invention was made in part with Government support under Grant Nos. R01DK59955 and R01GM60523, awarded by the National Institutes of Health. The Government may have certain rights in this invention.

FIELD OF THE INVENTION

The present invention relates generally to improved methods and pharmaceutical compositions for mobilizing hematopoietic stem and progenitor cell from bone marrow into peripheral blood by administration of at least one inhibitor of a GTPase, such as Rac1 and/or Rac2 GTPase.

BACKGROUND OF THE INVENTION

The various mature blood cell types are all ultimately derived from a single class of progenitor cell known as hematopoietic stem cells. True stem cells are both pluripotent—that is they can give rise to all cell types—and capable of self-renewal. This is defined by their ability to repopulate an individual whose hematopoietic system has been destroyed by radiation or chemotherapy. Stem cells represent a very small percentage of bone marrow cells, and are normally quiescent. When stimulated to divide, they give rise to more committed, differentiated daughter cells with less proliferative potential, called "early progenitor" cells. Sequential rounds of division and differentiation give rise to an enormous amplification of cell numbers, necessary for the production of mature blood cells. This process of division and differentiation is subject to regulation at many levels to control cell production.

Leukocytic, hematopoietic cells are important in maintaining the body's defense against disease. For example, macrophages and lymphocytes are involved in potentiating the body's response to infection and tumors; granulocytes (neutrophils, eosinophils and basophils) are involved in overcoming infection, parasites and tumors. Other cell types derived from hematopoietic stem cells include platelets and erythrocytes.

Treatment of various cancers increasingly involves cytoreductive therapy, including high dose chemotherapy or radiation therapy. These therapies decrease a patient's white blood cell counts, suppress bone marrow hematopoietic activity, and increase the patient's risk of infection and/or hemorrhage. Depending on the degree of bone marrow damage (i.e., suppression), patients who undergo cytoreductive therapy must also receive therapy to reconstitute bone marrow function (hematopoiesis). Current treatments to manage the problems that result from prolonged bone marrow suppression include the reinfusion of a patient's own previously harvested hematopoietic stem and progenitor cells. In such procedures, patients undergo successive treatments with cell mobilization agents to cause mobilization of hematopoietic progenitor cells from the bone marrow to the peripheral circulation for harvesting. After harvesting, the patient is given high dose chemotherapy or radiotherapy and the bone marrow function is reconstituted by infusion of the cells harvested earlier.

The use of high-dosage chemotherapy or radiotherapy for bone marrow ablation requires subsequent incorporation of hematopoietic stem cells into the patient, in which case prior harvesting of such cells is required. The success of treatment crucially depends on the mobilization of the bone marrow stem cells, the subsequent return of which permits the patient to achieve reconstitution of a functioning hematopoietic system.

In many cases, successfully mobilization is not effected in the patient and inadequate numbers of hematopoietic stem cells are harvested from these patients using current methods. Further, it is typically necessary to repeat the leukophoresis treatments, particularly if they are unsuccessful. This can be extremely stressful for the patient and the amount of stress increases with the number of repetitions.

SUMMARY OF THE INVENTION

One embodiment is a method for mobilizing peripheral blood precursor cells from bone marrow into peripheral blood by administering to a subject in need of treatment an effective amount of at least one GTPase inhibitor. In one aspect, the peripheral blood precursor cells are hematopoietic cells selected from the group consisting of progenitor cells and stem cells. In a further aspect, the GTPase inhibitor is an inhibitor of Rac GTPase. In one aspect, the Rac GTPase inhibitor is an inhibitor of Rac1 or Rac2. One aspect includes the step of administering an inhibitor of the other Rac GTPase.

One embodiment is a method for mobilizing peripheral blood precursor cells from bone marrow into peripheral blood by administering to a subject in need of treatment an effective amount of at least one GTPase inhibitor and observing an increased mobility of peripheral blood precursor cells in the patient. The method of observing may involve collecting a blood sample and counting the number of peripheral blood precursor cells. In a further embodiment, the method includes collecting mobilized stem cells for identification and/or analysis. In one aspect, the method includes administering a growth factor prior to or concurrently with administering the active agent. The growth factor may be G-CSF, GM-CSF, IL-3, GM-CSF/IL-3 fusion proteins, FLK-2/FLT-3 ligand, stem cell factor, IL-6, IL-11, TPO or combinations thereof. In one aspect, the growth factor is G-CSF.

A further embodiment is a method for facilitating hematopoietic reconstitution of peripheral blood precursor cells in a subject's hematopoietic organs, by: a) administering to the subject an effective amount of at least one active agent capable of inhibiting GTPases in the precursor cells, b) isolating mobilized peripheral blood precursor cells from the peripheral circulation of the subject; and c) infusing the isolated mobilized peripheral blood precursor cells into the subject. In one aspect, the GTPases are Rac GTPases, such as Rac1 or Rac2. In a further aspect both Rac GTPases are administered: Rac1 and Rac2. In one aspect, the peripheral blood precursor cells are hematopoietic cells selected from the group consisting of progenitor cells and stem cells. The method may also include administering a growth factor prior to or concurrently with administering the active agent. The growth factor may be G-CSF, GM-CSF, IL-3, GM-CSF/IL-3 fusion proteins, FLK-2/FLT-3 ligand, stem cell factor, IL-6, IL-11, TPO or combinations thereof. In one aspect, the hematopoietic cells are obtained from peripheral blood. Alternatively, the cells are obtained from bone marrow. In one aspect, the active agent is administered prior to chemotherapy, administered simultaneously with chemotherapy or administered after chemotherapy. The method may further include subsequently treating the subject with a growth factor after infusing the isolated mobilized hematopoietic progenitor cells. In one aspect, the active agent is administered in a series of doses.

One embodiment is a method for obtaining ex vivo expanded cells from a population of peripheral blood precursor cells, by: a) administering to the subject an effective amount of an active agent that is sufficient to cause the peripheral blood precursor cells to mobilize from the hematopoietic organs into the subject's peripheral circulation, wherein the active agent is at least one inhibitor of GTPases; b) isolating mobilized peripheral blood precursor cells from the peripheral circulation of the subject; and c) causing the isolated mobilized peripheral blood precursor cell population to expand to thereby obtain a therapeutically effective level of the cells.

A further embodiment is a method for obtaining a therapeutically effective level of peripheral blood precursor cells, by: a) administering to a subject an effective amount of an active agent that is sufficient to cause the peripheral blood precursor cells to mobilize from the hematopoietic organs into the subject's peripheral circulation, wherein the active agent inhibits at least one GTPase; and b) isolating mobilized peripheral blood precursor cells from the peripheral circulation of the subject to obtain a therapeutically effective level of the cells. In one aspect, the growth factor is administered prior to or concurrently with administering the active agent.

A further embodiment is a method of treating a disease requiring peripheral stem cell transplantation in a subject in need of such treatment, by administering to the subject a hematopoietic stem cell mobilizing-effective amount of at least one active agent consisting of a Rac1 or a Rac2 inhibitor.

One embodiment is a method to enhance the population of progenitor and/or stem cells, in a subject, which method comprises administering to the subject an active agent capable of inhibiting Rac1 and Rac2 GTPases in an amount effective to elevate the progenitor and/or stem cell population in the subject. In one aspect, the subject exhibits a hematopoietic deficit from chemotherapy or radiation therapy. In a further aspect, the subject has a condition selected from the group consisting of aplastic anemia, leukemia and drug-induced anemia. In a further aspect, the subject is a transplantation recipient. Alternatively, the subject can be a healthy stem cell donor. The progenitor and/or stem cells can enhance wound healing, ameliorate bacterial inflammation, and/or restore damaged organ tissue. In one aspect, the compound is administered to the subject by an intravenous or subcutaneous route. In a further aspect, the active compound comprises one or more agents selected from the group consisting of farnesyl protein transferase (FPTase) inhibitor, prenyl-protein transferase inhibitor or geranylgeranyl-protein transferase inhibitor, such as farnesyl protein transferase (FPTase) inhibitor, prenyl-protein transferase inhibitor or geranylgeranyl-protein transferase inhibitor. In a further aspect, the active compound is one or more agents selected from the group consisting of farnesyl protein transferase (FPTase) inhibitor, prenyl-protein transferase inhibitor or geranylgeranyl-protein transferase inhibitor. The method of claim 1, wherein the active compound comprises a toxin selected from the group consisting of toxin A, toxin B, C. sordellii lethal toxin (LT), botulinum toxin, and Staphylococcal toxin EDIN.

A further embodiment is any of the methods above wherein the active compound comprises one or more isolated fusion polypeptides comprising: a) a Rho GAP domain peptide and b) a C-terminus targeting peptide. In one aspect, the Rho GAP domain is a peptide sequence containing the minimum structural domain necessary for Rho GTPase activating protein activity. In a further aspect, the GAP domain is a Rho family GAP selected from the group consisting of p50RhoGAP, p190, p122-RhoGAP, p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8, and their variants. In one aspect, the GAP domain is a polypeptide fragment of a GAP GTPase domain from a GAP protein, wherein the fragment comprises at least 15, 20, 25, 30, 40, 50, 60, 70, 80, 90, 100, 125, 150, 170, 200, 250 or more contiguous amino acids of the amino acid sequence of a GAP protein. In a further aspect, the GAP protein is a Rho family GAP including p50RhoGAP, p190, p122-RhoGAP, p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8, and their variants. In one aspect, the targeting peptide is derived from the C-terminus amino acid sequence of a GTPase. In a further aspect, the targeting peptide is derived from the C-terminus amino acid sequence of a GTPase selected from the group consisting of RhoA, RhoB, RhoC, Cdc42, Rac1, Rac2, Rac3, TC10, RhoG, RhoD, Chp, WRCH1, TCL, and RIF. In a further aspect, the fusion polypeptide comprises a mixture of two fusion polypeptides derived from the C-terminus amino acid sequence of a GTPase consisting of Rac1 and Rac2, respectively. In one aspect, the targeting polypeptide is a peptide fragment wherein the fragment comprises at least 1, 2, 3, 4, 5, 6, 7, 8, 9, 10, 11, 12, 13, 14, 15, 16, 17, 18 or more contiguous amino acids of a sequence selected from the group consisting of the amino acid sequences: SEQ ID NO:14, SEQ ID NO:15, SEQ ID NO:16, SEQ ID NO:17, SEQ ID NO:18, SEQ ID NO:19, SEQ ID NO:20 and fragments thereof. In a further aspect, the targeting polypeptide fragment comprises an amino acid sequence selected from the group consisting of amino acids: SEQ ID NO:14, SEQ ID NO:15, SEQ ID NO:16, SEQ ID NO:17, SEQ ID NO:18, SEQ ID NO:19, SEQ ID NO:20 and fragments thereof. In one aspect, the fusion polypeptide further comprises an N-terminus membrane-translocating peptide. In one aspect, the membrane-translocating peptide is a peptide of about 8 to about 50 residues. In a further aspect, the membrane-translocating peptide is a peptide of about 8 to about 50 residues comprising at least eight consecutive residues of an amino acid sequence selected from the group consisting of: SEQ ID NO:21, SEQ ID NO:22, SEQ ID NO:23, SEQ ID NO:24, SEQ ID NO:25, and fragments thereof. In a further aspect, the membrane-translocating peptide is an amino acid sequence having about 8 to about 24 residues comprising at least eight consecutive residues of an amino acid sequence selected from the group consisting of: SEQ ID NO:21, SEQ ID NO:22, SEQ ID NO:23, SEQ ID NO:24, SEQ ID NO:25, and fragments thereof. In one aspect, the membrane translocation sequence the amino acid sequence is selected from the group consisting of Pro-Thr-Arg-Gln-Gln-Lys-Arg-Pro-Cys-Ser-Leu-Leu (SEQ ID NO:21), Pro-Gln-Pro-Thr-Arg-Gln-Gln-Lys-Arg-Pro-Cys-Ser-Leu-Leu, (SEQ ID NO:22), Gly-Arg-Arg-Arg-Arg-Arg-Arg-Arg-Gly-Thr-Arg-Gln-Gln-Lys-Arg-Pro, (SEQ ID NO:23), Gly-Arg-Arg-Arg-Arg-Arg-Arg-Arg-Gly-Arg-Pro-Arg-Gln-Thr-Gln-Lys, (SEQ ID NO:24), and Gly-Arg-Arg-Arg-Arg-Arg-Arg-Arg-Gly-Thr-Arg-Gln-Gln-Lys-Arg-Pro-Cys-Leu-Leu (SEQ ID NO:25). In a further aspect, the fusion polypeptide comprises at least 15, 20, 30, 40, 50, 60, 70, 80, 90, 100, 125, 150, 175, 200, 250 amino acids (e.g., contiguous amino acids) of an amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13. In a further aspect, the fusion polypeptide comprises an amino acid sequence selected from the group consisting of SEQ ID NO:7, SEQ ID NO:8, SEQ ID NO:9, SEQ ID NO:10, SEQ ID NO:11, SEQ ID NO:12, or SEQ ID NO:13.

Further aspects and advantages of this invention will be disclosed in the following examples, that should be regarded as illustrative and not limiting the scope of this application.

BRIEF DESCRIPTION OF THE DRAWINGS

This invention, as defined in the claims, can be better understood with reference to the following drawings. The drawings are not necessarily to scale, emphasis instead being placed upon clearly illustrating principles of the present invention.

DETAILED DESCRIPTION OF THE PREFERRED EMBODIMENTS

Figure 1:
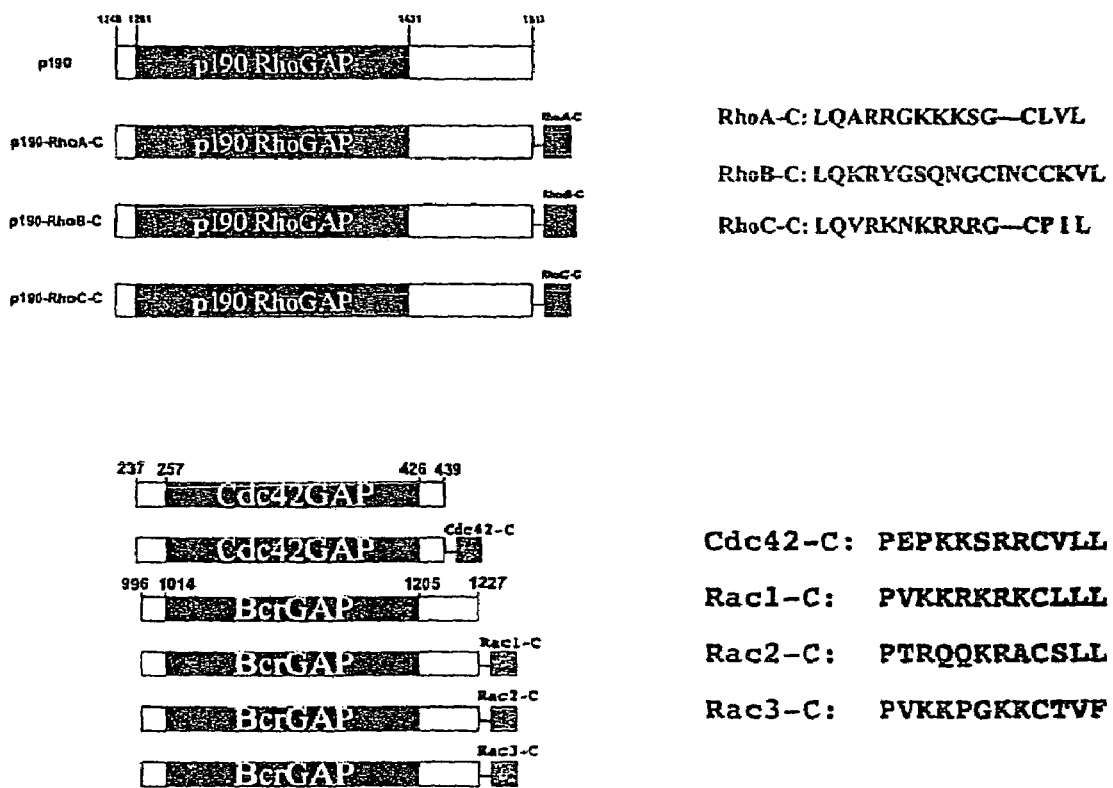
FIG. 1 is a graphical depiction of the fusion peptides between some example GAP domains and various C-terminal intracellular targeting sequences.

The methods and compositions disclosed herein were identified during the search for better methods to increase the number of hematopoeitic cells in a patient. The methods mobilize hematopoietic cells from the bone marrow into the peripheral circulatory system of a patient. This is particularly advantageous for patients requiring the uncomfortable and inconsistently successful method of leukophoresis, for example during a typical myeloablative or myelotoxic therapy. The object of achieving a superior yield of stem cells or a decrease in the number of leukophereses via enhanced mobilization of stem cells, resulted in the following methods and compounds.

The identification of the involvement of GTPases in the mobilization process resulted in a method and compounds which allowed for mobilization by inhibiting GTPases. More particularly, Rac1 and/or Rac2-specific inhibitors can be used for the mobilization of hematopoeitic stem/progenitor cells. This allows the novel use of an active compound to produce a pharmaceutical preparation for enhanced mobilization of hematopoietic stem cells in the treatment of diseases requiring peripheral stem cell transplantation. Diseases requiring peripheral stem cell transplantation include but are not limited to: high-dosage chemotherapy or bone marrow ablation by irradiation. In addition, a pharmaceutical packaging unit is disclosed containing an active compound and informational instructions regarding the application of an active compound or a combination of other agents for enhanced mobilization of hematopoietic stem cells prior to the onset of a corresponding therapy.

Embodiments of the methods and kits allow for increasing white blood cell survival following chemotherapy by administration of at least one GTPase inhibitor. In one embodiment the GTPase inhibitor is at least one Rac1 and/or at least one Rac2 GTPase inhibitor (hereinafter referred to also as "active compounds").

The methods of the preferred embodiments are also particularly suitable for those patients in need of repeated or high doses of chemotherapy. For some cancer patients, hematopoietic toxicity frequently limits the opportunity for chemotherapy dose escalation or completion of prescribed treatments. Repeated or high dose cycles of chemotherapy may be responsible for severe stem cell depletion leading to important long-term hematopoietic sequelea and marrow exhaustion. This may also lead to significant problems in harvesting stem cells. The methods of the present invention provide for improved mortality and blood cell count when used in conjunction with chemotherapy.

A method for mobilizing peripheral blood precursor cells from bone marrow into peripheral blood by administering at least one GTPase inhibitor is disclosed. The method can mobilize peripheral blood precursor cells such as hematopoietic cells like progenitor cells and stem cells. In some embodiments, the method also includes observing an increased mobility of peripheral blood precursor cells in a patient such as by collecting a blood sample and counting the number of peripheral blood precursor cells. In some embodiments, the method can also include collecting mobilized stem cells for identification and/or analysis. In some embodiments, the GTPase inhibitor is at least one inhibitor of Rac GTPases, such as Rac1 or Rac2. In a further embodiment, the inhibitor is an inhibitor of a different Rac GTPase and may be administered in combination with the Rac1 and/or Rac2 GTPase. In one embodiment a Rac1 and a Rac2 GTPase is administered simultaneously or in succession.

In another embodiment, the preferred embodiments are directed to the use of an active compound or a combination of agents, including, e.g., chemotherapeutic agents, to produce a pharmaceutical preparation for enhanced mobilization of hematopoietic stem cells in the treatment of diseases requiring peripheral stem cell transplantation. Preferably, an active compound and the chemotherapeutic agent are formulated in separate administration forms, so that they can be taken out separately and administered successively according to the optimum application regimen. In some embodiments, it is preferred to apply the active compound after the administration of chemotherapeutic agents, during recovery, in order to enhance the mobilization of hematopoietic stem cells.

According to another embodiment, the active compound(s) may be administered prior to the onset of the administration of chemotherapeutic agents in order to enhance the mobilization and collection of hematopoietic stem cells.

Some embodiments also provide for a negative regulatory role of a GAP domain, such as the RhoGAP domain, to specifically downregulate individual Rho protein activity. In particular, p190GAP fused with the RhoA, RhoB, RhoC, Cdc42, Rac1, Rac2 and Rac3 C-terminal sequences are useful for specific downregulation of the respective cellular Rho GTPase activities.

Previous gene targeting studies of RhoB function have shown that distinct from the positive influence on tumor growth or metastasis by RhoA or RhoC, RhoB may act as a negative modifier or suppressor in cancer development, mediating cellular responses to DNA damage or farnesyltransferase inhibitors. Thus, achieving specific targeting of different subtypes of Rho proteins is highly desirable in the treatment of cell proliferation diseases, e.g., tumor cells to reverse the growth and/or invasion phenotypes caused by overexpression of RhoA or RhoC while preserving the tumor suppressor function of RhoB.

The disclosure herein identifies a series of specific GTPase inhibitors which are p190-Rho chimeras that are biochemically active as GAPs for RhoA in vitro and localized to the distinct intracellular locations specified by various Rho family C-terminal sequences. The RhoGAP based approach specifically downregulated the biochemical and biological activity of individual Rho subtypes in cells.

Further embodiments provide methods of importing the biologically active chimeric peptides into intact cells. Such molecules can be engineered by forming a complex by attaching an importation competent signal peptide sequence to a selected biologically active chimeric GAP molecule and administering the complex to the cell. The complex is then imported across the cell membrane by the cell. Thus, methods are disclosed of importing a biologically active molecule into a cell ex vivo or in vivo by administering to the cell, under import conditions, a complex comprising the molecule linked to an importation competent signal peptide, thereby importing the molecule into the cell. In one embodiment, the chimeric GAP polypeptides when linked to a signal peptide and transported into cells, induced a mobilization response in the hematopoietic stem and progenitor cells.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for the purpose of describing and disclosing the cell lines, vectors, and methodologies that are reported in the publications that might be used in connection with the invention. Nothing herein is to be construed as an admission that the invention is not entitled to antedate such disclosure by virtue of prior invention.

Throughout this document, all temperatures are given in degrees Celsius, and all percentages are weight percentages unless otherwise stated. The following are definitions of terms used in this specification. The initial definition provided for a group or term herein applies to that group or term throughout the present specification, individually or as part of another group, unless otherwise indicated. The following definitions, unless otherwise defined, apply:

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include, but are not limited to: buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol;

salt-forming counterions such as sodium; and/or nonionic surfactants such as TWEEN, polyethylene glycol (PEG), and PLURONICS.

As used herein, a "chimeric GAP polypeptide" or "CGP" or "fusion protein" means a polypeptide, or a nucleic acid coding for a chimeric or fusion GAP polypeptide, which polypeptide has a specific binding affinity for a G-proteins (in particular RhoA, RhoB, RhoC, Cdc42, Rac1, Rac2, Rac3, TC10, RhoG, RhoD, Chp, WRCH1, TCL, and RIF). By specific binding affinity, it is meant that the polypeptide has a binding preference for one or more specific G-proteins. Various chimeric GAP peptide fusion products are shown graphically in FIG. 1.

A "chimeric gene" refers to a sequence of DNA in which nucleotide sequences not naturally occurring together are linked. As used to describe this aspect of the invention, the term "chimeric" requires that the amino acid sequence of the chimeric molecule include at least one stretch of amino acids (preferably stretches of 50-300, or more amino acids) from the naturally-occurring polypeptide from which it was derived. Thus, the chimeric polypeptide is a "hybrid" or "mosaic" of two or more polypeptides. By "chimeric" is meant that the polypeptide of the invention is not identical to any naturally occurring polypeptide sequence (or fragment of a natural polypeptide sequence).

The term "cytotoxic agent" as used herein refers to a substance that inhibits or prevents the function of cells and/or causes destruction of cells. The term is intended to include radioactive isotopes, chemotherapeutic agents, and toxins such as enzymatically active toxins of bacterial, fungal, plant or animal origin, or fragments thereof.

An "effective amount" or "therapeutically effective amount" of an active agent disclosed herein is an amount capable of modulating, to some extent, the mobilization of hematopoietic cells. A "therapeutically effective amount", in reference to the mobilization of hematopoietic cells, refers to an amount capable of invoking one or more of the following effects: (1) elevate the number of progenitor and/or stem cell population in said subject; (2) mobilize peripheral blood precursor cells from hematopoietic organs into the mammal's peripheral circulation; (3) mobilizing stem cells in sufficient amounts to achieve a desired physiological effect; (4) facilitate hematopoietic reconstitution; (5) induces the release and mobilization of hematopoietic cells; (6) sufficiently modulate the activity of Rac1 and/Rac2 in hematopoietic cells; or (7) treatment and/or relief, to some extent, of one or more symptoms associated with a stem cell disorder. An "effective amount" may be determined empirically and in a routine manner.

The term "encoding" refers generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence that promotes expression of the sense strand. The information is convertible using the standard, or a modified, genetic code. See, e.g., Watson et al., (1987) The Molecular Biology of the Gene (4th ed.) vols. 1&2, Benjamin, Menlo Park, Calif.

A "Rho GTPase" is a small, Ras-related GTP-binding protein that functions by binding and hydrolyzing GTP. The activated form of Rho GTPase is typically membrane-bound. Rho GTPases function as molecular switches, cycling between an inactive GDP-bound conformation and an active GTP-bound conformation and include RhoA, RhoB, RhoC, Cdc42, Rac1, Rac2, Rac3, TC10, RhoG, RhoD, Chp, WRCH1, TCL, and RIF. The terms "RhoGTPase" or "Rho GTPase protein polypeptide" refer to a protein or polypeptide sequence of a Ras-related GTP-binding protein, variants or fragments thereof obtained from any species, particularly mammalian, including bovine, ovine, porcine, murine, equine, and preferably human, from any source whether natural, synthetic, semi-synthetic, or recombinant.

A key group of regulatory molecules for the Rho GTPases is the Rho GTPase-activating proteins (GAPs). Rho GAPs preferentially recognize the GTP-bound form of a Rho GTPase and stimulate the intrinsic GTPase activity to hydrolyze the bound GTP to GDP. Rho GAPs therefore function as negative regulators or suppressors of Rho GTPase by stimulating the conversion of the Rho GTPase from the active GTP-bound form to the inactive GDP-bound form.

The term "GTPase activating protein" or "GAP", as used herein, refers to the amino acid sequences of GTPase activating proteins obtained from any species, particularly mammalian, including bovine, ovine, porcine, murine, equine, and preferably human, from any source whether natural, synthetic, semi-synthetic, or recombinant. "GAPs" refers to more than one GAP. Generally, Rho GAP proteins share an approximately 170-190 amino acid homology region, designated as the Rho GAP domain, that contains the minimum structural domain necessary for GAP activity. Rho GAP proteins share 20-24% amino acid identity in this domain, however, certain specific residues are highly conserved.

A number of GAPs that are active on proteins of the Rho family have been identified (reviewed in Lamarche and Hall, TIG 10:436-440, 1994). These include p50RhoGAP (Lancaster et al., J. Biol. Chem. 269:1137-1142, 1994), Myr5 (Reinhard et al., EMBO J. 14:697-704, 1995), and p190 (Settleman et al., Nature 359:153-154, 1992) that are also active on Rac and Cdc42. Another GAP, p122-RhoGAP (Homma and Emori, EMBO J. 14:286-291, 1995) appears to be specific for Rho. In addition, rhoGAPs include p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8,and their variants (Moon, S. Y. and Zheng, Y. (2003) Rho GTPase-activating proteins in cell regulation, *Trends Cell Biol.* 13, 14-23. Peck, J., Douglas, G., Wu, C. H., and Burbelo, P. D. (2002) Human RhoGAP domain-containing proteins: structure, function and evolution relationship. *FEBS Letters* 528, 27-34).

The terms "GAP polypeptide" and "GAP" as used herein and when immediately followed by a numerical designation refer to various polypeptides, wherein the complete designation (i.e., GAP/number) refers to specific polypeptide sequences as described herein. The terms "GAP/number polypeptide" and "GAP/number" wherein the term "number" is provided as an actual numerical designation as used herein encompass native sequence polypeptides and polypeptide variants (that are further defined herein). The GAP polypeptides described herein may be isolated from a variety of sources, such as from human tissue types or from another source, or prepared by recombinant or synthetic methods. The term "GAP polypeptide" refers to each individual GAP/number polypeptide disclosed herein. All disclosures in this specification which refer to the "GAP polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention-individually. The term "GAP polypeptide" also includes variants of the GAP/number polypeptides disclosed herein.

"GAP polypeptide variant" means an active GAP polypeptide as defined above or below having at least about 80% amino acid sequence identity with a full-length native sequence GAP polypeptide sequence as disclosed herein (e.g., SEQ ID NO:2; SEQ ID NO:4; SEQ ID NO:6), a GAP polypeptide sequence lacking the signal peptide as disclosed herein, an extracellular domain of a GAP polypeptide, with or without the signal peptide, as disclosed herein or any other fragment of a full-length GAP polypeptide sequence as disclosed herein. Such GAP polypeptide variants include, for instance, GAP polypeptides wherein one or more amino acid residues are added, or deleted, at the N- or C-terminus of the full-length native amino acid sequence. Ordinarily, a GAP polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a fill-length native sequence GAP polypeptide sequence as disclosed herein, a GAP polypeptide sequence lacking the signal peptide as disclosed herein, an extracellular domain of a GAP polypeptide, with or without the signal peptide, as disclosed herein or any other specifically defined fragment of a full-length GAP polypeptide sequence as disclosed herein. Ordinarily, GAP variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

As used interchangeably herein, a "GAP activity", "biological activity of GAP," or "functional activity of GAP," includes at least one activity exerted by a GAP protein, polypeptide or nucleic acid molecule on a GAP-responsive cell or tissue, or on a GAP protein substrate, as determined in vivo, or in vitro, according to standard techniques. In one embodiment, a GAP activity is a direct activity, such as an association with a GAP-target molecule. As used herein, a "target molecule" or "binding partner" is a molecule with which a GAP protein binds or interacts in nature, such that GAP-mediated function is achieved. A GAP target molecule can be a non-GAP molecule or a GAP protein or polypeptide of the present invention. In an exemplary embodiment, a GAP target molecule is a GAP ligand, e.g., a GTPase. Alternatively, a GAP activity is an indirect activity, such as a cellular signaling activity mediated by interaction of the GAP protein with a GAP ligand, e.g., a GTPase. Preferably, a GAP activity is the ability to modulate the hydrolysis of GTP via, e.g., interactions with GTPase molecules.

In another embodiment, a chimeric GAP molecule of the present invention is identified based on the presence of a "RhoGAP domain" in the protein or corresponding nucleic acid molecule. As used herein, the term "RhoGAP domain" includes a protein domain having an amino acid sequence of about 150 amino acid residues. Preferably, a RhoGAP domain includes at least about 120-265, more preferably about 140-205 amino acid residues, or about 145-175 amino acids. In another preferred embodiment, a RhoGAP domain has at least about 40%, 50%, 60%, 70% 80% 90% 95%, 97%, 98%, 99%, or 100% sequence identity with a RhoGAP domain of human p190 GAP (e.g., residues 1261-1431 of SEQ ID NO:2).

In another embodiment, a chimeric GAP molecule of the present invention is identified based on the presence of a "Cdc42GAP domain" in the protein or corresponding nucleic acid molecule. As used herein, the term "Cdc42GAP domain" includes a protein domain having an amino acid sequence of about 150 amino acid residues. Preferably, a Cdc42GAP domain includes at least about 120-265, more preferably about 140-205 amino acid residues, or about 145-175 amino acids. In another preferred embodiment, a Cdc42GAP domain has at least about 40%, 50%, 60%, 70% 80% 90% 95%, 97%, 98%, 99%, or 100% sequence identity with a Cdc42GAP domain of human or rat Cdc42GAP (e.g., residues 257-426 of SEQ ID NO:4).

In another embodiment, a chimeric GAP molecule of the present invention is identified based on the presence of a "BcrGAP domain" in the protein or corresponding nucleic acid molecule. As used herein, the term "BcrGAP domain" includes a protein domain having an amino acid sequence of about 150 amino acid residues. Preferably, a BcrGAP domain includes at least about 120-265, more preferably about 140-235 amino acid residues, or about 145-195 amino acids. In another preferred embodiment, a BcrGAP domain has at least about 40%, 50%, 60%, 70% 80% 90% 95%, 97%, 98%, 99%, or 100% sequence identity with a BcrGAP domain of human or rat BcrGAP (e.g., residues 1014-1205 of SEQ ID NO:6).

"GAP polynucleotide" or "GAP nucleic acid sequence" means a nucleic acid molecule which encodes an active GAP polypeptide as defined herein and which has at least about 80% nucleic acid sequence identity with a nucleotide acid sequence encoding a full-length native sequence GAP polypeptide sequence as disclosed herein, a full-length native sequence GAP polypeptide sequence lacking the signal peptide as disclosed herein, an extracellular domain of a GAP polypeptide, with or without the signal peptide, as disclosed herein or any other fragment of a full-length GAP polypeptide sequence as disclosed herein. Ordinarily, a GAP variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence GAP polypeptide sequence as disclosed herein, a full-length native sequence GAP polypeptide sequence or any other fragment of a full-length GAP polypeptide sequence as disclosed herein (e.g., SEQ ID NO:1; SEQ ID NO:3; SEQ ID NO:5),. Variants do not encompass the native nucleotide sequence.

A "gene fusion" is a DNA construction (performed in vitro or in vivo) that results in the coding sequences from one gene (the "responder") being transcribed and/or translated under the direction of the controlling sequences of another gene (the "controller"). Responder genes can be divided into two classes, reporters and effectors, with analytical Or manipulative roles, respectively.

A "host cell" is a cell that has been transformed, or is capable of transformation, by an exogenous DNA sequence.

The term "hybridization", as used herein, refers to any process by which a strand of nucleic acid binds with a complementary strand through base pairing.

Administration "in combination with" one or more additional therapeutic agents includes simultaneous (concurrent) and consecutive administration in any order.

An "isolated" nucleic acid is a nucleic acid, e.g., an RNA, DNA, or a mixed polymer, which is substantially separated from other DNA sequences which naturally accompany a native human sequence, e.g., ribosomes, polymerases, and many other human genome sequences. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. An isolated nucleic acid will generally be a homogenous composition of molecules, but will, in some embodiments, contain minor heterogeneity. This heterogeneity is typically found at the polymer ends or portions not critical to a desired biological function or activity.

"Isolated," when used to describe the various polypeptides disclosed herein, means polypeptide that has been identified and separated and/or recovered from at least one component of its natural environment. Preferably, the isolated polypeptide is free of association with substantially all contaminant components with which it is naturally associated and that substantially interfere with its activity. Contaminant components of its natural environment are materials that would typically interfere with diagnostic or therapeutic uses for the polypeptide, and can include enzymes, hormones, and other proteinaceous or non-proteinaceous solutes.

A "liposome" is a small vesicle composed of various types of lipids, phospholipids and/or surfactant that is useful for delivery of a drug (such as a GAP polypeptide) to a mammal. The components of the liposome are commonly arranged in a bilayer "Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

A "native sequence GAP polypeptide" comprises a polypeptide having the same amino acid sequence as the corresponding GAP polypeptide derived from nature. Such native sequence GAP polypeptides can be isolated from nature or can be produced by recombinant or synthetic means. The term "native sequence GAP polypeptide" specifically encompasses naturally-occurring truncated or secreted forms of the specific GAP polypeptide (e.g., an extracellular domain sequence), naturally-occurring variant forms (e.g., alternatively spliced forms) and naturally-occurring allelic variants of the polypeptide. In various embodiments of the invention, the native sequence GAP polypeptides disclosed herein are mature or full-length native sequence polypeptides comprising the full-length amino acids sequences shown in the accompanying figures. Start and stop codons are shown in bold font and underlined in the figures. However, while the GAP polypeptide disclosed in the accompanying figures are shown to begin with methionine residues designated herein as amino acid position 1 in the figures, it is conceivable and possible that other methionine residues located either upstream or downstream from the amino acid position 1 in the figures can be employed as the starting amino acid residue for the GAP polypeptides.

"Nucleic acid sequence" as used herein refers to an oligonucleotide, nucleotide, or polynucleotide, and fragments or portions thereof, and to DNA or RNA of genomic or synthetic origin that can be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

"Oligonucleotides" refers to either a single stranded polydeoxynucleotide or two complementary polydeoxynucleotide strands, that can be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to the GAP polypeptide sequences identified herein is defined as the percentage of amino acid residues in a candidate sequence that are identical with the amino acid residues in the specific GAP polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST software. Those skilled in the art can determine appropriate parameters for measuring alignment, including any algorithms needed to achieve maximal alignment over the full length of the sequences being compared.

The term "polypeptide" refers to a polymer of amino acids and its equivalent and does not refer to a specific length of the product; thus, peptides, oligopeptides and proteins are included within the definition of a polypeptide. This term also does not exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring.

A "polypeptide variant" of any one of the polypeptides will have at least about 80% amino acid sequence identity, preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and most preferably at least about 99% amino acid sequence identity with a full-length native sequence as disclosed herein, such variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 300 amino acids in length, or more.

The term "portion", as used herein, with regard to a protein (as in "a portion of a given protein") refers to fragments of that protein. The fragments can range in size from four amino acid residues to the entire amino acid sequence minus one amino acid.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase.

The term "protein" is used herein to designate a naturally occurring polypeptide. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like. "Native" proteins or polypeptides refer to proteins or polypeptides recovered from a source occurring in nature.

"Percent (%) nucleic acid sequence identity" with respect to GAP domain and GTPase tail-encoding nucleic acid sequences identified herein is defined as the percentage of nucleotides in a candidate sequence that are identical with the nucleotides in the nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST software.

The term "recombinant" refers to a nucleic acid sequence, that is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features can be incorporated by design. A similar concept is intended for a recombinant, e.g., fusion, polypeptide. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so.

The term "signal peptide" refers to any peptide sequence that directs a polypeptide to which it is attached to a target cell and, preferably, directs its transport across the cell membrane. An "importation competent signal peptide sequence" is one that remains competent to translocate the attached peptide sequence across a cellular membrane.

The term "stringent conditions", as used herein, is the "stringency" that occurs within a range from about Tm−5° C. (5° C. below the melting temperature (Tm) of the probe) to about 20° C. to 25° C. below Tm. As will be understood by those of skill in the art, the stringency of hybridization can be altered in order to identify or detect identical or related polynucleotide sequences. As known in the art, numerous equivalent conditions can be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution can be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA can be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cell containing the exogenous DNA.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Specifically, treatment refers to the mobilization of hematopoietic cells by contacting cells with an effective amount of an appropriate Rac1 and or Rac2 inhibitor.

A "variant" as used herein, refers to an amino acid sequence that is altered by one or more amino acids. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which amino acid residues can be substituted, inserted, or deleted without abolishing biological or immunological activity can be found using computer programs well known in the art, for example, DNASTAR software.

A "vector" is a replicon, such as a plasmid, phage, or cosmid, to which another DNA segment can be attached so as to bring about the replication of the attached segment.

Mobilization of Hematopoietic Cells

The disclosure provides for a GTPase inhibitor and a method of mobilizing hematopoietic progenitor cells. In one embodiment the GTPase inhibitor is a Rac1 or a Rac2-specific inhibitor. The method disclosed herein relates to the novel use of an active compound or a combination of chemotherapeutic agents to produce a pharmaceutical preparation for enhanced mobilization of hematopoietic stem cells in the treatment of diseases requiring stem cell transplantation as is the case, e.g., in high-dosage chemotherapy or bone marrow ablation by irradiation. In addition, the invention is directed to a pharmaceutical packaging unit containing an active compound, chemotherapeutic agent(s) and informational instructions regarding the application of the an active compound and the chemotherapeutic agent or the combination of chemotherapeutic agents for enhanced mobilization of hematopoietic stem cells prior to the onset of a corresponding therapy.

The inhibitors may be any GTPase inhibitors known to one of skill in the art, including, but not limited to: proteins, peptides, antibodies, nucleic acids, and small molecules. In one aspect, the present invention provides methods and kits for increasing progenitor and stem cell survival and mobilization following chemotherapy by administration of Rac1 and Rac2 GTPase inhibitors (GTPase inhibitors hereinafter referred to as "active compounds").

In another aspect, methods and kits are provided for mobilizing hematopoietic stem and progenitor cells from bone marrow into peripheral blood comprising the administration of the active compounds of the invention to a patient in need of such treatment. The harvested stem cells can subsequently be used to treat a patient in need of chemotherapy.

The methods are also particularly suitable for those patients in need of repeated or high doses of chemotherapy. For some cancer patients, hematopoietic toxicity frequently limits the opportunity for chemotherapy dose escalation or completion of prescribed chemotherapy. Repeated or high dose cycles of chemotherapy can be responsible for severe stem cell depletion leading to important long-term hematopoietic sequelea and marrow exhaustion. The methods of the present invention provide for improved mortality and blood cell count when used in conjunction with chemotherapy.

In another embodiment, the use of an active compound and a chemotherapeutic agent or a combination of chemotherapeutic agents is provided to produce a pharmaceutical preparation for enhanced mobilization of hematopoietic stem cells in the treatment of diseases requiring stem cell transplantation. The active compound and the chemotherapeutic agent can be present formulated in separate administration forms, so that they can be taken out separately and administered successively according to the optimum application regimen. It is preferred to apply the active compound prior to the onset of the administration of chemotherapeutic agents in order to enhance the mobilization of hematopoietic stem cells.

The combined use according to the invention of an active compound and chemotherapeutic agent relates to all those diseases requiring recovery of stem cells from the blood for subsequent peripheral transplantation, particularly tumor diseases.

Further aspects and advantages will be disclosed in the following examples, that should be regarded as illustrative and not limiting the scope of this application.

The term "active compounds" refers to any compound or combination of compounds capable of selectively inhibiting both Rac1 and Rac2 GTPases. Alternatively, the active compound could comprise two or more compounds that specifically inhibit rac1 or rac2 or both.

Farnesyl Protein Transferase (FPTase)

In one embodiment, the active compound comprises one or more inhibitor of farnesyl protein transferase (FPTase), prenyl-protein transferase or geranylgeranyl-protein transferase as described in U.S. Pat. Nos. 6,572,850; 6,458,783; 6,423, 751; 6,387,926; 6,242,433; 6,191,147; 6,166,067; 6,156,746; 6,083,979; 6,011,029; 5,929,077; 5,928,924; 5,843,941; 5,786,193; 5,629,302; 5,618,964; 5,574,025; 5,567,841; 5,523,430; 5,510,510; 5,470,832; 5,447,922, 6,596,735; 6,586,461; 6,586,447; 6,579,887; 6,576,639; 6,545,020; 6,539,309; 6,535,820; 6,528,523; 6,511,800; 6,500,841; 6,495,564; 6,492,381; 6,458,935; 6,451,812; 6,441,017; 6,440,989; 6,440,974; 6,432,959; 6,426,352; 6,410,541; 6,403,581; 6,399,615; 6,387,948; 6,387,905; 6,387,903; 6,376,496; 6,372,747; 6,362,188; 6,358,968; 6,329,376; 6,316,462; 6,294,552; 6,277,854; 6,268,394; 6,265,382; 6,262,110; 6,258,824; 6,248,756; 6,242,458; 6,239,140; 6,228,865; 6,228,856; 6,225,322; 6,218,401; 6,214,828; 6,214,827; 6,211,193; 6,194,438, that are specifically incorporated herein by reference in their entirety.

A "Rac1 inhibitor" and "Rac2 inhibitor" is defined herein as an agent that blocks the activity of any protein in the Rho GTPase signal transduction pathway. A particularly preferred Rac1 and Rac2 inhibitor is a "farnesyl protein transferase inhibitor."

A "farnesyl protein transferase inhibitor" or "FPT inhibitor" or "FTI" is defined herein as a compound that: (i) potently inhibits FPT (but generally not geranylgeranyl protein transferase I) and (ii) blocks intracellular farnesylation of Ras. FPT catalyzes the addition of an isoprenyl lipid moiety onto a cysteine residue present near the carboxy-terminus of the Ras protein. This is the first step in a post-translational processing pathway that is essential for both Ras membrane-association and Ras-induced oncogenic transformation. A number of FPT inhibitors have been reported, including a variety of peptidomimetic inhibitors as well as other small molecule inhibitors.

Farnesyl transferase inhibitors generally fall into two classes: analogs of farnesyl diphosphate; and protein substrates for farnesyl transferase. Farnesyl transferase inhibitors have been described in U.S. Pat. No. 5,756,528, U.S. Pat. No. 5,141,851, U.S. Pat. No. 5,817,678, U.S. Pat. No. 5,830,868, U.S. Pat. No. 5,834,434, and U.S. Pat. No. 5,773,455, incorporated herein by reference. Among the farnesyl transferase inhibitors shown to be effective for inhibiting the transfer of the farnesyl moiety to Ras-related proteins are L-739,749 (a peptidomimetic analog of the C-A-A-X sequence), L-744, 832 (a peptidomimetic analog of the C-A-A-X sequence), SCH 44342(1-(4-pyridylacetyl)-4-(8-chloro-5,6 dihydro-IIH benzo[5,6]cyclohepta[1,2-b]pyridin-11-yhdene)piperidine), BZA-5B (a benzodiazepine peptidomimetic), FTI-276 (a C-A-A-X peptidomimetic), and B1086 (a C-A-A-X peptidomimetic). Administration of farnesyl transferase inhibitors (FTIs) is accomplished by standard methods known to those of skill in the art, most preferably by administration of tablets containing the FTI, and is expected to fall approximately within a range of about 0.1 mg/kg of body to weight to about 20 mg/kg of body weight per day.

However, classes of compounds that can be used as the FPT inhibitor include: fused-ringed tricyclic benzocycloheptapyridines, oligopeptides, peptido-mimetic compounds, farnesylated peptido-mimetic compounds, carbonyl piperazinyl compounds, carbonyl piperidinyl compounds, farnesyl derivatives, and natural products and derivatives.

Examples of compounds that are FPT inhibitors and the documents directed to those compounds are given below.

Fused-ring tricyclic benzocycloheptapyridines: WO 95/10514; WO 95/10515; WO 95/10516; WO 96/30363; WO 96/30018; WO 96/30017; WO 96/30362; WO 96/31111; WO 96/31478; WO 96/31477; WO 96/31505; WO 97/23478; International Patent Application No. PCT/US97/17314 (WO 98/15556); International Patent Application No. PCT/US97/15899 (WO 98/11092); International Patent Application No. PCT/US97/15900 (WO 98/11096); International Patent Application No. PCT/US97/15801 (WO 98/11106); International Patent Application No. PCT/US97/15902 (WO 98/11097); International Patent Application No. PCT/US97/15903 (WO 98/11098); International Patent Application No. PCT/US97/15904; International Patent Application No. PCT/US97/15905 (WO 98/11099); International Patent Application No. PCT/US97/15906 (WO 98/11100); International Patent Application No. PCT/US97/15907 (WO 98/11093); International Patent Application No. PCT/US97/19976 (WO 98/11091); U.S. application Ser. No. 08/877,049: U.S. application Ser. No. 08/877,366; U.S. application Ser. No. 08/877,399; U.S. application Ser. No. 08/877,336; U.S application Ser. No. 08/877,269; U.S. application Ser. No. 08/877,050; U.S application Ser. No. 08/877,052; U.S application Ser. No. 08/877,051; U.S. application Ser. No. 08/877, 498; U.S application Ser. No. 08/877,057; U.S application Ser. No. 08/877,739; U.S. application Ser. No. 08/877,677; U.S application Ser. No. 08/877,741; U.S application Ser. No. 08/877,743; U.S. application Ser. No. 08/877,457; U.S application Ser. No. 08/877,673; U.S application Ser. No. 08/876, 507; and U.S. application Ser. No. 09/216,398.

Some FPT inhibitors are oligopeptides, especially tetrapeptides, or derivatives thereof, based on the formula Cys-Xaa1-Xaa2-Xaa3, where Xaa3 represents a serine, methionine or glutamine residue, and Xaa1 and Xaa2 can represent a wide variety of amino acid residues, but especially those with an aliphatic side-chain. Their derivatives may or may not have three peptide bonds; thus it has been found that reduction of a peptide bond —CO—NH— to a secondary amine grouping, or even replacement of the nitrogen atoms in the peptide chain with carbon atoms (provided that certain factors such as general shape of the molecule and separation of the ends are largely conserved) affords compounds that are frequently more stable than the oligopeptides and, if active, have longer activity. Such compounds are referred to herein as peptidomimetic compounds and include, but are not limited by the following:Oligopeptides (mostly tetrapeptides but also pentapeptides) including the formula Cys-Xaa1-Xaa2-Xaa3: EPA 461,489; EPA 520,823; EPA 528,486; and WO 95/11917. Peptido-mimetic compounds—especially Cys-Xaa-Xaa-Xaa-mimetics: EPA 535,730; EPA 535,731; EPA 618,221; WO 94/09766; WO 94/10138; WO 94/07966; U.S. Pat. No. 5,326,773; U.S. Pat. No. 5,340,828; U.S. Pat. No. 5,420,245; WO 95/20396; U.S. Pat. No. 5,439,918; and WO 95/20396. Farnesylated peptido-mimetic compounds—specifically farnesylated Cys-Xaa-Xaa-Xaa-mimetic: GB-A 2,276,618. Other peptido-mimetic compounds: U.S. Pat. No. 5,352,705; WO 94/00419; WO 95/00497; WO 95/09000; WO 95/09001; WO 95/12612; WO 95/25086; EPA 675,112; and FR-A 2,718,149. Farnesyl derivatives: EPA 534,546; WO 94/19357; WO 95/08546; EPA 537,007; and WO 95/13059. Natural products and derivatives: WO 94/18157; U.S. Pat. No. 5,430,055; GB-A 2,261,373; GB-A 2,261,374; GB-A 2,261,375; U.S. Pat. No. 5,420,334; U.S. Pat. No. 5,436,263.

Other compounds: WO 94/26723; WO 95/08542; U.S. Pat. No. 5,420,157; WO 95/21815; WO 96/31501; WO 97/16443; WO 97/21701; U.S. Pat. No. 5,578,629; U.S. Pat. No. 5,627, 202; WO 96/39137; WO 97/18813; WO 97/27752WO 97/27852; WO 97/27853; WO 97/27854; WO 97/36587; WO 97/36901; WO 97/36900; WO 97/36898; WO 97/36897; WO 97/36896; WO 97/36892; WO 97/36891; WO 97/36890; WO 97/36889; WO 97/36888; WO 97/36886; WO 97/36881; WO 97/36879; WO 97/36877; WO 97/36876; WO 97/36875; WO 97/36605; WO 97/36593; WO 97/36592; WO 97/36591; WO 97/36585; WO 97/36584; and WO 97/36583. A plasmid encoding an α- and a β-unit of an FPT, and describing an assay therefor: WO 94/10184.

Reference is also made to U.S application Ser. No. 09/217, 335 and International Patent Application No. PCT/US98/26224, that disclose a variety of methods for combining FPT inhibitors with chemotherapeutic agents and/or radiation therapy in the treatment of proliferative disease such as cancer.

All of the foregoing documents directed to compounds that are FPT inhibitors are incorporated herein by reference thereto. Graham, in Exp. Opin. Ther. Patents (1995) 5(12): 1269-1285, gives a review of many such compounds.

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Inhibition of farnesyl pyrophosphate biosynthesis by inhibiting HMG-CoA reductase blocks Ras membrane localization in cultured cells.

Another inhibitor of Rac is S-farnesylthiosalicylic Acid (FTS) and its derivatives and analogs. Another inhibitor is imidazole-containing benzodiazepines and analogs (WO-97/30992).

Several groups of scientists have recently disclosed compounds that are non-selective FPTase/GGTase inhibitors. (Nagasu et al. Cancer Research, 55:5310-5314 (1995); PCT application WO 95/25086). Recently, synergy between certain modulating anions and farnesyl-diphosphate competitive inhibitors of FPTase has been disclosed (J. D. Scholten et al. J. Biol. Chem. 272:18077-18081 (1997)). The modulating anion can be selected from any type of molecule containing an anion moiety. Preferably the modulating anion is selected from a phosphate or sulfate containing anion. Particular examples of modulating anions useful in the instant GGTase-I inhibition assay include adenosine 5'-triposphate (ATP), 2'-deoxyadenosine 5'-triphosphate (dATP), 2'-deoxycytosine 5'-triphosphate (dCTP), beta-glycerol phosphate, pyrophosphate, guanosine 5'-triphosphate (GTP), 2'-deoxyguanosine 5'-triphosphate (dGTP), uridine 5'-triphosphate, dithiophosphate, 3'-deoxythymidine 5'-triphosphate, tripolyphosphate, D-myo-inositol 1,4,5-triphosphate, chloride, guanosine 5'-monophosphate, 2'-deoxyguanosine 5'-monophosphate, orthophosphate, formycin A, inosine diphosphate, trimetaphosphate, sulfate and the like. Preferably, the modulating anion is selected from adenosine 5'-triphosphate, 2'-deoxyadenosine 5'-triphosphate, 2'-deoxycytosine 5'-triphosphate, beta-glycerol phosphate, pyrophosphate, guanosine 5'-triphosphate, 2'-deoxyguanosine 5'-triphosphate, uridine 5'-triphosphate, dithiophosphate, 3'-deoxythymidine 5'-triphosphate, tripolyphosphate, D-myo-inositol 1,4,5-triphosphate and sulfate. Most preferably, the modulating anion is selected from adenosine 5'-triphosphate, β-glycerol phosphate, pyrophosphate, dithiophosphate and sulfate.

Inhibitors of geranylgeranyl-protein transferase (GGT) have been described in U.S. Pat. No. 5,470,832 (Gibbs & Graham). These compounds can be administered to an individual in dosage amounts of between 0.5 mg/kg of body weight to about 20 mg/kg of body weight. Alternatively, one or more inhibitors of isoprenylation, including farnesyl transferase (FT) inhibitors and/or geranylgeranyl transferase inhibitors (GGT) are administered to a patient.

Toxins

Toxins can also be used such as Toxins A and B from C. difficile and C. sordellii lethal toxin (LT). In addition, Rac1 and/or Rac2 can be inhibited when Rho is specifically ADP ribosylated by C3 enzyme, that is one of the botulinum toxins, and Staphylococcal toxin EDIN (Narumiya, S. and Morii, S., Cell Signal, 5, 9-19, 1993; Sekine, A. et al., J. Biol. Chem., 264, 8602-8605, 1989).

Antisense

In one aspect, the inhibitor formulation can employ antisense compounds, particularly oligonucleotides, for use in modulating the function of nucleic acid molecules encoding rac1 and rac2, ultimately modulating the amount of rac produced. This is accomplished by providing oligonucleotides that specifically hybridize with nucleic acids, preferably mRNA, encoding rac1 and rac2, e.g., as described in U.S. Pat. No. 6,410,323.

Small Molecule Inhibitors

Small molecule inhibitors may be used to inhibit the GTPases as disclosed herein. Any type of small molecule inhibitor which is known to one of skill in the art may be used, including but not limited to, those disclosed is U.S. Provisional application 60/523,599 (GTPase inhibitors and Methods of Use), Nov. 20, 2003, herein incorporated by reference in its entirety. Many methods are know to identify small molecule inhibitors and commercial laboratories are available to screen for inhibitors. In addition to the method disclosed in Provisional patent application 60/523,599 (GTPase Inhibitors and methods of Use), robotic screening assays are available which look at the ability of small molecules to inhibit the GTPase activity of choice in an appropriate assay. For example, chemicals can be obtained from the compound collection at Merck Research Laboratories (Rahway, N.J.) or a like company. The compounds can be screened for inhibition of a specific GTPase by automated robotic screeing in a 96-well plate format. In summary, the compounds can be dissolved at an initial concentration of about 50 μM in DMSO and dispensed into the 96-well plate. The 96-well plate assay may contain an appropriate number of units of the GTPase of choice and a substrate. Compounds that cause greater than a 50% inhibition of GTPase activity can be further diluted and tested to establish the concentration necessary for a 50% inhibition of activity.

The Rho family Guanosine Triphosphatases (GTPases), Rac1 and Rac2, are important signaling regulators in hematopoietic cells. Inhibition of both Rac1 and Rac2 alleles leads to massive mobilization of hematopoietic stem/progenitor cells (HSC/P) whereas inhibition of Rac1, but not Rac2, HSC/P fail to reconstitute irradiated recipient mice. In HSC/P, Rac1 controls proliferation via p42/p44 MAPKs, Cyclin D1 and p27. In contrast, in neutrophils Rac2, but not Rac1, regulates superoxide production and cell migration. In both cell types, each GTPase plays a distinct role in organizing actin. Thus, inhibition of Rac1 and Rac2 is allows for the mobilization of hematopoietic cells.

In one aspect, therefore, the invention is directed to a method to elevate the progenitor cells and/or stem cells, in a subject, which method comprises administering to said subject an amount of an active compound effective to elevate progenitor cell and/or stem cell levels. In one embodiment, bone marrow progenitor and/or stem cells are mobilized for myocardial repair.

Methods for Mobilization

Methods are provided to induce mobilization of peripheral blood precursor cells, to elevate circulating levels of peripheral blood precursor cells, or to enhance or facilitate hematopoietic reconstitution or engraftment, in mammals, including humans. "Peripheral blood precursor cells", as used herein, include stem cells, that are pluripotent, and early progenitor cells, that are more differentiated than stem cells. In one embodiment of the current invention, mobilization of peripheral blood precursor cells in a mammal is induced by administering to the mammal an effective amount of an active compound.

The method of mobilizing progenitor cells can be used for mobilization of stem/progenitor cells in patients who will undergo cytoreductive therapy, such as chemotherapy or radiation therapy. After mobilization, the stem/progenitor cells are collected from the peripheral blood and either stored, or expanded in culture. The method of mobilizing progenitor cells can also be used for mobilization of stem/progenitor cells in individuals who will serve as allogenic donors of progenitor cells. Other diseases and disorders for which the active compound is beneficial in addition to those already described are leukopenia of various origins including, congenital leukopenia, childhood or adult cyclic neutropenia, post-infective neutropenia, and myelodysplastic syndrome. In addition, the active compound can be used for patients who are "difficult to mobilize" because, for example, they are not sensitive to growth factors. The methods can further be used to cause tolerance of a recipient for organ transplantation.

The methods can additionally be used for gene therapy. Because pluripotent stem cells are self-renewing, and give rise to cell progenitors as well as mature blood cells, the stem cells are an appropriate target for gene therapy. After mobilization, stem/progenitor cells can be collected. The stem/progenitor cells can be modified to deliver gene products upon reintroduction to the individual. After modification, the cells are reinfused into the affected individual.

As used herein, the term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macriogage); CFU-GEMM (colony-forming units, multipotential); BFU-E (burst-forming units, erythroid); HPP-CFC (high proliferative potential colony-forming cells); or other types of differentiated colonies that can be obtained in culture using known protocols. As used herein, "stem" cells are less differentiated forms of progenitor cells. Typically, such cells are often positive for CD34 in humans. Some stem cells do not contain this marker, however.

Typical conditions that can be ameliorated or otherwise benefited by the treatment methods herein include, but are not limited to, hematopoietic disorders, such as aplastic anemia, leukemias, drug-induced anemias, and hematopoietic deficits from chemotherapy or radiation therapy. The methods are also useful in enhancing the success of transplantation during and following immunosuppressive treatments as well as in effecting more efficient wound healing and treatment of bacterial inflammation. The methods are also useful for treating subjects who are immunocompromised or whose immune system is otherwise impaired. Typical conditions that are ameliorated or otherwise benefited by the method of the present invention, include those subjects who are infected with a retrovirus and more specifically who are infected with human immunodeficiency virus (HIV). The method thus targets a broad spectrum of conditions for which elevation of progenitor cells and/or stem cells in a subject would be beneficial or, where harvesting of progenitor cells and/or stem cell for subsequent stem cell transplantation would be beneficial. The compounds are also administered to regenerate myocardium by mobilizing bone marrow stem cells.

Suitable dosage ranges for the active compound vary according to these considerations, but in general, the compounds are administered in the range of about 0.1 μg/kg-5 mg/kg of body weight; preferably the range is about 1 μg/kg-300 μg/kg of body weight; more preferably about 10 μg/kg-100 μg/kg of body weight. For a typical 70-kg human subject, thus, the dosage range is from about 0.7 μg-350 mg; preferably about 700 μg-21 mg; most preferably about 700 μg-7 mg. Dosages can be higher when the compounds are administered orally or transdermally as compared to, for example, i.v. administration. The compounds can be administered as a single bolus dose, a dose over time, as in i.v. or transdermal administration, or in multiple dosages.

The amount of active compound to be administered can vary according to the discretion of the skilled artisan. The amount of active compound to be administered to the recipient is within the ranges described above for stem cell mobilization. However, the administration of such amounts will vary according to the standards set forth by clinicians in the field of stem cell enhancement therapy. Administration should generally occur daily following chemotherapy or other treatment for 1 or more days, preferably daily or intermittently for up to 200 days.

The dosage regimen for increasing white blood cell survival following chemotherapy and mobilizing hematopoietic progenitor cells from bone marrow into peripheral blood with the active compounds is based on a variety of factors, including the type of injury, the age, weight, sex, medical condition of the individual, the severity of the condition, the route of administration, and the particular compound employed. Thus, the dosage regimen can vary widely, but can be determined routinely by a physician using standard methods. Dosage levels of the order of between 0.1 ng/kg and 10 mg/kg body weight of the active compounds per body weight are useful for all methods of use disclosed herein.

The treatment regime will also vary depending on the disease being treated, based on a variety of factors, including the type of injury, the age, weight, sex, medical condition of the individual, the severity of the condition, the route of administration, and the particular compound employed. For example, the active compounds are administered to an oncology patient for up to 30 days prior to a course of chemotherapy and for up to 60 days post-chemotherapy. The therapy is administered for 1 to 6 times per day at dosages as described above.

In a preferred embodiment, the active compound is administered subcutaneously. A suitable subcutaneous dose of the active compound is preferably between about 0.1 ng/kg and about 10 mg/kg administered twice daily for a time sufficient to increase mobilization of hematopoietic stem and progenitor cells from bone marrow into peripheral blood. This dosage regimen maximizes the therapeutic benefits of the treatments while minimizing the amount of agonist needed. Such an application minimizes costs as well as possible deleterious side effects.

For subcutaneous administration, the active ingredient can comprise from 0.0001% to 10% w/w, e.g. from 1% to 2% by weight of the formulation, although it can comprise as much as 10% w/w, but preferably not more than 5% w/w, and more preferably from 0.1% to 1% of the formulation. In a most preferred embodiment, subcutaneous administration of between about 1 to 1000 μg/kg/day of the active compounds is initiated at between one week before to one week after administration of a chemotherapeutic agent.

In another preferred embodiment, a subject undergoes repeated cycles of treatment according to the method disclosed herein. Preferably, a subsequent treatment cycle commences only after the administration of the compounds disclosed herein have been terminated and the subject's blood cell counts (e.g., white blood cell count) have returned to a therapeutically acceptable level (as determined by the attending veterinarian or physician), permitting the repeated chemotherapy.

In all of these embodiments, the compounds can be administered prior to, simultaneously with, or subsequent to chemotherapeutic exposure.

The compounds can be administered as sole active ingredients and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), interleukins (IL-1, IL-2, IL-3, IL-4, IL-5, IL-6, IL-7, IL-8, IL-9, IL-10 IL-11, IL-12, IL-13, IL-14, or IL-15), TPO, SCF, or other growth factor such as CSF-1, SF, EPO, leukemia inhibitory factor (LIF), or fibroblast growth factor (FGF), as well as C-KIT ligand, M-CSF and TNF-α., PIXY-321 (GM-CSF/IL-3 fusion protein), macrophage inflammatory protein, stem cell factor, thrombopoietin, growth related oncogene or chemotherapy and the like.

The term, "in conjunction with", as used herein, refers to concurrent administration of the active compound with the growth factor, as well as administration of the active compound within several days (e.g., within approximately 1 to 7 days) of administration of the growth factor. Administration of the growth factor can be before or after administration of the active compound.

In another embodiment, the active compound can be administered alone, or in conjunction with other compounds that mobilize stem cells, such as growth factor, drugs, such as cyclophosphamide or 5-fluorouracil; and/or certain antibodies, such as anti-VLA4. Combinations of these other compounds can also be used.

The active compounds can be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally.

The active compounds can be made up in a solid form (including granules, powders or suppositories) or in a liquid form (e.g., solutions, suspensions, or emulsions). The compounds can be applied in a variety of solutions. Suitable solutions for use in accordance with the preferred embodiments are sterile, dissolve sufficient amounts of the peptide, and are not harmful for the proposed application. In this regard, the compounds disclosed herein are very stable but are hydrolyzed by strong acids and bases. The compounds are soluble in organic solvents and in aqueous solutions at pH 5-8.

The active compounds can be subjected to conventional pharmaceutical operations such as sterilization and/or can contain conventional adjuvants, such as preservatives, stabilizers, wetting agents, emulsifiers, buffers etc.

For administration, the active compounds are ordinarily combined with one or more adjuvants appropriate for the indicated route of administration. The compounds can be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds disclosed herein can be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

Methods of Identifying Cells in Peripheral Blood

Any methods including quantitative and qualitative methods can be used to identify that the hematopoietic stem cells have been mobilized into the peripheral blood. The methods typically involve isolating a quantity of the patient's blood and analyzing the quantity of the cells within the blood. Any method can be used to analyze the number of cells, including but not limited to: ELISA to identify the specific cells, FACS analysis, coulter counters and other blood counting devices, morphological identification, and PCR. The cells can be identified by any method known to one of skill in the art, including but not limited to, the identification of one or more proteins which are specifically expressed by the stem cells, by morphology, by MRNA expression, and by PCR. The identification of the cells can be done at any time after administration of the GTPase inhibitor, included but not limited to: 5 minutes, 10 minutes, 20 minutes, 30 minutes, 45 minutes, 1 hour, 1.5 hours, 2 hours, 3 hours, 4 hours, 5 hours, 6 hours, 7 hours, 8 hours, 9 hours, 10 hours, 12 hours, 1 day, 2 days, 3 days, 4 days, 5 days, 6 days, 7 days, 2 weeks, 1 month, 2 months, 3 months, 4 months, 5 months, 6 months, 7 months, 8 months, 9 months, 10 months, 1 year, 2 years. Further, the mobilization can be identified soon after treatment to identify whether the treatment is working. If the treatment does not appear to be working, an alternative GTPase inhibitor or a second inhibitor can be administered.

The efficacy of the mobilization can be tested throughout treatment with the GTPase inhibitor, or alternatively, an initial test to determine efficacy can be performed. In one embodiment, a test is performed 1 day after treatment and again 1 week after treatment.

Kits

In a further aspect, kits are provided for increasing mobilization of hematopoietic stem and progenitor cells from bone marrow into peripheral blood, wherein the kits comprise an effective amount of the active compounds for increasing mobilization of hematopoietic progenitor cells from bone marrow into peripheral blood, and instructions for using the amount effective of active compound as a therapeutic. In a preferred embodiment, the kit further comprises a pharmaceutically acceptable carrier, such as those adjuvants described above. In another preferred embodiment, the kit further comprises a means for delivery of the active compound to a patient. Such devices include, but are not limited to syringes, matrical or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery can either contain the effective amount of the active compounds, or can be separate from the compounds, that are then applied to the means for delivery at the time of use.

In another aspect a method is disclosed that comprises pharmaceutical compositions for increasing mobilization of hematopoietic stem and progenitor cells from bone marrow into peripheral blood following chemotherapy, comprising the active compounds disclosed herein, an amount effective for decreasing the growth or neoplastic cells of an anti-neoplastic agent, and a pharmaceutically acceptable carrier. According to this aspect, any cytotoxic agent can be included in the pharmaceutical composition, including, but not limited to, cyclophosphamide, taxol, 5-fluorouracil, adriamycin, cisplatinun, methotrexate, cytosine arabinoside, mitomycin C, prednisone, vindesine, carbaplatinum, and vincristine. The cytotoxic agent can also be an antiviral compound that is capable of destroying proliferating cells.

The compositions and preparations described preferably contain at least 0.1% of active compound. The percentage of the compositions and preparations can, of course, be varied, and can contain between about 2% and 60% of the weight of the amount administered. The amount of active compounds in such pharmaceutically useful compositions and preparations is such that a suitable dosage will be obtained.

One embodiment also pertains to kits useful in the methods. Such a kit contains an appropriate quantity of active compound, and other components useful for the methods. For example, a kit used to facilitate in vivo expansion of hematopoietic stem cells contains an appropriate amount of the active compound to facilitate mobilization, as well as an amount of the active compound to enhance the expansion of the stem cells by growth factors. Such a kit can also contain an appropriate amount of a growth factor.

The methods, kits, and pharmaceutical compositions of the present invention, by increasing white blood cell survival following chemotherapy and mobilizing hematopoietic progenitor cells from bone marrow into peripheral blood, significantly enhance the utility of presently available treatments for clinical chemotherapeutic treatments.

Chimeric Peptides

In another embodiment, the active compound can be a chimeric peptide as described herein and in related U.S. patent application Ser. No. 10/918,648, filed Aug. 12, 2004, based on Provisional application 60/494,719 (Chimeric Peptides for the Regulation of GTPases), filed Aug. 13, 2003, herein incorporated by reference in its entirety.

The present invention also provides for novel chimeric polypeptides and nucleic acids coding for chimeric GAP proteins or polypeptides (CGP) for use in mobilization of hematopoietic cells. The activities of a chimeric GAP polypeptides in effecting mobilization can be assayed, e.g., as described below in the examples or according to methods that the skilled worker would know.

In one embodiment, the present invention provides for chimeric polypeptides and nucleic acids coding for chimeric GAP proteins or polypeptides that are isolated fusion polypeptides comprising: a) a GAP domain peptide and b) a targeting peptide, wherein the fusion polypeptide is capable of modulating GTPase activity and mobilizing hematopoietic cells. In one embodiment, the GTPase is Rho or Rac.

In one embodiment, the GAP domain is a peptide sequence containing the minimum structural domain necessary for GTPase activating protein activity. In a further embodiment, the GAP is a Rho family GAP including p50RhoGAP, p190, p122-RhoGAP, p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8, and their variants.

Generally, the targeting peptide is derived from the C-terminus amino acid sequence of a GTPase. Preferably, the C-terminus tail is from a RhoGTPase, including RhoA, RhoB, RhoC, Cdc42, Rac1, Rac2, Rac3, TC10, RhoG, RhoD, Chp, WRCH1, TCL, and RIF. More preferably, the C-terminus tail is from Rac1, Rac2, or Rac3.

In one embodiment, the GAP domain peptide is a polypeptide fragment of a GAP GTPase domain from a GAP protein, wherein the fragment comprises at least 15, 20, 25, 30, 40, 50, 60, 70, 80, 90, 100, 125, 150, 170, 200, 250 or more contiguous amino acids of the amino acid sequence of a GAP protein wherein the GAP protein is a Rho family GAP including p50RhoGAP, p190, p122-RhoGAP, p190-A, p190-B, Oligophrenin-1, GRAF, MacGAP, Cdc42GAP (p50RhoGAP), SrGAP1-SrGAP3, n-chimaerin, CdGAP, Bcr, Abr, MgcRacGAP, ARAP1, ARAP2, RICH-1, NADRIN, 3BP-1, RhoGAP8, and their variants.

In another embodiment, the targeting polypeptide is a GTPase fragment comprising at least 1, 2, 3, 4, 5, 6, 7, 8, 9, 10, 11, 12, 13, 14, 15, 16, 17, 18, 19, 20, 21, 22, 23, 24, 25, 30, or more contiguous amino acids of the C-terminus amino acid sequence of a GTPase wherein the GTPase is from the RhoGTPase family. Preferably, the C-terminus tail is from a RhoGTPase selected from the group consisting of RhoA, RhoB, RhoC, Cdc42, Rac1, Rac2, Rac3, TC10, RhoG, RhoD, Chp, WRCH1, TCL, and RIF.

In another embodiment of the present invention, the GAP domain can have some short amino acid sequences added to the C and N-termini in order to provide better binding of the GAPs. Thus, in one embodiment, the GAP domain peptide is a polypeptide fragment of a GAP GTPase domain from a GAP protein, wherein the fragment comprises an amino acid sequence of the formula:

$X_N$-GAP-$X_C$ wherein "GAP" is the polypeptide fragment of a GAP GTPase domain from a GAP protein as described herein;

wherein $X_N$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40 or more contiguous amino acids of the N-terminus amino acid sequence of a GAP protein; and wherein $X_C$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more contiguous amino acids of the C-terminus amino acid sequence of a GAP protein.

Preferably $X_N$ is a polypeptide fragment wherein the fragment comprises at least 1, 2, 3, 4, 5, 6, 7, 8, 9, 10, 11, 12, 13, 14, 15, 16, 17, 18 or more contiguous amino acids of an amino acid sequence selected from the group consisting of amino acids 1-1260 of SEQ ID NO: 2, amino acids 1-256 of SEQ ID NO: 4, amino acids 1-1013 of SEQ ID NO: 6, or fragments thereof;

More preferably, $X_N$ is selected from the group consisting of amino acids 1249-1260 of SEQ ID NO: 2, amino acids 237-256 of SEQ ID NO: 4, amino acids 996-1013 of SEQ ID NO: 6, or fragments thereof.

Preferably, $X_C$ is an amino acid fragment comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more contiguous amino acids of the amino acids 1432-1513 of SEQ ID NO:2, amino acids 427-439 of SEQ ID NO:4, amino acids 1206-1227 of SEQ ID NO:6, or fragments thereof.

More preferably, $X_C$ is selected from the group consisting of amino acids 1432-1513 of SEQ ID NO:2, amino acids 427-439 of SEQ ID NO:4, amino acids 1206-1227 of SEQ ID NO:6, or fragments thereof In another embodiment, the targeting polypeptide is a peptide fragment wherein the fragment comprises at least 1, 2, 3, 4, 5, 6, 7, 8, 9, 10, 11, 12, 13, 14, 15, 16, 17, 18 or more contiguous amino acids of the following amino acid sequences:

LQARRGKKKSG-CLVL (SEQ ID NO:14)
LQKRYGSQNGCINCCKVL (SEQ ID NO:15)
LQVRKNKRRRG-CPIL (SEQ ID NO:16)
PEPKKSRRCVLL (SEQ ID NO:17)
PVKKRKRKCLLL (SEQ ID NO:18)
PTRQQKRACSLL (SEQ ID NO:19)
PVKKPGKKCTVF (SEQ ID NO:20)
or fragments or derivatives thereof.

More preferably, the targeting polypeptide is a targeting polypeptide fragment wherein the fragment comprises an amino acid sequence selected from the group consisting of amino acids:

LQARRGKKKSG-CLVL (SEQ ID NO:14)
LQKRYGSQNGCINCCKVL (SEQ ID NO:15)
LQVRKNKRRRG-CPIL (SEQ ID NO:16)
PEPKKSRRCVLL (SEQ ID NO: 17)
PVKKRKRKCLLL (SEQ ID NO:18)
PTRQQKRACSLL (SEQ ID NO:19)
PVKKPGKKCTVF (SEQ ID NO:20)
or fragments or derivatives thereof.

The present invention also provides for importing the biologically active chimeric peptides into intact cells. Such molecules can be engineered by forming a complex by attaching an importation competent signal peptide sequence to a selected biologically active chimeric GAP molecule and administering the complex to the cell. The complex is then imported across the cell membrane by the cell. Thus, the present invention also provides a method of importing a biologically active molecule into a cell ex vivo or in vivo comprising administering to the cell, under import conditions, a complex comprising the molecule linked to an importation competent signal peptide, thereby importing the molecule into the cell. In one embodiment, the chimeric GAP polypeptides, when linked to a signal peptide and transported into cells, induces a mobilization response in the hematopoietic stem and progenitor cells.

Suitable import conditions are exemplified herein and include cell and complex temperature between about 18° C. and about 42° C., with a preferred temperature being between about 22° C. and about 37° C. For administration to a cell in a subject, the complex, once in the subject, will of course adjust to the subject's body temperature. For ex vivo administration, the complex can be administered by any standard methods that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the complex is encapsulated, or rectal administration, particularly when the complex is in suppository form.

A pharmaceutically acceptable carrier includes any material that is not biologically or otherwise undesirable, i.e., the material can be administered to an individual along with the selected complex without causing any undesirable biological effects or interacting in a deleterious manner with any of the other components of the pharmaceutical composition in which it is contained. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like. Actual methods of preparing such dosage forms are known, or will be apparent, to those skilled in this art; for example, see Remington's Pharmaceutical Sciences.

In one embodiment, the present invention utilizes a complex comprising the selected biologically active chimeric GAP peptide linked to an importation competent signal peptide. As discussed above, the biologically active molecule can be selected from any of a variety of molecules, with its selection being dependent upon the purpose to be accomplished by importing the molecule into the selected cell.

In one embodiment, the present invention isolated fusion polypeptide comprising: a) a membrane-translocating peptide, b) a GAP domain peptide and c) a targeting peptide derived from the C-terminus amino acid sequence of a GTPase Generally, the membrane-translocating peptide is a peptide of about 8 to about 50 residues. Preferably, the a membrane-translocating peptide is a peptide of about 8 to about 50 residues comprising at least eight consecutive residues of SEQ ID NOs:21, 22, 23, 24, or 25. More preferably, the signal peptide is an importation competent signal peptide sequence ("membrane-translocating peptide") having about 8 to about 50 residues comprising at least eight consecutive residues of SEQ ID NOs: 21, 22, 23, 24, or 25.

An "importation competent signal peptide" or "membrane-translocating peptide", as used herein, is a sequence of amino acids generally of a length of about 8 to about 50 or more amino acid residues, many (typically about 55-60%) residues of which are hydrophobic such that they have a hydrophobic, lipid-soluble portion. Preferably, the importation competent signal peptide is a sequence of amino acids generally of a length of about 8 to about 24 or more amino acid residues. The hydrophobic portion is a common, major motif of the signal peptide, and it is often a central part of the signal peptide of protein secreted from cells. A signal peptide is a peptide capable of penetrating through the cell membrane to allow the export of cellular proteins. The signal peptides of this invention are also "importation competent," i.e., capable of penetrating through the cell membrane from outside the cell to the interior of the cell. The amino acid residues can be mutated and/or modified (i.e., to form mimetics) so long as the modifications do not affect the translocation-mediating function of the peptide. Thus the word "peptide" includes mimetics and the word "amino acid" includes modified amino acids, as used herein, unusual amino acids, and D-form amino acids. All importation competent signal peptides encompassed by this invention have the function of mediating translocation across a cell membrane from outside the cell to the interior of the cell. Such importation competent signal peptides could potentially be modified such that they lose the ability to export a protein but maintain the ability to import molecules into the cell. A putative signal peptide can easily be tested for this importation activity following the teachings provided herein, including testing for specificity for any selected cell type.

The present invention relates to chimeric GAP peptides with an importation competent signal peptide sequence attached and their use in mediating membrane-translocation and import of a polypeptide, protein domain, or full-length protein into a cell. The present invention provides for importation competent signal peptide sequences of 8-24 amino acids for protein import and also provide for a DNA sequence encoding this 8 to 24-amino acid peptide to construct a plasmid expression vector for genetically engineering proteins with cell membrane permeability by expressing the 8-24 amino acid importation competent signal peptide sequence as a fusion with a target protein for import into the cell.

In the preferred embodiment of the present invention, the amino acid sequence of the importation competent signal peptide sequence is selected from the group consisting of Pro-Thr-Arg-Gln-Gln-Lys-Arg-Pro-Cys-Ser-Leu-Leu (SEQ ID NO:21), Pro-Gln-Pro-Thr-Arg-Gln-Gln-Lys-Arg-Pro-Cys-Ser-Leu-Leu, (SEQ ID NO:22), Gly-Arg-Arg-Arg-Arg-Arg-Arg-Arg-Gly-Thr-Arg-Gln-Gln-Lys-Arg-Pro, (SEQ ID NO:23), Gly-Arg-Arg-Arg-Arg-Arg-Arg-Arg-Gly-Arg-Pro-Arg-Gln-Thr-Gln-Lys, (SEQ ID NO:24), and Gly-Arg-Arg-Arg-Arg-Arg-Arg-Arg-Gly-Thr-Arg-Gln-Gln-Lys-Arg-Pro-Cys-Leu-Leu (SEQ ID NO:25). As used herein, however, the term "peptide" is intended to include mimetics and the term "amino acid" is intended to include D-form amino acids and modified amino acids. These substitutions can be made by someone of skill in the art, using the known structural similarities between the molecules. The membrane translocating sequence can be located immediately adjacent to, or some distance from, the cargo protein as produced by the recombinant nucleotide vector of the present invention. Therefore, the amino acid sequence is also intended to include any peptide or protein sequence that can include additional amino acids either N-terminal or C-terminal to the listed sequence, or both. Alternative sequences are intended to include alternative amino acids, as well as additional C-terminal or N-terminal amino acids.

Signal peptides can be selected, for example, from the SIGPEP database, that also lists the origin of the signal peptide. When a specific cell type is to be targeted, such as hematopoietic cells, a signal peptide used by that cell type can be chosen. Additionally, signal peptides endogenous to the cell type can be chosen for importing biologically active molecules into that cell type. And again, any selected signal peptide can be routinely tested for the ability to translocate across the cell membrane of any given cell type according to the teachings herein. Specifically, the signal peptide of choice can be conjugated to a biologically active molecule, e.g., a functional domain of a cellular protein or a reporter construct, and administered to a cell, and the cell is subsequently screened for the presence of the active molecule. Signal peptides are known in the art, e.g., U.S. Pat. Nos. 6,573,068; 6,548,633; 6,495,518; 6,451,601; 6,432,680; 6,312,922; 6,248,558; 6,245,739; 6,043,339; 5,807,746; 5,464,822, incorporated herein by reference. Any signal peptide, however, capable of translocating across the cell membrane into the interior of the selected target cell can be used according to this invention.

The presence of modified amino acids in the signal peptide can additionally be useful for rendering a complex, wherein the biologically active molecule is a peptide, polypeptide or protein, more resistant to peptidases in the subject Thus these signal peptides can allow for more effective treatment by allowing more peptides to reach their target and by prolonging the life of the peptide before it is degraded. Additionally, one can modify the amino acid sequence of the signal peptide to alter any proteolytic cleavage site present in the original signal sequence for removing the signal sequence. Cleavage sites are characterized by small, positively charged amino acids with no side chains.

By "linked" as used herein is meant that the biologically active molecule is associated with the signal peptide in such a manner that when the signal peptide crosses the cell membrane, the molecule is also imported across the cell membrane. Examples of such means of linking include (1) when the molecule is a peptide, the signal peptide (and a nuclear localization peptide, if desired) can be linked by a peptide bond, i.e., the two peptides can be synthesized contiguously; (2) when the molecule is a polypeptide or a protein, the signal peptide (and a nuclear localization peptide, if desired) can be linked to the molecule by a peptide bond or by a non-peptide covalent bond (such as conjugating a signal peptide to a protein with a crosslinking reagent); (3) for molecules that have a negative charge, such as nucleic acids, the molecule and the signal peptide (and a nuclear localization peptide, if desired) can be joined by charge-association between the negatively-charged molecule and the positively-charged amino acids in the peptide or by other types of association between nucleic acids and amino acids; (4) chemical ligation methods can be employed to create a covalent bond between the carboxy-terminal amino acid of the signal peptide (and a nuclear, localization peptide, if desired) and the molecule. Methods (1) and (2) are typically preferred.

Examples of method (1) are shown below wherein a peptide is synthesized, by standard means known in the art that contains, in linear order from the amino-terminal end, a signal peptide sequence, an optional spacer amino acid region, and a biologically active amino acid sequence, e.g., the chimeric GAP peptide. Such a peptide could also be produced through recombinant DNA techniques, expressed from a recombinant construct encoding the above-described amino acids to create the peptide.

For method (2), either a peptide bond, as above, can be utilized or a non-peptide covalent bond can be used to link the signal peptide with the biologically active polypeptide or protein. This non-peptide covalent bond can be formed by methods standard in the art, such as by conjugating the signal peptide to the polypeptide or protein via a crosslinking reagent, for example, glutaraldehyde. Such methods are standard in the art. For method (3) the molecules can simply be mixed with the signal peptide and thus allowed to associate. These methods are performed in the same manner as association of nucleic acids with cationic liposomes. Alternatively, covalent (thioester) bonds can be formed between nucleic acids and peptides. Such methods are standard in the art.

For method (4), standard chemical ligation methods, such as using chemical crosslinkers interacting with the carboxy-terminal amino acid of the signal peptide, can be utilized. Such methods are standard in the art and can readily be performed to link the carboxy terminal end of the signal peptide to any selected biologically active molecule.

The complex that is administered to a subject can further comprise a liposome. Cationic and anionic liposomes are contemplated by this invention, as well as liposomes having neutral lipids. Cationic liposomes can be complexed with the signal peptide and a negatively-charged biologically active molecule by mixing these components and allowing them to charge-associate. Cationic liposomes are particularly useful when the biologically active molecule is a nucleic acid because of the nucleic acid's negative charge. Examples of cationic liposomes include lipofectin, lipofectamine, lipofectace and DOTAP. Anionic liposomes generally are utilized to encase within the liposome the substances to be delivered to the cell. Procedures for forming cationic liposomes encasing substances are standard in the art and can readily be utilized herein by one of ordinary skill in the art to encase the complex of this invention.

The signal peptide utilized can be chosen from signal peptides known to be utilized by the selected target cell, or a desired signal peptide can be tested for importing ability given the teachings herein. Generally, however, all signal peptides have the common ability to cross cell membranes due, at least in part, to their hydrophobic character. Thus, in general, a membrane-permeable signal peptide can be designed and used for any cell type, since all eukaryotic cell membranes have a similar lipid bilayer.

One particularly useful example is to import a chimeric peptide into cells of hematopoietic cells, thereby allowing the stem cells to be mobilized by the subject. The invention also provides a complex comprising a biologically active molecule linked to an importation competent signal peptide and to a nuclear localization peptide.

The invention further provides a complex comprising an importation competent signal peptide linked to a biologically active agent selected from the group consisting of a nucleic acid, a carbohydrate, a lipid, a glycolipid and a therapeutic agent. This complex can further comprise a liposome. These complexes can be formed as described above. Liposomes can be selected as described above. The complex can be placed in a pharmaceutically acceptable carrier.

Another aspect of this invention features isolated or recombinant chimeric GAP proteins and polypeptides. In preferred embodiments, the isolated chimeric GAP includes at least one or more of the following domains: a RhoGAP domain, and/or a transmembrane domain.

In a preferred embodiment, the chimeric GAP has an amino acid sequence at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to the amino acid sequence selected from the group consisting of SEQ ID NO:2, SEQ ID NO:4, and SEQ ID NO:6 and includes at least one or more of the GAP domains. In another preferred embodiment, the chimeric GAP modulates GTPase activity, and includes at least one or more GAP domain. In a more preferred embodiment, the chimeric GAP modulates GTPase activity of at least Rac1 and/or Rac2.

In yet another preferred embodiment, the chimeric GAP is encoded by a nucleic acid molecule having a nucleotide sequence that hybridizes under stringent hybridization conditions to a nucleic acid molecule comprising the nucleotide sequence selected from the group consisting of SEQ ID NO:2, SEQ ID NO:4, and SEQ ID NO:6 and includes at least one or more GAP domain.

In another embodiment, the invention features fragments of the protein having the amino acid sequence of SEQ ID NO:2, SEQ ID NO:4, or SEQ ID NO:6 wherein the fragment comprises at least 15, 20, 30, 40, 50, 60, 70, 80, 90, 100, 125, 150, 175, 200, 250 amino acids (e.g., contiguous amino acids) of an amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13. In another embodiment, the protein has the amino acid sequence of SEQ ID NO:7, SEQ ID NO:8, SEQ ID NO:9, SEQ ID NO:10, SEQ ID NO:11, SEQ ID NO:12, or SEQ ID NO:13.

In another embodiment, the invention features an isolated chimeric GAP peptide, that is encoded by a nucleic acid molecule consisting of a nucleotide sequence at least about 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to a nucleotide sequence selected from the group consisting of SEQ ID NO:1, SEQ ID NO:3, or SEQ ID NO:5, or a complement thereof. This invention further features an isolated chimeric protein that is encoded by a nucleic acid molecule consisting of a nucleotide sequence that hybridizes under stringent hybridization conditions to a nucleic acid molecule comprising a nucleotide sequence selected from the group consisting of SEQ ID NO:1, SEQ ID NO:3, or SEQ ID NO:5, or a complement thereof.

In another preferred embodiment, a chimeric GAP protein can be assayed for the ability to (1) interact with a non-GAP protein molecule, e.g., a GTPase or a GAP ligand or substrate; (2) modulate a GAP-dependent signal transduction pathway; (3) modulate Rho GTPase-dependant signal transduction; (4) modulate Rho GTP hydrolysis activity; (5) modulate levels of GTP/GDP bound to a Rho protein.

Pharmaceutical Preparations

The chimeric GAP proteins or biologically active portions thereof can be incorporated into pharmaceutical compositions, that optionally include pharmaceutically acceptable carriers.

In another aspect, the invention provides a method for modulating Rac1 and Rac2 activity comprising contacting a cell with an active compound that modulates Rac1 and Rac2 activity such that Rac1 and Rac2 activity in the cell is modulated thereby causing mobilization of hematopoietic cells. In one embodiment, the active compound inhibits Rac1 and Rac2 activity. In another embodiment, the active compound stimulates Rac1 and Rac2 activity. In another embodiment, the active compound modulates expression of Rac1 and Rac2 by modulating transcription of a gene or translation of an mRNA. In yet another embodiment, the active compound is a nucleic acid molecule having a nucleotide sequence that is antisense to the coding strand of an MRNA or a gene.

In one embodiment, the methods of the present invention are used to treat a subject in need of hematopoietic cell mobilization by administering an active compound that is a Rac1 and Rac2 modulator to the subject. In one embodiment, the Rac1 and Rac2 modulator is a single chimeric GAP protein.

In another embodiment, the Rac1 and Rac2 modulator is two chimeric GAP proteins that inhibit Rac1 and Rac2, respectively. In another embodiment the Rac1 and Rac2 modulator is a chimeric GAP nucleic acid molecule. In yet another embodiment, the Rac1 and Rac2 modulator comprises one or more additional agents selected from the group consisting of a peptide, peptidomimetic, or other small molecule.

In another preferred embodiment, the nucleic acid molecule includes a fragment of at least 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, or more nucleotides (e.g., contiguous nucleotides) of a nucleotide sequence selected from the group consisting of SEQ ID NO:1, SEQ ID NO:3, and SEQ ID NO:5, or a complement thereof.

In another embodiment, a GAP nucleic acid molecule includes a nucleotide sequence encoding a protein having an amino acid sequence sufficiently identical to the amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13.

In a preferred embodiment, a chimeric GAP nucleic acid molecule includes a nucleotide sequence encoding a protein having an amino acid sequence at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, 99.5% or more identical to the entire length of an amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13.

In other preferred embodiments, the nucleic acid molecule encodes a variant of a polypeptide comprising an amino acid sequence selected from the group consisting of SEQ ID NO:7, SEQ ID NO:8, SEQ ID NO:9, SEQ ID NO:10, SEQ ID NO:11, SEQ ID NO:12, and SEQ ID NO:13., wherein the nucleic acid molecule hybridizes to a nucleotide sequence selected from the group consisting of amino acid sequence selected from the group consisting of SEQ ID NO:1, SEQ ID NO:3, and SEQ ID NO:5, or a complement thereof under stringent conditions.

Another aspect provides a vector comprising a chimeric GAP nucleic acid molecule. In certain embodiments, the vector is a recombinant expression vector. In another embodiment, a host cell containing a vector is provided herein. In yet another embodiment, a host cell containing a nucleic acid molecule is provided herein. Another embodiment provides a method for producing a protein by culturing a host cell in a suitable medium, e.g., a mammalian host cell such as a non-human mammalian cell containing a recombinant expression vector, such that the protein is produced.

In a further embodiment, polypeptide fragments of chimeric GAP are disclosed. The fragments are preferably biologically-active. By biologically-active, it is meant that the polypeptide fragment possesses an activity in a living system or with components of a living system. Biological-activities include: a specific binding affinity for G-proteins, in particular RhoA, RhoB, RhoC, Cdc42, Rac1, Rac2, Rac3, or acting as an agonist or antagonist of Rho GTPase activity. Such activities can be assayed routinely, e.g., according to the methods described above and below. Various fragments can be prepared.

Such a chimeric polypeptide can be prepared according to various methods, including, chemical, synthetic, quasi-synthetic, and/or recombinant methods. A chimeric nucleic acid coding for a chimeric polypeptide can contain the various domains or desired polypeptides in a continuous or interrupted open reading frame, e.g., containing introns, splice sites, enhancers, etc.

The chimeric nucleic acid can be produced according to various methods. See, e.g., U.S. Pat. No. 5,439,819. A domain or desired polypeptide can possess any desired property, including, a biological function such as catalytic, signaling, growth promoting, cellular targeting, etc., a structural function such as hydrophobic, hydrophilic, membrane-spanning, etc., receptor-ligand functions, and/or detectable functions, e.g., combined with enzyme, fluorescent polypeptide, green fluorescent protein GFP.

Polypeptide

A polypeptide can be produced in an expression system, e.g., in vivo, in vitro, cell-free, recombinant, cell fusion, etc. Modifications to the polypeptide imparted by such system include, glycosylation, amino acid substitution (e.g., by differing codon usage), polypeptide processing such as digestion, cleavage, endopeptidase or exopeptidase activity, attachment of chemical moieties, including lipids, phosphates, etc. For example, some cell lines can remove the terminal methionine from an expressed polypeptide.

A polypeptide can be recovered from natural sources, transformed host cells (culture medium or cells) according to the usual methods, including, ammonium sulfate or ethanol precipitation, acid extraction, anion or cation exchange chromatography, phosphocellulose chromatography, hydrophobic interaction chromatography, hydroxyapatite chromatography and lectin chromatography. It may be useful to have low concentrations (approximately 0.1-5 mM) of calcium ion present during purification (Price, et al., J. Biol. Chem., 244: 917 (1969)). Protein refolding steps can be used, as necessary, in completing the configuration of the mature protein. Finally, high performance liquid chromatography (HPLC) can be employed for final purification steps. A nucleic acid comprising a nucleotide sequence coding for a polypeptide disclosed herein can include only coding sequence of chimeric GAP; coding sequence of chimeric GAP and additional coding sequence (e.g., sequences coding for leader, secretory, targeting, enzymatic, fluorescent or other diagnostic peptides), coding sequence of chimeric GAP and non-coding sequences, e.g., untranslated sequences at either a 5' or 3' end, or dispersed in the coding sequence, e.g., introns. A nucleic acid comprising a nucleotide sequence coding without interruption for a chimeric GAP polypeptide means that the nucleotide sequence contains an amino acid coding sequence for a chimeric GAP polypeptide, with no non-coding nucleotides interrupting or intervening in the coding sequence, e.g., absent intron(s). Such a nucleotide sequence can also be described as contiguous.

Nucleic Acid

A nucleic acid as disclosed in the preferred embodiments herein can comprise an expression control sequence operably linked to a nucleic acid as described above. The phrase "expression control sequence" means a nucleic acid sequence that regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, the promoter drives expression of the coding sequence. Expression control sequences can be heterologous or endogenous to the normal gene.

A nucleic acid as disclosed herein can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc.

A nucleic acid or polypeptide can comprise one or more differences in the nucleotide or amino acid sequence. Changes or modifications to the nucleotide and/or amino acid sequence can be accomplished by any method available, including directed or random mutagenesis. A nucleotide sequence coding for a chimeric GAP polypeptide can contain codons found in a naturally-occurring gene, transcript, or cDNA or it can contain degenerate codons coding for the same amino acid sequences.

Modifications to a chimeric GAP sequence, e.g., mutations, can also be prepared based on homology searching from gene data banks, e.g., GenBank, EMBL. Sequence homology searching can be accomplished using various methods, including algorithms described in the BLAST family of computer programs, the Smith-Waterman algorithm, etc.

A nucleic acid can comprise, e.g., DNA, RNA, synthetic nucleic acid, peptide nucleic acid, modified nucleotides, or mixtures. A DNA can be double- or single-stranded. Nucleotides comprising a nucleic acid can be joined via various known linkages, e.g., ester, sulfamate, sulfamide, phosphorothioate, phosphoramidate, methylphosphonate, carbamate, etc., depending on the desired purpose, e.g., resistance to nucleases, such as RNase H, improved in vivo stability, etc. See, e.g., U.S. Pat. No. 5,378,825.

Various modifications can be made to the nucleic acids, such as attaching detectable markers (avidin, biotin, radioactive elements), moieties that improve hybridization, detection, or stability. The nucleic acids can also be attached to solid supports, e.g., nitrocellulose, nylon, agarose, diazotized cellulose, latex solid microspheres, polyacrylamides, etc., according to a desired method. See, e.g., U.S. Pat. Nos. 5,470,967, 5,476,925, 5,478,893.

A nucleic acid as disclosed herein can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for the nucleic acid. Effective conditions includes any culture conditions that are suitable for achieving production of the polypeptide by the host cell, including effective temperatures, pH, medias, additives to the media in which the host cell is cultured (e.g., additives that amplify or induce expression such as butyrate, or methotrexate if the coding nucleic acid is adjacent to a dhfr gene), cyclohexamide, cell densities, culture dishes, etc. A nucleic acid can be introduced into the cell by any effective method including, e.g., calcium phosphate precipitation, electroporation, injection, DEAE-Dextran mediated transfection, fusion with liposomes, and viral transfection. A cell into which a nucleic acid disclosed herein has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells, e.g., COS-7, CHO, HeLa, LTK, NIH 3T3, Rat 1 fibroblasts, yeast, insect cells, such as Sf9 (*S. frugipeda*) and *Drosophila*, bacteria, such as *E. coli, Streptococcus, bacillus*, yeast, fungal cells, plants, embryonic stem cells (e.g., mammalian, such as mouse or human), cancer or tumor cells. Sf9 expression can be accomplished in analogy to Graziani et al., Oncogene, 7:229-235, 1992. Expression control sequences are similarly selected for host compatibility and a desired purpose, e.g., high copy number, high amounts, induction, amplification, controlled expression. Other sequences that can be employed include enhancers such as from SV40, CMV, inducible promoters, cell-type specific elements, or sequences that allow selective or specific cell expression.

In addition to a chimeric GAP nucleic acid, another gene of interest can be introduced into the same host for purposes of, e.g., modulating expression of the chimeric GAP nucleic acid, elucidating chimeric GAP or GTPase function or that of the gene of interest. Genes of interest include other oncogenes, genes involved in the cell cycle, etc. Such genes can be the normal gene, or a variation, e.g., a mutation, chimera, polymorphism, etc.

The modulation of GTPase activity by a chimeric GAP, or derivatives thereof, can be measured according to various known procedures, e.g., Eva and Aaronson, Nature, 316:273-275, 1985; Hart et a., J. Biol. Chem., 269:62-65, 1994. A compound can be added at any time during the method to determine its effect on the GTPase activity of chimeric GAP. Various cell lines can also be used.

Other assays for GTPase-mediated signal transduction can be accomplished according to procedures known in the art, e.g., as described in U.S. Pat. Nos. 5,141,851; 5,420,334; 5,436,128; and 5,482,954. In addition, peptides that inhibit the interaction, e.g., binding, between chimeric GAP and a G-protein, such as RhoA, can be identified and prepared according to EP 496 162.

The nucleic acid molecules, proteins, and derivative described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a chimeric GAP protein has one or more of the following activities: (1) it interacts with a non-GAP protein molecule, e.g., a GTPase or a GAP ligand; (2) it modulated a GAP-dependent signal transduction pathway; (3) it modulates GTP/GDP levels; and (4) it modulates GTPase signaling mechanisms, and, thus, can be used to, for example, (1) modulate the interaction with a non-GAP protein molecule, e.g., a GTPase; (2) activate a GAP-dependent signal transduction pathway; (3) modulate GTP/GDP levels; and (4) modulate GTPase signaling mechanisms.

The isolated nucleic acid molecules can be used, for example, to express chimeric GAP protein and to modulate GTPase activity, as described further below. The chimeric GAP proteins can be used to mobilize hematopoietic cells.

A further embodiment provides for both prophylactic and therapeutic methods of treating a subject at risk of (or susceptible to) a disorder or having a disorder associated with hematopoietic cell mobilization.

The practice of the methods and production of the compositions disclosed herein employs, unless otherwise indicated, conventional techniques of synthetic organic chemistry, protein chemistry, molecular biology, microbiology, and recombinant DNA technology, that are well within the skill of the art. Such techniques are explained fully in the literature.

In preferred embodiments, the chimeric GAP peptide is water soluble; or is soluble in a physiological fluid, preferably, one that is at physiological pH, for example, blood plasma.

It is possible to design any number of peptide analogues, having different amino acid sequences, provided that the local charge distribution (and overall net charge) and secondary structure, and hence the biological activity is maintained. Such peptide analogues will generally differ from the native protein sequences by conservative amino acid substitutions (e.g., substitution of Leu for Val, or Arg for Lys, etc.) well known to those skilled in the art of biochemistry.

The peptides, once designed, can be synthesized by any of a number of established procedures, including, e.g., the expression of a recombinant DNA encoding that peptide in an appropriate host cell. Alternatively, these peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent. The peptides so synthesized are then labeled with a reagent that enables the monitoring of the peptide after its administration to a patient.

As used herein, the term "substantially corresponds" means a peptide amino acid sequence having approximately 70% homology in amino acid sequence to a chimeric GAP peptide.

The term "chemical derivative" is meant to include any peptide derived from a peptide and in which one or more amino acids have been chemically derivatized by reaction of one or more functional side groups of the amino acid residues present in the peptide. Thus, a "chemical derivative" as used herein is a peptide that is derived from the peptides identified herein by one or more chemical steps. Examples of derivatized molecules include molecules where free amino groups have been derivatized to form amine hydrochlorides, p-toluene sulfonyl groups, carbobenzoxy groups, t-butyloxycarbonyl groups, thiourethane-type derivatives, trifluroroacetyl groups, chioroacetyl groups or formyl groups. Free carboxyl groups can be derivatized to form salts, methyl and ethyl esters or other types of esters or hydrazides.

Free hydroxyl groups can be derivatized to form 0-acyl or 0-alkyl derivatives. The imidazole nitrogen of histidine can be derivatized to form N-im-benzylhistidine. Also included as chemical derivatives are those peptides that contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

The peptides, homologues and analogs thereof can be synthesized by a number of known techniques. For example, the peptides can be prepared using the solid-phase synthetic technique or other peptide synthesis techniques well known to those skilled in the art. The peptides might also be prepared by chemical or enzymatic cleavage from larger portions of the chimeric GAP peptide.

Additionally, the peptides can also be prepared by recombinant DNA techniques. For most of the amino acids used to build proteins, more than one coding nucleotide triplet (codon) can code for a particular amino acid residue. This property of the genetic code is known as redundancy. Therefore, a number of different nucleotide sequences can code for a particular subject eating suppressant peptide. One aspect also contemplates a deoxyribonucleic acid (DNA) molecule or segment that defines a gene coding for, i.e., capable of expressing, a subject polypeptide or a subject chimeric polypeptide from which a polypeptide can be enzymatically or chemically cleaved.

DNA molecules that encode the subject peptides can be synthesized by chemical techniques, for example, the phosphotriester method of Matteuccie et al., Chem. Soc. 103:3185 (1981). Using a chemical DNA synthesis technique, desired modifications in the peptide sequence can be made by making substitutions for bases that code for the native amino acid sequence. Ribonucleic acid equivalents of the above described DNA molecules can also be used.

A nucleic acid molecule comprising a vector capable of replication and expression of a DNA molecule defining coding sequence for a subject polypeptide or subject chimeric polypeptide is also contemplated.

One embodiment provides DNA molecules encoding the chimeric proteins. The DNA construct generally comprises a transcriptional promoter sequence followed downstream by and in proper reading frame with a DNA sequence encoding a chimeric protein, and a transcriptional terminator.

The DNA compositions can be derived from genomic DNA or cDNA, prepared by synthesis or can be a hybrid of the various combinations. Recombinant nucleic acids comprising sequences otherwise not naturally occurring are also provided. An isolated DNA sequence includes any sequence that has been obtained by primer or hybridization reactions or subjected to treatment with restriction enzymes or the like. Novel DNA sequences, such DNA sequences as parts of expression cassettes and vectors, as well as their presence in cells are provided, where the novel sequences comprise domains that do not naturally exist together.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene that has a high level of expression. Alternatively, promoters from mammalian expression products, such as actin, collagen, myosin, etc., can be employed. Transcriptional initiation regulatory signals can be selected that allow for repression or activation, so that expression of the genes can be modulated. Of interest are regulatory signals that are temperature-sensitive so that by varying the temperature, expression can be repressed or initiated, or that are subject to chemical regulation, e.g., metabolite.

As is widely known, translation of eucaryotic MRNA is initiated at the codon, that encodes the first methionine. For this reason, it is preferable to ensure that the linkage between a eucaryotic promoter and a DNA sequence that encodes the desired chimeric protein molecule does not contain any intervening codons that are capable of encoding a methionine (i.e., AUG). The presence of such codons results either in the formation of a different fusion protein (if the AUG codon is in the same reading frame as the desired chimeric protein molecule encoding DNA sequence) or a frame-shift mutation (if the AUG codon is not in the same reading frame as the desired chimeric protein molecule encoding sequence).

A wide variety of promoters have been described in the literature, that are constitutive or inducible, where induction can be associated with a specific cell type or a specific level of maturation. Alternatively, a number of viral promoters are known that can also find use. Promoters of interest include, but are not limited to, the beta-actin promoter, SV40 early and late promoters, immunoglobulin promoter, human cytomegalovirus promoter, the metallothionine promoter and the Friend spleen focus-forming virus promoter. The promoters may or may not be associated with enhancers, where the enhancers can be naturally associated with the particular promoter or associated with a different promoter.

The sequence of the open reading frame can be obtained from genomic DNA or cDNA, or can be synthesized, or can comprise combinations thereof. Depending upon the size of the genomic DNA and the number of introns, one may wish to use cDNA or a combination thereof. In many instances, it is found that introns stabilize the MRNA. Also, one may provide for non-coding regions that stabilize the mRNA.

The desired chimeric protein molecule encoding sequence and an operably linked promoter can be introduced into a recipient cell as a non-replicating DNA (or RNA) molecule, that can either be a linear molecule or, more preferably, a closed covalent circular molecule. Since such molecules are incapable of autonomous replication, the expression of the desired chimeric protein molecule can occur through the transient expression of the introduced sequence. Alternatively, permanent expression can occur through the integration of the introduced sequence into the host chromosome.

Using standard techniques of recombinant DNA technology, vectors for transforming suitable host cells can be constructed that contain cDNA sequences corresponding to the structural gene for the chimeric GAP fusion protein. Suitable vectors, for example, are plasmid vectors that include control and regulatory sequences operably linked to the cDNA sequence coding for the chimeric GAP protein.

DNA or cDNA molecules that encode the chimeric protein molecule can be operably linked into an expression vector and introduced into a host cell to enable the expression of the chimeric GAP protein by that cell. Two DNA sequences (such as a promoter region sequence and a desired chimeric protein molecule encoding sequence) are said to be operably linked if the nature of the linkage between the two DNA sequences does not (1) result in the introduction of a frame-shift mutation, (2) interfere with the ability of the promoter region sequence to direct the transcription of the desired chimeric protein molecule encoding gene sequence, or (3) interfere with the ability of the desired chimeric protein molecule gene sequence to be transcribed by the promoter region sequence.

A DNA sequence encoding the chimeric protein molecule can be recombined with vector DNA in accordance with conventional techniques, including blunt-ended or staggerended termini for ligation, digestion to provide appropriate termini, filling in of cohesive ends as appropriate, alkaline phosphatase treatment to avoid undesirable joining, and ligation with appropriate ligases.

Expression vectors for these cells can include expression control sequences, such as an origin of replication, a promoter, an enhancer and necessary processing information sites, such as ribosome-binding sites, RNA splice sites, polyadenylation sites, and transcriptional terminator sequences. Preferably, the enhancers or promoters will be those previously shown to be effective in the host cells of interest, although it will be understood that in many cases others will be equally or more appropriate.

Mammalian expression vectors for use in carrying out the embodiments will include a promoter capable of directing the transcription of a cloned gene or cDNA. Preferred promoters include viral promoters and cellular promoters. Preferred viral promoters include the major late promoter from adenovirus 2 (Kaufman and Sharp, Mol. Cell. Biol. 2: 1304-13199, 1982) and the SV40 promoter (Subramani et al., Mol. Cell. Biol. 1: 854-864, 1981). Preferred cellular promoters include the mouse metallothionein 1 promoter (Palmiter et al., Science 222: 809-814, 1983) and a mouse V kappa promoter (Grant et al., Nuc. Acids Res. 15: 5496, 1987). A particularly preferred promoter is a mouse VH promoter (Loh et al., ibid.). Such expression vectors can also contain a set of RNA splice sites located downstream from the promoter and upstream from the DNA sequence encoding the peptide or protein of interest. Preferred RNA splice sites can be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the adenovirus 5 EIB region and the human growth hormone gene terminator (DeNoto et al., Nuc. Acids Res. 9: 3719-3730, 1981). A particularly preferred polyadenylation signal is the VH gene terminator (Loh et al., ibid.). The expression vectors can include a noncoding viral leader sequence, such as the adenovirus 2 tripartite leader, located between the promoter and the RNA splice sites. Preferred vectors can also include enhancer sequences, such as the SV40 enhancer and the mouse enhancer (Gillies, Cell 33: 717-728, 1983). Expression vectors can also include sequences encoding the adenovirus VA RNAs.

In general, plasmid vectors containing replication and control sequences, that are compatible with the recombinant host cells, are used as cloning vectors for the DNA molecules. A DNA sequence encoding the chimeric proteins can be inserted into a suitable eucaryotic expression vector, that in turn is used to transfect eucaryotic cells. A eucaryotic expression vector, as used herein, is meant to indicate a DNA construct containing elements that direct the transcription and translation of DNA sequences encoding chimeric proteins of interest. Such elements include promoters, enhancers, transcription terminators and polyadenylation signals. By virtue of the inclusion of these elements operably linked within the DNA constructs, the resulting eucaryotic expression vectors contain the information necessary for expression of the polypeptides of interest.

For a mammalian host, several possible vector systems are available for expression of the desired chimeric protein molecule. One class of vectors utilizes DNA elements that provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells that have stably integrated the introduced DNA into their chromosomes can be selected by also introducing one or more markers that allow selection of host cells that contain the expression vector. The selectable marker gene can either be directly linked to the DNA sequences to be expressed, or introduced into the same cell by co-transformation. Additional elements may also be needed for optimal synthesis of MRNA. These elements can include splice signals, as well as transcription promoters, enhancers, and termination signals.

Retroviral vectors have been demonstrated to be particularly useful for delivery of the RhoGAP chimeras. Like other cases of retrovirus-based gene transfer approach, the copy number of the introduced RhoGAP-Rho chimeras in the host cells will likely to be important for the efficacy of their application. Although p190-RhoC-C was effective in downregulating the biochemical activity and migration phenotype of RhoC when expressed with the low copy number vector MIEG3, expression of p190-RhoA-C or p190-RhoB-C with MIEG3 was found to be insufficient for downregulating the biochemical activity or transforming activity of RhoA-F30L or RhoB-F30L. However, expression of p190-RhoA-C with the high copy number retroviral vector, SF91-EMCV-IRES-GFP, that has been in use for gene therapy trials, can specifically decrease both the biochemical activity of F30LRhoA and the RhoA-F30L-induced transformation under conditions in which p190-RhoB-C, p190-RhoC-C or p190 alone expressed by using the same vector did not affect RhoA-F30L activity nor the RhoA-F30L-induced transformation. These results highlight the importance of dose-dependence in effectiveness and specificity when applying this method to future animal and human trials.

Such expression vectors can also contain a set of RNA splice sites located downstream from the promoter and upstream from the DNA sequence encoding the polypeptide or protein of interest. Preferred RNA splice sites can be obtained from adenovirus and/or immunoglobulin genes. Also contained in the expression vectors is a polyadenylation signal located downstream of the coding sequence of interest.

Polyadenylation signals include the early or late polyadenylation signals from SV40 (Kaufmnan and Sharp, ibid.), the polyadenylation signal from the Adenovirus 5 E1B region and the human growth hormone gene terminator (DeNoto et al., Nuc. Acids Res. 9:3719-3730, 1981). The expression vectors can include a noncoding viral leader sequence, such as the AdenoVirus 2 tripartite leader, located between the promoter and the RNA splice sites. Vectors can also include enhancer sequences, such as the SV40 enhancer and the mouse mu enhancer (Gillies, Cell 33: 717-728, 1983). Expression vectors can also include sequences encoding the adenovirus VA RNAs.

Once the vector or DNA sequence containing the constructs has been prepared for expression, the DNA constructs can be introduced into an appropriate host. Various techniques can be employed, such as calcium phosphate precipitated DNA transformation, electroporation, protoplast fusion, biolistics, using DNA-coated particles, transfection, and infection, where the chimeric construct is introduced into an appropriate virus, particularly a non-replicative form of the virus, or the like. After the fusion, the cells are grown in media and screened for appropriate activities. Expression of the sequence results in the production of the chimeric GAP protein.

In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker can be an amplifiable selectable marker. A preferred amplifiable selectable marker is the DHFR gene. A particularly preferred amplifiable marker is the DHFRr cDNA (Simonsen and Levinson, Proc. Natl. Adac. Sci. USA 80: 2495-2499, 1983). Selectable markers are reviewed by Thilly (Mammalian Cell Technology, Butterworth Publishers, Stoneham, Mass.) and the choice of selectable markers is well within the level of ordinary skill in the art.

Selectable markers can be introduced into the cell on a separate plasmid at the same time as the gene of interest, or they can be introduced on the same plasmid. If on the same plasmid, the selectable marker and the gene of interest can be under the control of different promoters or the same promoter, the latter arrangement producing a dicistronic message. Constructs of this type are known in the art (See, e.g., Levinson and Simonsen, U.S. Pat. No. 4,713,339). It may also be advantageous to add additional DNA, known as "carrier DNA" to the mixture that is introduced into the cells.

In one embodiment, a vector is employed that is capable of integrating the desired gene sequences into the host cell chromosome. Cells that have stably integrated the introduced DNA into their chromosomes can be selected by also introducing one or more markers that allow for selection of host cells that contain the expression vector. The marker can complement an auxotrophy in the host, biocide resistance, e.g., antibiotics, or heavy metals, such as copper, or the like.

The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells that do not contain the vector; the number of copies of the vector that are desired in a particular host; and whether it is desirable to be able to "shuttle" the vector between host cells of different species.

Once one has established that the transformed host is capable of expressing the chimeric protein as a cytoplasmic or surface membrane protein in accordance with the desired regulation and at a desired level, one may then determine whether the protein is functional in the host to provide for the desired signal induction. Since the effect of signal induction of the particular cytoplasmic domain will be known, one may use established methodology for determining induction to verify the functional capability of the chimeric protein. Of course, it is important to know that ancillary signals are not required from other proteins in conjunction with the particular cytoplasmic domain, so that the failure to provide transduction of the signal can be attributed solely to the inoperability of the chimeric protein in the particular target host.

If the cells are transfected in vitro, the transfected mammalian cells are allowed to grow for a period of time, typically 1-2 days, to begin expressing the DNA sequence(s) of interest. Drug selection is then applied to select for growth of cells that are expressing the selectable marker in a stable fashion. For cells that have been transfected with an amplifiable selectable marker, the drug concentration can be increased in a stepwise manner to select for increased copy number of the cloned sequences, thereby increasing expression levels.

Host cells containing DNA constructs are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals and growth factors. The growth medium will generally select for cells containing the DNA construct by, for example, drug selection or deficiency in an essential nutrient in which the cells are complemented by the selectable marker on the DNA construct or co-transfected with the DNA construct. The pH of the medium is preferably maintained at a pH greater than about 2 and less than about 8, preferably at about pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Cultured mammalian cells are generally grown in commercially available serum-containing or serum-free media. Selection of a medium appropriate for the particular cell line used is within the level of ordinary skill in the art.

Any peptide can be used in the form of a pharmaceutically acceptable salt. Suitable acids that are capable of forming salts with the peptides include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the subject peptides include inorganic bases such as sodium hydroxide, ammonium hydroxide, potassium hydroxide and the like; and organic bases such as mono-, di-and tri-alkyl amines (e.g., triethyl amine, diisopropyl amine, methyl amine, dimethyl amine and the like) and optionally substituted ethanolamines (e.g. ethanolamine, diethanolamine and the like).

In determining the therapeutically effective amount or dose, the effective GTPase modulating amount or dose of a chimeric GAP peptide, derivative or fragment thereof, a number of factors are considered by the attending diagnostician, including, but not limited to: the species of the mammal; its size, age, and general health; the response of the individual patient; the particular compound administered; the mode of administration; the bioavailability characteristics of the preparation administered; the dose regimen selected; the use of concomitant medication; and other relevant circumstances.

The chimeric GAP proteins can be incorporated into pharmaceutical compositions and administered to a subject in vivo. Use of chimeric GAP proteins can be useful therapeutically for the treatment of disorders caused by, for example, (i) aberrant modification or mutation of a gene encoding a GAP protein; (ii) mis-regulation of the GAP gene; and (iii) aberrant post-translational modification of a GAP protein.

The chimeric GAP nucleic acid molecules and chimeric GAP proteins (also referred to herein as "active compounds") can be incorporated into pharmaceutical compositions suitable for administration. Such compositions typically comprise the nucleic acid molecule, protein, or other active agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As defined herein, a therapeutically effective amount of protein or polypeptide (i e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or derivative can include a single treatment or, preferably, can include a series of treatments.

The nucleic acid molecules can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

However, it is understood that the embodiments are not limited by any particular theory or proposed mechanism to explain its effectiveness in an end-use application.

In effecting treatment of a patient for mobilization of hematopoietic cells, a chimeric GAP peptide, derivative, analog, homolog, fragment and mixtures thereof can be administered in any form or mode, that makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing formulations can readily select the proper form and mode of administration depending upon the relevant circumstances.

A chimeric GAP peptide, derivative, analog, homolog, fragment and mixtures thereof can be administered in the form of pharmaceutical compositions or medicaments that are made by combining a chimeric GAP peptide, derivative, analog, homolog, fragment and mixtures thereof with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient can be a solid, semi-solid, or liquid material, that can serve as a vehicle or medium for the active ingredient. Suitable carriers or excipients are well known in the art. The pharmaceutical composition can be adapted for oral or parenteral use and may be administered to the patient in the form of tablets, capsules, suppositories, solution, suspensions, or the like.

The pharmaceutical compositions can be administered orally, for example, with an inert diluent or with an edible carrier. They can be enclosed in gelatin capsules or compressed into tablets. For the purpose of oral therapeutic administration, a chimeric GAP peptide, derivative or fragment thereof can be incorporated with excipients and used in the form of tablets, troches, capsules, elixirs, suspensions, syrups, wafers, chewing gums and the like. These preparations should contain at least 4% of a chimeric GAP peptide, derivative or fragment thereof the active ingredient, but can be varied depending upon the particular form and can conveniently be between 4% to about 70% of the weight of the unit. The amount of the active ingredient present in compositions is such that a unit dosage form suitable for administration will be obtained.

The tablets, pills, capsules, troches and the like can also contain one or more-of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin can be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms can contain other various materials that modify the physical form of the dosage unit, for example, as coatings. Thus, tablets or pills can be coated with sugar, shellac, or other enteric coating agents. A syrup can contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, a chimeric GAP peptide, derivative, analog, homolog, fragment or mixtures thereof can be incorporated into a solution or suspension. These preparations should contain at least 0.1% of a compound disclosed herein, but can be varied to be between 0.1 and about 50% of the weight thereof. The amount of the active ingredient present in such compositions is such that a suitable dosage will be obtained.

When administered intravenously, the peptide compositions can be combined with other ingredients, such as carriers and/or adjuvants. The peptide can also be covalently attached to a protein carrier, such as albumin, so as to minimize clearing of the peptides. There are no limitations on the nature of the other ingredients, except that they must be pharmaceutically acceptable, efficacious for their intended administration and cannot degrade the activity of the active ingredients of the compositions. The peptide compositions can also be impregnated into transdermal patches or contained in subcutaneous inserts, preferably in a liquid or semi-liquid form. A patch or insert allows therapeutically effective amounts of one or more of the subject peptides to be released in a timed-release manner.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutanol, phenol, sorbic acid or thimerosal. Further, isotonic agents such as sugars or sodium chloride can be incorporated in the subject compositions.

Production of sterile injectable solutions containing the subject peptides is accomplished by incorporating these compounds in the required amount in the appropriate solvent with various ingredients enumerated above, as required, followed by sterilization, preferably filter sterilization. To obtain a sterile powder, the above solutions are vacuum-dried or freeze-dried as necessary.

The solutions or suspensions can also include one or more of the following adjuvants depending on the solubility and other properties of a chimeric GAP peptide, derivative or fragment thereof: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose.

The parenteral preparation can be enclosed in ampules, disposable syringes or multiple dose vials made of glass or plastic.

The pharmacological composition will preferably comprise a chimeric GAP peptide or derivative or fragment thereof along with a pharmaceutically acceptable carrier, fillers or excipients. The administering step can comprise administering a pharmacological composition comprising a chimeric GAP peptide, derivative or fragment thereof along with pharmaceutically acceptable carrier, fillers or excipients.

The methods can be by oral administration of the GTPase modulating composition or a pharmaceutically acceptable salt or derivative thereof into said mammal. The methods provide for the fact that the administration of the chimeric molecule is in a unitary dose of from about 1 to about 1000 mg. A unitary dose is generally administered from about 1 to about 3 time a day.

The administering step can comprise parenteral administration of the chimeric compound or a pharmaceutically acceptable salt or derivative thereof into said mammal. This administration can be by transdermal administration, subcutaneous injection, intravenous injection, intraperitoneal injection, intramuscular injection, intrastemal injection, intrathecal injection, intracerebroventricular injection and infusion techniques.

The method of also comprises administering chimeric compound or a pharmaceutically acceptable salt or derivative thereof along with a lipophilic compound, such as a lipophilic solvent or carrier. The lipophilic solvent or carrier can be an organic solvent, phosphatidyl choline and cholesterol.

The pharmaceutical compositions can be formulated for the oral, sublingual, subcutaneous, intravenous, transdermic or rectal administrations in dosage units and in admixture with pharmaceutical excipients or vehicles. Convenient dosage forms include, among those for oral administration, tablets, powders, granulates, and, among those for parenteral administration, solutions especially for transdermal administration, subcutaneous injection, intravenous injection, intraperitoneal injection, intramuscular injection, intrastemal injection, intrathecal injection and infusion techniques.

The dosage can vary widely as a function of the age, weight and state of health of the patient, the nature and the severity of the ailment, as well as of the administration route. These doses can naturally be adjusted for each patient according to the results observed and the blood analyses previously carried out.

The following references, to the extent that they provide exemplary procedural or other details supplementary to those set forth herein, are specifically incorporated herein by reference in their entirety: U.S. Pat. Nos. 6,410,323; 6,191,147; 6,184,203; 5,863,532; 5,574,025; 5,470,832; 5,244,916; 5,043,268, and U.S. provisional patent applications 60/523, 599 (GTPase Inhibitors and Methods of Use), filed Nov. 20, 2003; 60/527,589 (Methods of Enhancing Stem Cell Engraftment), filed Dec. 5, 2003; and 60/494,719 (Chimeric Peptides for the Regulation of GTPases), filed Aug. 13, 2003.

In addition, information regarding procedural or other details supplementary to those set forth herein, are described in cited references specifically incorporated herein by reference.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

EXAMPLES

The following examples provides the identification of the role of Rac1 and Rac2 in hematopoietic mobilization, and methods of using inhibitors of GTPases, such as Rac1 and Rac2 to mobilize hematopoietic stem cells.

Example 1

Role of Rac1, 2, and 3 in Hematopoeitic Cells

Rho GTPases, members of the Ras superfamily, are important regulators of cellular function and signal transduction pathways in all eukaryotic cells. In mammalian cells, this family is subdivided into Rho, Rac and Cdc42 GTPase families, all of which play distinct roles in regulating actin assembly and motility. The roles of Rho GTPases in hematopoietic cells have only recently begun to be elucidated. There are three Rac GTPases, Rac1, Rac2, and Rac3, that are highly homologous, and whose functional roles therefore may overlap. Rac1 is ubiquitously expressed, while the expression of Rac2 is restricted to cells of hematopoietic origin and Rac3 is expressed primarily in brain. Since Rac1 and Rac2 share 92% amino acid identity, hematopoietic cells provide a unique opportunity to elucidate the distinct roles of these highly related proteins.

Initially shown to regulate the actin cytoskeleton and give rise to the formation of lamellipodia and membrane ruffles, Rac1 has since been implicated in a wide variety of cellular functions including migration, cell adhesion, participation in the NADPH oxidase complex in phagocytic cells, regulation of gene transcription and activation of several kinase pathways, including mitogen-activated protein kinase (MAPK) p38 and c-jun kinase (JNK). Rac1 has also been shown to promote G1 cell cycle progression to S phase.

Previous reports identified the important and non-redundant roles of Rac2 in a wide variety of primary hematopoietic cells both in vivo and in vitro using gene-targeted mice. Rac2-deficient mice exhibit leukocytosis associated with neutrophil cellular defects in F-actin assembly, chemotaxis and superoxide production, and decreased activation of MAPKs ERK1/2 (p42/p44) and p38. Additional cellular phenotypes include defects in integrin-mediated adhesion in hematopoietic stem/progenitor (HSC/P) cells, reduced growth factor-induced cell survival associated with impaired activation of the anti-apoptotic kinase Akt in mast cells, and abnormal T- and B-lymphocyte differentiation and function. These phenotypes are present in spite of the expression of Rac1. The specific role of Rac1 has not previously been examined in hematopoietic cells. In order to study the role of Rac1 in definitive blood cell formation and function and to compare the specific and overlapping roles of Rac1 and Rac2 in blood cells, mice with a conditional Rac1 (flox) allele (Rac1flox/flox) (FIG. 1A) and mice doubly homozygous for the Rac1 flox allele and a Rac2-null allele (Rac1flox/flox; Rac2−/−) were studied. To delete floxed Rac1 sequences, Cre recombinase was either expressed in hematopoietic cells in vitro after transduction of harvested bone marrow with a bi-cistronic retroviral vector expressing Cre recombinase and enhanced green fluorescent protein (MIEG3-Cre) or in vivo by crossing the Rac1 flox allele into mice conditionally expressing Cre via an Interferon-γ (INF-γ) Mx1 promoter (FIG. 1B). Primitive hematopoietic stem/progenitor (HSC/P) cells contained within lineage-negative, c-Kit-positive (Lin−, c-Kit+) bone marrow cells were isolated by fluorescence-activated cell sorting (FACS) after Cre expression. To generate neutrophils in vitro, these cells were further incubated for 14 days in myeloid colony stimulating factors.

DNA polymerase chain reaction and immunoblot confirmed the deletion of exon 1 of the Rac1 gene in Lin−, c-Kit+ cells of Rac1flox$^{flox}$ mice. The completeness of deletion of Rac1 DNA sequences and lack of Rac1 protein after Cre recombinase treatment was similar using either in vitro or in vivo methods. Deletion of Rac1 sequences and protein was also complete in in vitro generated neutrophils and neutrophils harvested from the peripheral blood of mice exposed to Cre recombinase in vivo. The levels of activated (GTP-bound) Rac1 and Rac2 were also analyzed using PAK1-effector pull-down assay (FIG. 1C). After stimulation of Lin−, c-Kit+ cells with 100 ng/ml stem cell factor (SCF), the complete absence of GTP-bound Rac1 and Rac2 proteins was confirmed in Rac1−/−; Rac2−/− cells (lane 4). GTP-bound Rac1 protein was consistently higher in Rac2-deficient cells after stimulation (lane 2 vs. 1), while Rac2 activity in Rac1-deficient cells remained unchanged compared to WT (lane 3 vs. 1).

Figure 2:
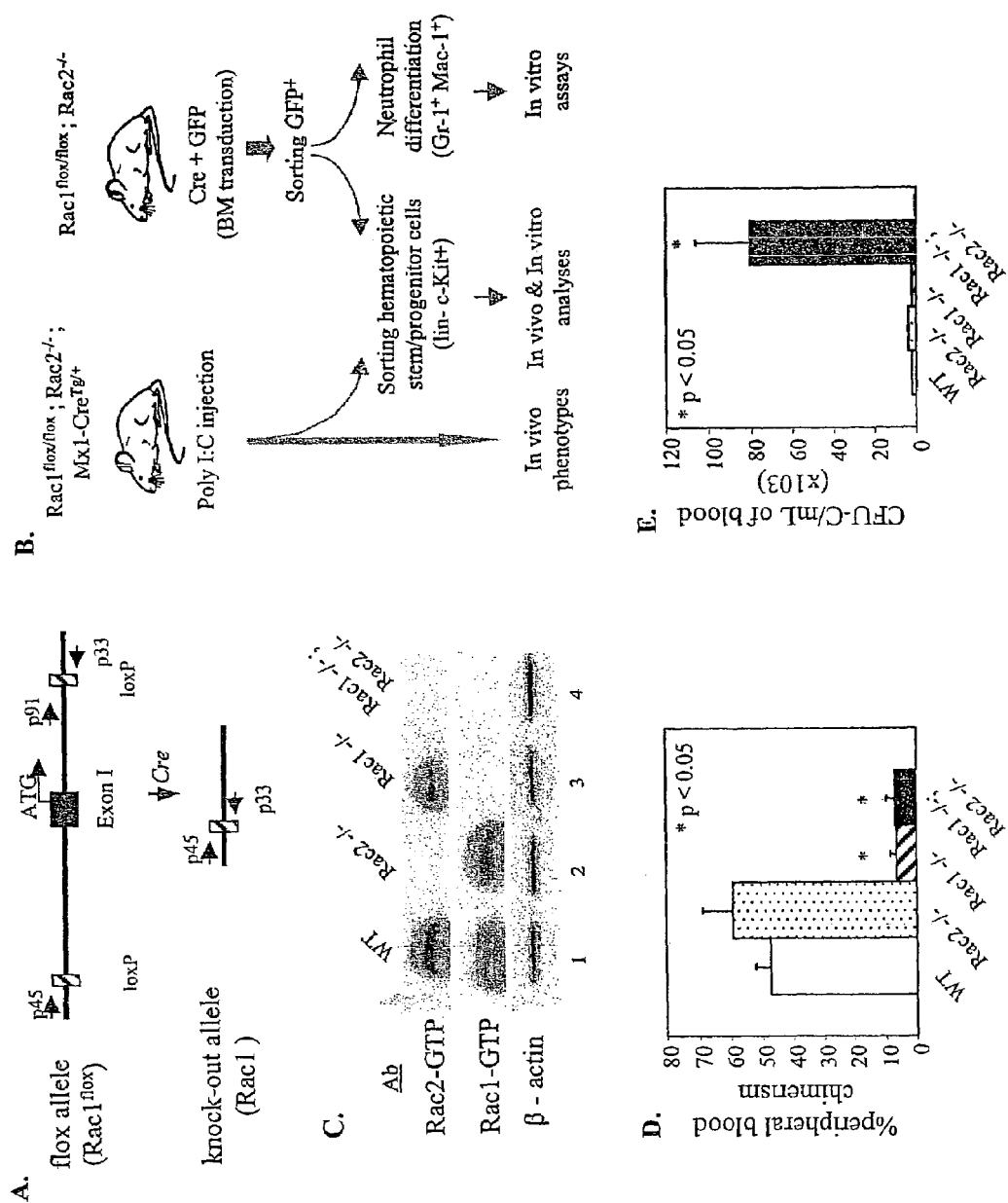
FIG. 2 shows that the generation of Rac-deficient hematopoietic cells and in vivo defective phenotypes. A) Mutant Rac1 allele. The conditional Rac1 flox allele was generated that contains two loxP sites flanking exon1. PCR analysis with three primers, p33, p45 and p91, was used to confirm deletion of exon1. B) Generation of Rac1 and Rac2 double-deficient hematopoietic cells. Rac1flox/flox was crossed into Rac2–/– null mice (A. W. Roberts et al., *Immunity* 10, 183-96, 1999, herein incorporated by reference in its entirety). Mx1-CreTg/+ mice were subsequently crossed into double mutant mice. Cre expression was either induced in vivo by Poly IC injection in Rac1flox/flox; Rac2–/–; Mx1-CreTg/+ mice or introduced in vitro into BM cells isolated from Rac1flox/flox; Rac2–/– mice by retroviral transduction with a derivative of MIEG-3 (D. A. Williams et al. *Blood* 96, 1646-1654, 2000, herein incorporated by reference in its entirety) expressing Cre (MIEG-Cre). C) Levels of active (GTP-bound) Rac proteins in HSC/Ps. WT, Rac2–/–, Rac1–/– and Rac1–/–; Rac2–/– HSC/Ps were used in a PAK1 p21-binding domain pull-down assay (V. Benard, et al. *J. Biol. Chem* 274, 13198-204, herein incorporated by reference in its entirety). GTP-bound proteins were analyzed on immunoblot using antibodies specific for Rac2 and Rac1. Levels of β-actin were used as loading controls. D) Reduced engraftment of Rac1-deficient HSC/Ps. WT or Rac-deficient bone marrow nucleated cells were transplanted into NOD/SCID recipient mice and the engraftment in peripheral blood was determined by flow cytometry using anti-CD45-APC and anti-H2Kb-PE antibodies at 6 weeks post-transplantation. Data represent mean +/– SEM, 7-12 mice per group were analyzed. *P<0.05, Rac1–/– or Rac1–/–; Rac2–/– vs. WT and Rac2–/– cells. E) Enhanced mobilization of HSC/Ps from bone marrow of Rac1–/–; Rac2–/– mice. CFU-C in peripheral blood of each genotype were enumerated. Data represent mean +/– SEM, n=3. *P<0.05, Rac1–/–; Rac2-20/– vs. WT. The results in panels C, D and E are representatives of three independent experiments.

The major phenotype noted in vivo in the absence of Rac1 was a significant reduction in the ability of HSC/P harvested from Rac1flox/flox: Mx1-CreTg/+ mice after poly I: poly C treatment to reconstitute hematopoiesis in a non-obese diabetic/severe combined immunodeficiency (NOD/SCID) engraftment model (Palacios, et al. PNAS USA 93, 5247-52, May 28, 1996)(FIG. 1D). This phenotype was specific for Rac1 deficiency, since Rac2−/− cells and WT cells exposed to Cre recombinase demonstrated normal engraftment in this assay. Lack of engraftment was also confirmed using Rac1−/− cells purified by FACS after in vitro transduction with the Cre-expressing retrovirus. In both cases, absence of Rac1 protein was confirmed by immunoblot. In addition, while, as previously reported, modest mobilization of HSC/P was seen in Rac2−/− mice (Roberts et al. Immunity 10, 183-96, 1999), absence of both Rac1 and Rac2 GTPase activity was associated with massive mobilization of progenitor colony forming cells (CFU-C) into the peripheral circulation (80,000 CFU/ml compare to ~2,000 CFU/ml in WT) (FIG. 1E). To determine the mechanism of reduced engraftment and increased trafficking of Rac-deficient HSC/P, purified cell populations were further analyzed using in vitro assays. Rac1−/− HSC/Ps were capable of forming progenitor-derived colonies in methylcellulose after stimulation with 100 ng/ml SCF, a known growth and survival factor for primitive hematopoietic cells. These colonies were significantly smaller and fewer in number than colonies derived from WT cells. In contrast, Rac2−/− HSC/Ps formed colonies similar in size and slightly higher in number compared with WT cells. Rac1−/−; Rac2−/− cells formed profoundly abnormal colonies, markedly decreased in size with a compact morphology lacking any cellular halo, suggesting these cells have both defective growth and cellular migration during colony formation. Colonies mobilized in vivo (see FIG. 1D) also demonstrated this abnormal colony morphology. HSC/Ps deficient in only Rac1 showed >50% reduction in growth in compared with WT cells. Rac2 cells demonstrated slightly increased −/− proliferation compared with WT cells and reduced growth of Rac1−/− cells had a more severe reduction in proliferation cells was associated with reduced proliferation measured by thymidine incorporation (FIG. 2B).

To further analyze the mechanism, by which Rac1 affects proliferation in primitive HSC/P cells, cell cycle analysis was performed after stimulation with 100 ng/ml SCF. In Rac 1-deficient HSC/P cells, in spite of normal Rac2 activity, significantly fewer cells entered S+G2/M in response to SCF as compared with WT cells (FIG. 2C). In contrast, the number of Rac2−/− cells in S+G2/M phases was similar to WT cells. The delay in entry into S phase was significant by 24 hours after SCF addition and persisted at 48 hours. This defect in cell cycle progression appeared directly related to Rac1 deficiency, since expression of Rac1 protein using retrovirus-mediated gene transfer restored cycle progression in Rac1−/− cells [33+4 vs. 19+3 vs. 34+3; % cells in S+G2/M, WT vs. Rac1−/− vs. Rac1−/− (Rac1+), $p<0.01$ Rac1−/− vs. Rac1−/− (Rac1+)]. These results demonstrated that Rac1 but not Rac2 activity is important for SCF-induced cycle progression in primitive hematopoietic progenitor cells.

The G1-S transition is controlled in mammalian cells by protein complexes including cyclin, cyclin dependent kinases (cdk) and cdk inhibitors. As shown in FIG. 2D, in contrast to Rac2−/− and WT cells, levels of cyclin D1 were not detectable by immunoblot in Rac1−/− HSC/Ps after SCF stimulation. In addition, Rac1−/− HSC/Ps showed decreased phosphorylation (activation) of p42/p44 MAPKs in response to SCF compared with WT cells with a more pronounced reduction in activation in Rac1−/−; Rac2−/− cells (FIG. 2E, Lane 7 and 8 vs 5). In Rac2−/− HSC/Ps p42/p44 MAPKs were activated at levels similar to WT cells (lane 6 vs 5). No activation of p38 or JNK could be demonstrated in WT cells after SCF stimulation. The reduction in Rac1-associated p42/p44 phosphorylation was directly related to the defect in cell cycle progression since a significant reduction in the number of cells in S+G2/M was also observed in WT cells treated with 30 μM U0126 Mek inhibitor, a concentration at which ERK activation is inhibited in these cells. Some inhibition in cell cycle progression was also seen with phosphoinositol-3-kinase (PI-3K) inhibition by 20 μM Ly294002 likely related to PI-3K effects on Rac activation (M. Innocenti et al., *J. Cell Biol.* 160, 17-23, Jan. 6, 2003). In WT HSC/P, progression in G1-S phase after stimulation by SCF was also accompanied by a reduction in expression of cdk inhibitors, p21cip1 and p27kip1 (FIG. 2D). The reduction in the level of p27kip1 protein seen in WT cells after SCF stimulation was absent in Rac1−/− cells. There was a small but reproducible decrease in p27kip1 in Rac2−/− cells. In contrast, p21cip1 protein was reduced to a similar level after SCF stimulation in WT, Rac1- and Rac2-deficient cells. These results demonstrate that Rac1 regulates proliferation and the G1-S transition in HSC/P in response to SCF via MAPKs p42/p44 and cyclin D1 and Rac1 absence is associated with a persistence of p27kip1 expression.

By contrast, Rac2 appears to play no role in proliferation but regulated cell survival through the known anti-apoptotic protein Akt (Kennedy, et al. Genes Dev. 11, 701-13, 1997). Rac2 but not Rac1 deficiency was associated with increased frequency of both early (Annexin-V+) and late (Annexin V+/7AAD+) apoptotic cells (FIG. 2F) and expression of the Rac2 cDNA in Rac2−/− HSC/P led to a complete reversal of the apoptotic phenotype [4.4+0.8 vs. 6.6+1.3, vs. 3.1+0.7; % Annexin-V+ cells, WT vs. Rac2−/− vs. Rac−/− (Rac2+); $p<0.01$ Rac2−/− vs. Rac2−/− (Rac2+)]. Loss of both Rac1 and Rac2 activities was associated with a more severe apoptotic phenotype compared with deficiency of only Rac2 GTPase activity (FIG. 2D). Rac2−/− HSC/P cells demonstrated reduced SCF-stimulated Akt activation compared with WT cells (FIG. 2G), similar to the Akt activation abnormalities reported in Rac2-deficient mast cells (Yang et al. Immunity 12, 557-568, 2000). The reduced Akt activation was close to normal in Rac1−/− cells. Reduced Akt activation seen in Rac2-deficient cells was linked to reduced cell survival since WT HSC/P cells incubated with either 20 μM Ly294002 (inhibitor of PI-3K) or 20 μM Akt inhibitor showed significantly increased apoptosis following SCF stimulation. An increase in apoptosis was not seen in cells treated with the Mek inhibitor. Thus, Rac2 and Rac1 separately regulate pathways controlling proliferation and survival in HSC/P. Reduced proliferation likely contributes to the lack of engraftment demonstrated in Rac1−/− c-kit+ cells.

Figure 3:
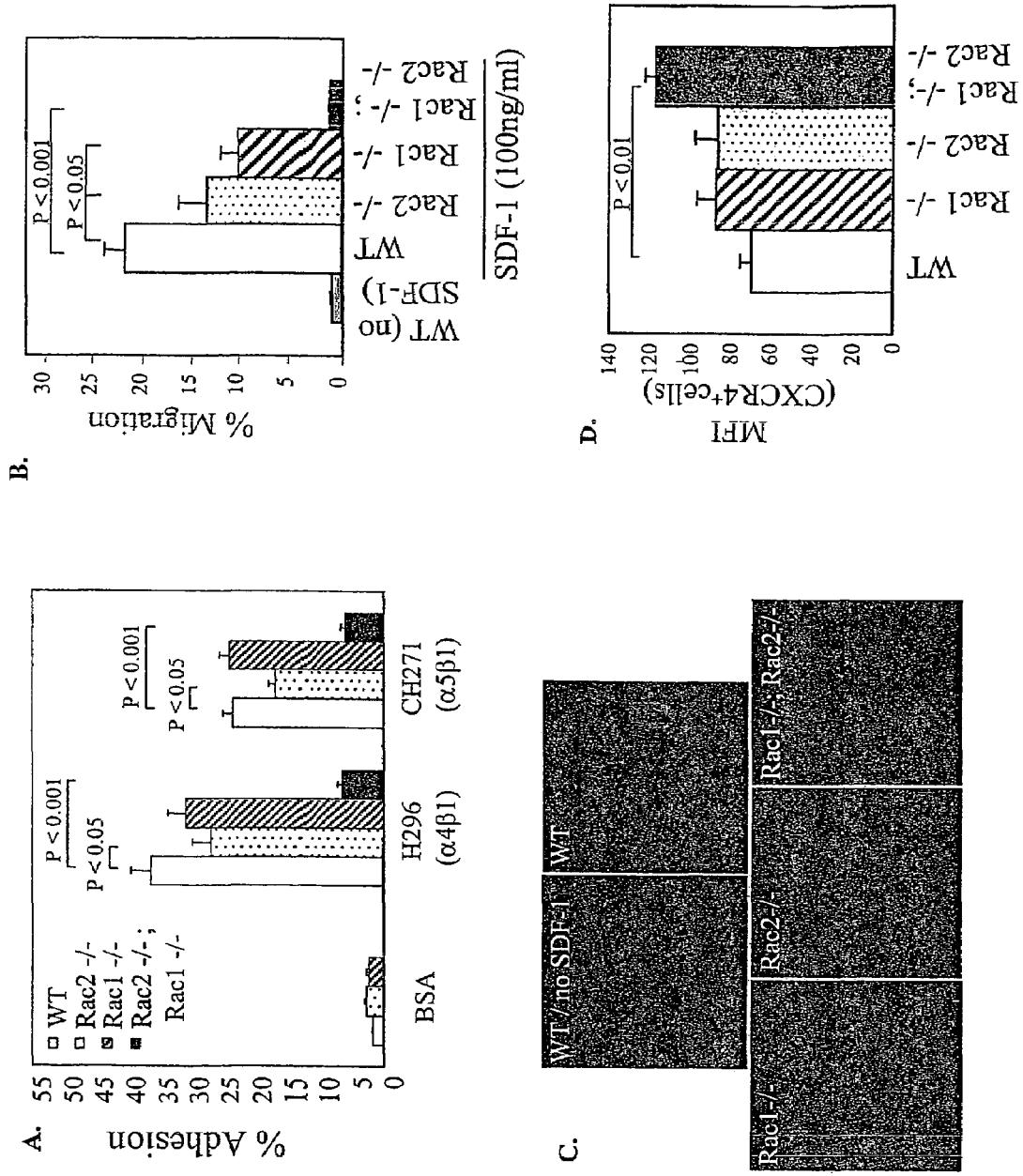
FIG. 3 shows integrin-mediated cell adhesion and chemokine-induced migration and F-actin assembly in HSC/Ps. WT, Rac2–/–, Rac1–/– and Rac1–/–; Rac2–/– HSC/Ps (lin–, c-kit+) generated by both in vitro and in vivo Cre expression were used for these studies. A) Adhesion of HSC/P cells to FN H296; Data represent mean +/– SD, n=3. B) Migration of HSC/P cells in a transwell chamber assay in response to SDF-1. The result represents the percentage of CFUs formed by the migrated cells. Analysis by enumerating c-Kit+ cells showed similar results. Mean +/– SD, n=3. C) F-actin subcellular localization. HSC/Ps were serum-depleted in HBSS and stimulated with the chemokine, SDF-1 (100 ng/ml), for 30 seconds before fixed with 2% paraformaldehyde. Cells were stained with rhodamine-labeled phalloidin on chamber slides. Subcellular localization of F-actin was detected using a fluorescence microscope with a deconvolution system. Images shown are representatives of more than 100 cells examined for each genotype. D) Expression of CXCR4 on HSC/P cell surface using FITC-conjugated anti-CXCR4 antibody. The result represents mean fluorescence intensity (MFI) analyzed by flow cytometry. Mean +/– SD, n=3. The results shown in each panel are representatives of three independent experiments. In summation, loss or reduction of Rac1 and Rac2 activity is shown to be associated with reduced adhesion of stem cells in vitro and massive mobilization of stem cells into the blood in treated individuals.

Migration, adhesion, and localization of HSC/Ps within the hematopoietic microenvironment are also involved in HSC/P engraftment. Recently, Rho GTPases have been implicated in HSC/P mobilization. Analysis of adhesion to the recombinant fibronectin (FN) fragments H-296, that contains the α4β1 binding site, or CH271, that contains the α5β1 binding site demonstrated that Rac1−/− cells adhered normally to either FN fragment compared with WT cells (FIG. 3A). However, Rac2−/− HSC/Ps and more prominently Rac1−/−; Rac2−/− cells displayed significantly decreased adhesion to both H296 and CH-271 FN peptides, strongly suggesting that Rac1 and Rac2 have overlapping roles in stem cell adhesion via integrins. These defects in adhesion to FN are not due to the decreased expression of α4β1 and α5β1 integrins on the surface of these cells. HSC/P migration in response to SDF-1, a well-characterized chemo-attractant for these cells, was studied using transwell assays. Both Rac1−/− and Rac2−/− lin−, c-kit+ HSC/Ps demonstrated decreased migration in response to SDF-1 as compared with WT cells (FIG. 3B), while absence of both Rac1 and Rac2 was associated with a near complete loss of SDF-1-stimulated cell migration. Interestingly, the migration defect seen in Rac2−/−, but not Rac1−/−, HSC/P was associated with markedly impaired cortical F-actin assembly. Considerable F-actin polymerization at the cell periphery was seen in WT and Rac1−/− HSC/Ps stimulated with 100 ng/ml SDF-1 (FIG. 3C). In contrast, F-actin polymerization at the cell periphery was not detectable Rac2−/− and Rac1−/−; Rac2−/− HSC/Ps. Indeed, in the absence of both GTPases, no obvious F-actin was seen on immunofluorescence images and the cytoplasm of these cells appeared to collapse toward the cell nucleus. The expression of the SDF-1 receptor, CXCR4, was significantly increased in Rac1−/−; Rac2−/− HSC/Ps compared with WT cells as measured by flow analysis (FIG. 3D), further suggesting that Rac activity is required downstream of CXCR4 signaling.

Cell shape changes required for cell migration in response to SDF-1 were examined with time-lapsed video microscopy. Both Rac1−/− and Rac2−/− HSC/Ps displayed some cell spreading, membrane protrusion and migration on FN-coated surface. However, Rac1−/−; Rac2−/− cells demonstrated significantly reduced spreading and actin-based membrane protrusion, and was associated with essentially no migration. These results demonstrate that while Rac2 appears to be involved in the assembly of cortical F-actin and for HSC/P integrin-mediated adhesion, but Rac1 and Rac2 share functions related to directed cell migration after SDF-1 stimulation. Taken together with the in vivo data, Rac1 appears to regulate the engraftment phenotype, likely by mediating both proliferation and migration, while Rac2 is involved in regulation of survival, adhesion and stem cell trafficking in vivo.

These data imply that Rac1 and Rac2 regulate both specific and common downstream targets to mediate actin assembly and cell structural organization, while Rac1 only has a role in mediating proliferative signaling in primitive hematopoietic cells.

Example 2

Role of Rac1, 2 and 3 in Fully Differentiated Neutrophils

The roles of Rac1 and Rac2 in fully differentiated neutrophils derived from HSC/P were studied. After in vitro differentiation, no significant differences were seen in neutrophil morphology or expression of specific differentiation antigens, Gr-1 and CD11b between each genotype. In addition, no significant differences were seen in cells deficient in either Rac1 or Rac2 (but not both) in expression of adhesion molecules CD11a, CD11b or CD18. However, Rac1−/−; Rac2−/− neutrophils displayed a significant decrease in the surface expression of each of these integrins in comparison with WT cells and this reduced integrin expression was associated with significantly reduced adhesion in comparison with WT cells via each of the integrins (FIG. 4A). However, surprisingly, a marked difference in integrin-mediated cell spreading between Rac1−/− and Rac2−/− neutrophils was evident (FIGS. 4B and 4C). Rac1−/− neutrohils displayed a ~45% increase in surface area compared to WT cells while as previously described (Roberts, 1999), Rac2−/− cells displayed a small decrease in the surface area compared with WT cells. Rac1−/−; Rac2−/− neutrophils showed no appreciable spreading and were comparable in circumference to Rac2−/− cells. Neutrophil chemotaxis in response to 10 µM formyl-methionyl-leucyl-phenylalanine (fMLP) was examined in Boyden chamber assays. In contrast to Rac2−/− neutrophils, no defect in migration was observed in Rac1-deficient neutrophils in comparison to WT cells (FIG. 4D), but Rac1−/−; Rac2−/− neutrophils demonstrated markedly reduced migration. Similar data was obtained from freshly isolated neutrophils harvested after transient Cre exposure in vivo. As shown by time-lapsed video microscopy, the absence of Rac2 was associated with perceptible defects in both cell polarization and effective directed migration in comparison with WT cells. Rac1 cells displayed normal migration but consistent with the findings in adhesion studies reported above, an increase in cell spreading and reproducible changes in pseudopodia shape was observed (see Figure B-C). In some cases, Rac1-deficiency was also accompanied by an abnormal retraction of the uropod in the migrating cell. Cell polarization and migration were totally abrogated in cells deficient in both Rac1 and Rac2. In spite of this, Rac1; Rac2−/− These results complement reports describing the separate role of Rho GTPases in control of chemotaxis in macrophage or neutrophil cell lines (Allen, et al. *J Cell Biol.* 141, 1147-57, 1998, Srinivasan et al. *J Cell Biol* 160, 375-85, Feb. 3, 2003, herein incorporated by reference in its entirety).

As seen in HSC/P, the defect in motility specifically seen in Rac2−/− neutrophils is associated with impaired cortical F-actin assembly and the assembly of F-actin was distinctly different in Rac1−/− versus Rac2−/− cells (FIG. 6E). The well-defined rim of cortical actin present at the cell periphery of WT cells totally disappeared in Rac2−/− cells, but remained clearly visible in Rac1−/− cells. In Rac1−/−; Rac2−/− neutrophils, the F-actin structure appeared to collapse into a dense network immediately surrounding the nucleus showing a complete loss of structural organization consistent with the lack of cell spreading noted above. In summary, similar to HSC/P, in fully differentiated neutrophils, Rac2 appears to be essential for the development of cortical actin in response to chemo-attractants, while Rac1 appears dispensable for migration in in vitro assays in response to fMLP. Both Rac1 and Rac2 have been demonstrated to be essential for NADPH oxidase activity in cell free assays (Abo, et al. *Nature* 353, 668-70, 1991, herein incorporated by reference in its entirety). However, after stimulation with 10 µM FMLP, the percentage of NBT+ cells, a measure of oxidase activity, was identical in Rac1−/− neutrophils compared with WT cells, using either freshly isolated peripheral blood cells or cell culture derived neutrophils (FIG. 4F). As previously described (Roberts, et al. Immunity 10, 183-196, 1999, herein incorporated by reference in its entirety), fMALP-stimulated Rac2-deficient neutrophils displayed ~60% reduction in the number of NBT+ neutrophils compared to WT cells. However, deficiency of both Rac1 and Rac2 was associated with a further reduction in the percentage of NBT+ cells compared with Rac2−/− cells (FIG. 4E). It was next determined whether, in a manner similar to HSC/P, p42/p44 MAPKs were regulated via Rac proteins in neutrophils. The level of p42/p44 phosphorylation in Rac1−/− or Rac2−/− neutrophils was reduced compared with WT cells (FIG. 4G). Rac1−/−; Rac2−/− neutrophils demonstrated severely reduced p42/p44 phosphorylation at 1 minute, with a complete absence of detectable phosphorylation at 2 minutes after stimulation. There was no significant difference in p38 phosphorylation between genotypes. WT neutrophils incubated in the presence of 10 µM U0126, a Mek inhibitor, that abrogates phosphorylation of p42/p44 surprisingly demonstrated no change in the percentage of NBT+ cells. However, U0126-treated neutrophils demonstrated a significant decrease in cell migration. Interestingly, the U0126-induced migration defect was associated with an impaired cortical actin formation, that closely mimics the abnormal actin distribution seen in Rac2-deficient neutrophils. These data suggest that the ERK kinase pathway is a major component of actin polymerization related to Rac signaling in neutrophils and is required for neutrophil migration, while this same pathway is not required for Rac-dependent superoxide generation. Taken together, Rac2 appears to be the physiologically important Rac GTPase in neutrophil migration and NADPH oxidase function, while Rac1 plays an unexpected role in controlling cell spreading. These studies define the Rho GTPases Rac1 and Rac2 as key regulators of engraftment, adhesion and localization functions of hematopoietic cells and further suggest that unique functions attributable to each relate in part to subcellular localization.

Example 3

Analysis of the Content of Hematopoietic Progenitors in Peripheral Blood, Bone Marrow and Spleen of Double Rac1/Rac2 Knockout (KO) Mice This experiment was used to analyze the effect of in vivo loss of function of Rac1 and Rac2 in the mobilization of hematopoietic progenitors from bone marrow to peripheral blood.

Conditional KO Rac1 mice were generated by Dr. Kwiatkowski (Brigham's and Women's Hospital, Harvard University, Boston, Mass.) by using standard protocols consisting of transfection of 129/Sv cells with recombinant cDNA homologous to the Exon1 of the murine Rac1 gene. The transfected plasmid contained sequences encoding two lox sequences (floxed) and between them, a neomycin phosphotransferase cassette. Selected 129/Sv were injected into pseudo-pregnant female mice according to standard methods.

F1 mice were intercrossed to obtain double flox/flox mice and later on, backcrossed with C57B1/6 mice.

Rac1KO mice were intercrossed with Rac2KO mice (generated by Drs. D. Williams & M. Dinauer) and later with Mx-Cre transgenic mice (generated by Dr. Klaus Rajewsky) that express Cre-recombinase expression from an interferon-responsive promoter element.

In order to induce interferon expression and therefore, Cre-recombinase expression, double-stranded polyribonucleotide poly-I/poly-C was injected (350 µg/day every other day, Pharmacia, Upsala, Sweden). A total of 4 to 8 injections were given to guarantee the recombination of the Rac1 gene.

Two days after the last injection of poly-I/poly-C, mice were killed by $CO_2$ inhalation. Femorae, tibiae, iliac crest, spleen and 0.3-0.8 mL of blood were collected.

Bone marrow cells were obtained as a single-cell suspension by crushing femorae, tibiae and the iliac crest in a mortar and sieving through a 30 mm sterile nylon filter. Single cell suspension of splenocytes was obtained by carefully mincing with glass slides and sieving through a 30 µm mesh sterile nylon filter. Single-cell suspension BM and spleen cells, and blood cells were lysed in ammonium chloride solution on ice and centrifuged. Cells were washed in PBS and finally suspended in IMDM (Life Technologies) containing 10% fetal calf serum (FCS, Hyclone), penicillin 50 IU/mL/streptomycin 0.1 mg/mL (Life Technologies) and counted.

Cells were suspended in a solution containing 1% methylcellulose (Methocult M-3134, Stem Cell Technologies), 30% FCS, 2mM glutamine (Life Technologies), 1% protease-free BSA (Boehringer Mannheim), 100 µM beta-Mercaptoethanol) Fisher Scientific), penicillin 50 IU/mL/streptomycin 0.1 mg/mL (Life Technologies), 0.2 mM bovine hemine (Sigma), 2 U/mL rh-erythropoietin (Epopen), 100 ng/ml rr-SCF (Amgen, Thousand Oaks, Calif.), 100 ng/mL rm-IL-3 (Peprotech) and 100 ng/mL rhG-CSF (neupogen, Amgen, Thousand Oaks, Calif.). A total number of $2 \times 10^4$ BM cells, $2 \times 10^5$ spleen cells and between $2.5 \times 10^5$-$1 \times 10^6$ blood leukocytes were plated per 35-mm dish (Nunc). Dishes were incubated for 10 days at 37° C. and 10% $CO_2$ and later, CFU-GM, BFU-E and CFU-mix were individually identified, scored and recorded as a total number of colonies (called CFU-C).

Example 4

Analysis of the Migration of Hematopoietic Progenitors Transduced with Different Chimeric GAP(GTPase Activating Protein)-Rho GTPase Tail Proteins This experiment intends to analyze the role of "ex vivo" individual loss of functions of RAC, Cdc42 and RhoA in a model that measures the ability of hematopoietic progenitors to migrate through a gradient of an attractant chemokine.

Plasmid generation. Retroviral constructs were based on the pMX-IRES-FGP backbone with a simian virus 40 early promoter-driven gene between the multicloning sites and the 3' long terminal repeat. In the cloning site located between the 5'LTR and the IRES coding sequence, different cDNA fragments were included generating a total of 9 plasmids. All these cDNA fragments contained at their 5'-end the influenza hemagglutinin antigen epitope tag. From the 5' end to the 3'-end, the following chimeric cDNAs were included: plasmid G (bcrGAP), containing the human bcr protein fraction corresponding to the amino acids 996-1227 (SEQ ID NO:6) where the GAP activity is located; plasmid A (bcrGAP-rac1tail; SEQ ID NO:11), containing the same fraction fused in frame with the murine RAC1 C-terminal twelve amino acids (181-192); plasmid B (bcrGAP-rac2tail; SEQ ID NO:12), like plasmid A but containing the same amino acid fraction but from Rac2; plasmid C (bcrGAP-rac3tail; SEQ ID NO:13), like plasmid A and B, but containing the same amino acid fraction from Rac3. Plasmid J contained the GAP-containing protein fraction of human Cdc42 (Cdc42-GAP; SEQ ID NO:4). Plasmid I (Cdc42GAP-cdc42tail; SEQ ID NO:10) contained the same cDNA fused in frame with the murine Cdc42 C-terminal twelve amino acids. Plasmid L (p190GAP; SEQ ID NO:2) contained the GAP-containing protein fraction of human p190, that is the predominant GAP for RhoA. Plasmid K (p190GAP-rhoA-tail; SEQ ID NO:7) contained the same cDNA as plasmid L but included the murine RhoA C-terminal twelve amino acids in the fusion protein. The ninth plasmid consisted of a control plasmid (Control) that contained all the retroviral backbone, IRES and GFP but no other expressed gene.

Retroviral supernatant generation. Retroviral supernatants were generated by transient transfection of the packaging cell line Phoenix-Eco. Briefly, Phoenix-Eco cells were grown until 60-70% confluency in DMEM+4 mM L-Glutamine (Life Technologies) supplemented with 10% FCS at 37° C., 10% CO2. Cells were transfected with 8 µg of plasmidic DNA plus lipofectAMIME (Life Technologies, Inc.) according to manufacturer's instructions. After 16 hours, fresh medium containing 10 mM sodium butyrate was added and cells were incubated for 6 hours at 37° C., 10% $CO_2$. After that time, medium was replaced by fresh medium and cells incubated overnight. Supernatant was harvested every 24 hours and replaced by new fresh medium for 72 hours consecutive hours.

Transduction of target cells. 5-fluorouracil (150 mg/Kg) was injected intraperitoneally into C57Bl/6 mice. After 48 hours, mice were sacrificed by CO2 inhalation. Bone marrow cells were obtained as a single-cell suspension by crushing femorae, tibiae and the iliac crest in a mortar and sieving through a 30-µm sterile nylon filter. Low-density bone marrow cells were obtained after a density gradient procedure on Histopaque 10083 (Sigma, St. Louis, Mo.) according to manufacturer's instructions. A total of $1-2 \times 10^6$ low-density BM cells were cultured (prestimulation) in IMDM (Life Technologies, Inc.) containing 10% FCS, 2 mM glutamine (Life Technologies), penicillin 50 IU/mL/streptomycin 0.1 mg/mL (Life Technologies, Inc.), 100 ng/ml 44-SCF, 100 ng/mL rm-MGDF (both from Amgen, Thousand Oaks, Calif.) and 100 ng/mL rhG-CSF (Neupogen, Amgen, Thousand Oaks, Calif.) at 37° C., 10% $CO_2$ for 48 hours. After that time, two 24 hour-cycles of retroviral transduction were performed consisting of culture of prestimulated cells in CH-296-coated 6-well plates at 37° C., 10% $CO_2$ in a medium containing retroviral supernatant and cytokines (100 ng/ml rr-SCF, 100 ng/mL rm-MGDF and 100 ng/mL rhG-CSF).

Example 5

Migration of Hematopoietic Progenitors (Migration of CFU-C)

Transduced cells were labeled with anti-ckit MoAb (CD117, Pharmingen-BD, San Jose, Calif.) and c-kit+/GFP+ cells were separated in a FACSVantage SE with DiVa option sorting device (Becton-Dickinson, San Jose, Calif.). A total of 50,000 cultured 5-FU (2d) LD c-kit+/GFP+ cells suspended in 100 mcL of serum-free chemotaxis buffer (RPMI 1640 containing 0.5% protease-free BSA) was added to the upper chamber of a 5-μm pore filter (Transwell, 24-well cell cultures, Costar) and 0.6 mL of serum-free chemotaxis buffer containing 100 ng/mL SCF-1α (Preprotech Inc.) was added to the lower chamber. Cells were allowed to migrate for 4 hours at 37° C., 10% $CO_2$. After that, the upper chamber was carefully removed and the cells in the lower chamber were resuspended and divided into aliquots for enumeration and CFU-C assay (as above). The fraction of migrating CFU-C was normalized by the number of CFU-C migrating after transduction with the control plasmid.

Example 6

Rac Mobilization in vivo

Figure 4:
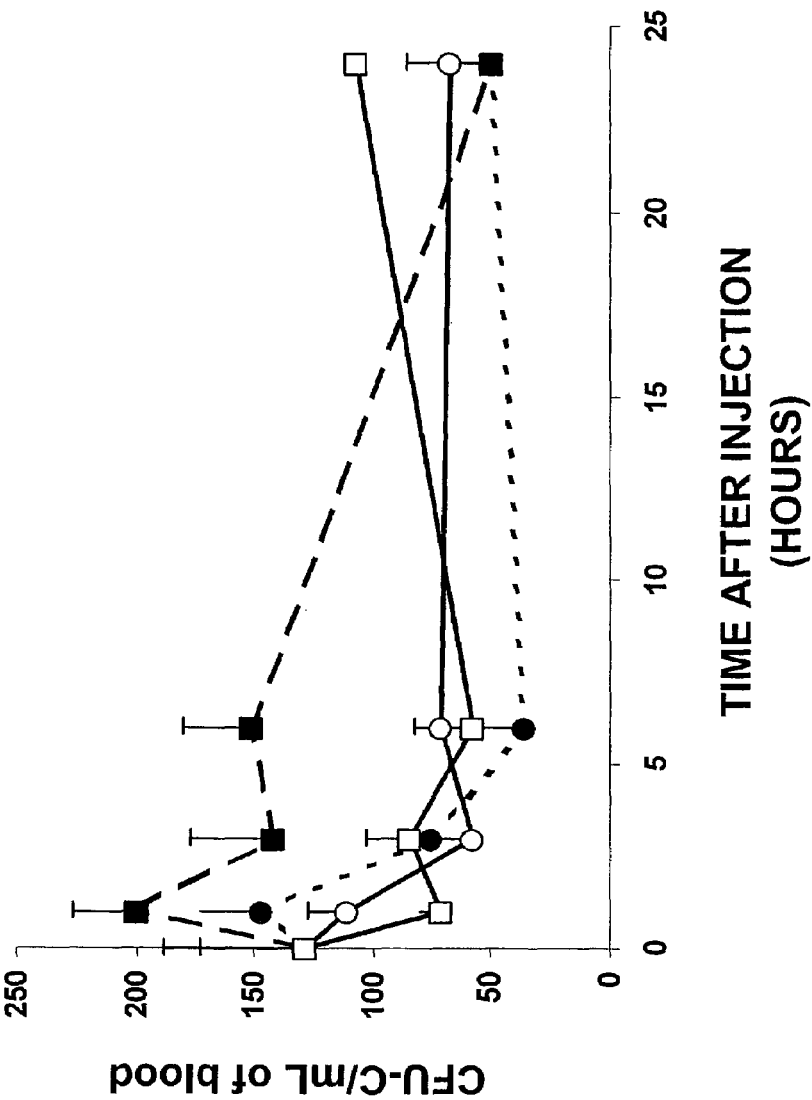
FIG. 4 shows NSC23776, an inhibitor of GEF interaction with Rac proteins, or PBS as a control was administered by intraperitoneal injection to normal mice. At the indicated time points after injection, mice were bled and analyzed for the number of progenitor cells in the peripheral blood. Three doses of drug were administered. Each point represents samples from 6 mice, mean +/– SEM.
Figure 5:
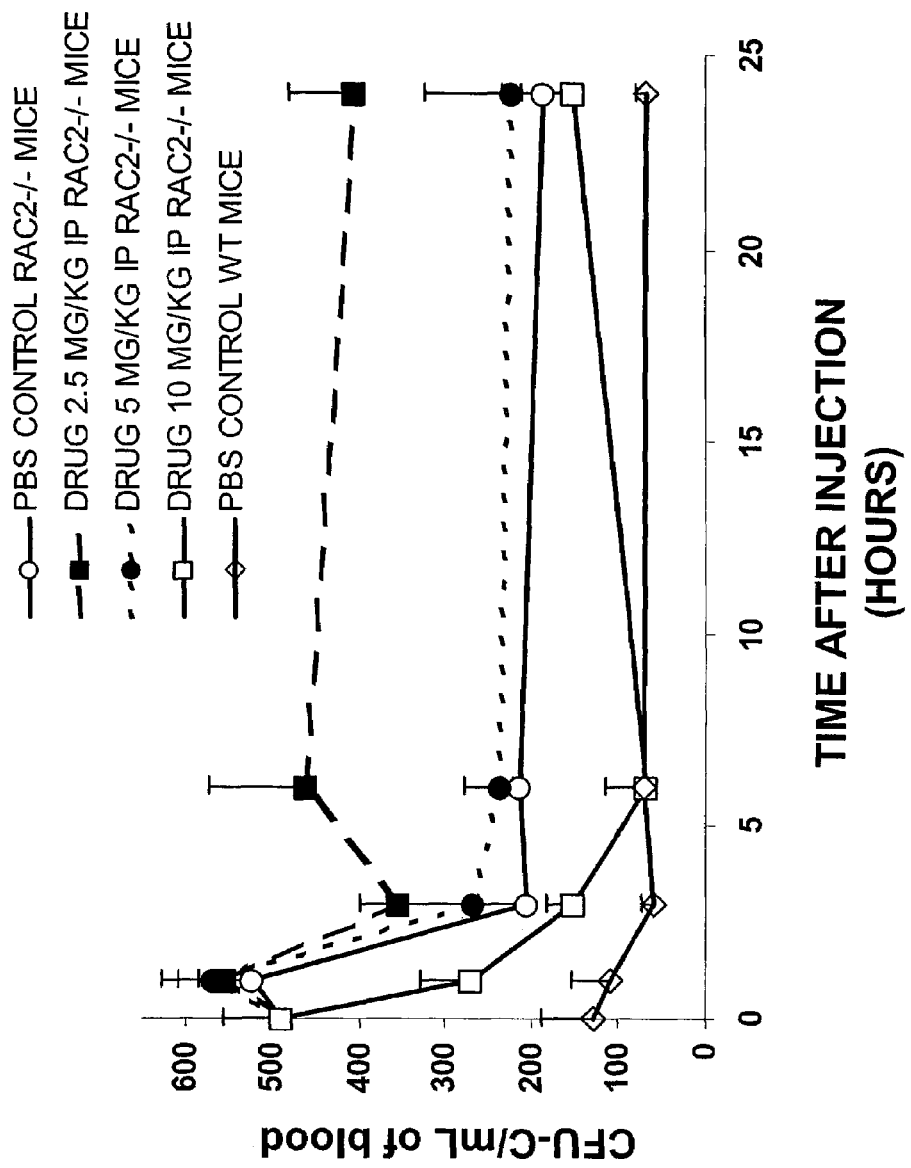
FIG. 5 shows NSC23776, an inhibitor of GEF interaction with Rac proteins, or PBS as a control was administered by intraperitoneal injection to normal mice and mice with genetic deficiency of Rac2 (Rac2–/– mice). At the indicated time points after injection, mice were bled and analyzed for the number of progenitor cells in the peripheral blood. Three doses of drug were administered. Each point represents samples from 6 mice, mean +/– SEM.

FIGS. 4 and 5 provide data using a small molecule inhibitor of Rac2. This data provides evidence that a small molecule inhibitor that targets Rac does indeed lead to mobilization of HSC/progenitor cells in normal mice and an additive effect in Rac2−/− mice.

In FIG. 4, NSC23776, an inhibitor of GEF interaction with Rac proteins, or PBS as a control was administered by intraperitoneal injection to normal mice. At the indicated time points after injection, mice were bled and analyzed for the number of progenitor cells in the peripheral blood. Three doses of drug were administered. Each point represents samples from 6 mice, mean +/− SEM.

In FIG. 5, NSC23776 or PBS as a control was administered by intraperitoneal injection to normal mice and mice with a genetic deficiency of Rac2 (Rac2−/− mice). At the indicated time points after injection, mice were bled and analyzed for the number of progenitor cells in the peripheral blood. Three doses of drug were administered. Each point represents samples from 6 mice, mean +/− SEM. For information on how to make and use NSC23776 and other small molecule inhibitors, see copending U.S. Provisional application 60/523,599, filed Nov. 20, 2003.

---

What is claimed is:

1. A method for mobilizing peripheral blood precursor cells from bone marrow into peripheral blood comprising: administering to a subject in need of treatment to mobilize peripheral blood precursor cells, an effective amount of at least one GTPase inhibitor.

2. The method of claim 1, wherein the peripheral blood precursor cells are hematopoietic cells selected from the group consisting of progenitor cells and stem cells.

3. The method of claim 1, wherein said GTPase inhibitor is a Rac GTPase inhibitor.

4. The method of claim 3, wherein said Rac GTPase inhibitor is an inhibitor of Rac1.

5. The method of claim 4, further comprising administering an inhibitor of Rac1 and an inhibitor of Rac2.

6. The method of claim 1, further comprising observing an increased mobility of peripheral blood precursor cells in the subject.

7. The method of claim 6, wherein said observing comprises collecting a blood sample and counting the number of peripheral blood precursor cells.

8. The method of claim 1, further comprising collecting mobilized stem cells for identification and/or analysis.

9. The method of claim 1, further comprising administering a growth factor prior to or concurrently with administering the GTPase inhibitor.

10. The method of claim 9, wherein the growth factor is G-CSF.

11. A method for mobilizing peripheral blood precursor cells from bone marrow into peripheral blood comprising: administering to a subject in need of treatment an effective amount of at least one GTPase inhibitor, wherein the GTPase inhibitor comprises an isolated fusion polypeptide comprising: a) a Rho GAP domain peptide and b) a C-terminus targeting peptide, wherein the C-terminus targeting peptide comprises the amino acid sequence of SEQ ID NO:18.

12. A method for mobilizing peripheral blood precursor cells from bone marrow into peripheral blood comprising: administering to a subject in need of treatment an effective amount of at least one GTPase inhibitor, wherein the GTPase inhibitor comprises an isolated fusion polypeptide comprising:
a) a Rho GAP domain peptide;
b) a C-terminus targeting peptide; and
c) an N-terminus membrane-translocating peptide,
wherein the amino acid sequence of the N-terminus membrane translocation peptide is Gly-Arg-Arg-Arg-Arg-Arg-Arg-Arg-Gly-Thr-Arg-Gln-Gln-Lys-Arg-Pro, (SEQ ID NO:23).

13. A method for mobilizing peripheral blood precursor cells from bone marrow into peripheral blood comprising: administering to a subject in need of treatment an effective amount of at least one GTPase inhibitor, wherein the GTPase inhibitor comprises an isolated fusion polypeptide comprising the amino acid sequence of SEQ ID NO:11.

* * * * *

UNITED STATES PATENT AND TRADEMARK OFFICE
CERTIFICATE OF CORRECTION

| | | |
|---|---|---|
| PATENT NO. | : 7,417,026 B2 | Page 1 of 1 |
| APPLICATION NO. | : 10/918328 | |
| DATED | : August 26, 2008 | |
| INVENTOR(S) | : Williams et al. | |

It is certified that error appears in the above-identified patent and that said Letters Patent is hereby corrected as shown below:

Please <u>delete</u> the following paragraph, column 1, lines 09 through 12, from the specification of the above-identified patent application:

"This invention was made in part with Government support under Grant Nos. R01DK59955 and R01GM60523, awarded by the National Institutes of Health. The Government may have certain rights in this invention."

and <u>insert</u> therefore the following paragraph:

--STATEMENT REGARDING FEDERALLY SPONSORED RESEARCH

This invention was made in part with Government support under Grant Nos. R01DK059955 and R01GM060523, awarded by the National Institutes of Health. The Government has certain rights in this invention.--

Signed and Sealed this
Thirty-first Day of May, 2011

David J. Kappos
*Director of the United States Patent and Trademark Office*

UNITED STATES PATENT AND TRADEMARK OFFICE
CERTIFICATE OF CORRECTION

PATENT NO. : 7,417,026 B2  
APPLICATION NO. : 10/918328  
DATED : August 26, 2008  
INVENTOR(S) : Williams Page 1 of 1

It is certified that error appears in the above-identified patent and that said Letters Patent is hereby corrected as shown below:

In the Specification

Column 1, lines 9 through 12, after

STATEMENT REGARDING FEDERALLY SPONSORED RESEARCH delete

"This invention was made in part with Government support under Grant Nos. R01DK059955 and R01GM060523, awarded by the National Institute of Health. The Government has certain rights in this invention."

and insert therefore the following paragraph:

--This invention was made with government support under DK059955 and GM060523, awarded by the National Institutes of Health. The government has certain rights in the invention.--

Signed and Sealed this  
Twenty-sixth Day of November, 2013

Margaret A. Focarino  
*Commissioner for Patents of the United States Patent and Trademark Office*